(12) United States Patent
Yamamoto et al.

(10) Patent No.: US 9,966,541 B2
(45) Date of Patent: May 8, 2018

(54) BISCARBAZOLE DERIVATIVE HOST MATERIALS AND GREEN EMITTER FOR OLED EMISSIVE REGION

(75) Inventors: Hitoshi Yamamoto, Ewing, NJ (US);
Michael S. Weaver, Ewing, NJ (US);
Julia J. Brown, Ewing, NJ (US);
Kazuki Nishimura, Tokyo (JP);
Toshihiro Iwakuma, Tokyo (JP)

(73) Assignees: IDEMITSU KOSAN CO. LTD., Tokyo (JP); UNIVERSAL DISPLAY CORPORATION, Ewing, NJ (US)

( * ) Notice: Subject to any disclaimer, the term of this patent is extended or adjusted under 35 U.S.C. 154(b) by 479 days.

(21) Appl. No.: 14/400,801

(22) PCT Filed: Jun. 14, 2012

(86) PCT No.: PCT/US2012/042360
§ 371 (c)(1),
(2), (4) Date: Apr. 7, 2015

(87) PCT Pub. No.: WO2013/187896
PCT Pub. Date: Dec. 19, 2013

(65) Prior Publication Data
US 2015/0243905 A1    Aug. 27, 2015

(51) Int. Cl.
*H01L 51/00* (2006.01)
*C07D 403/14* (2006.01)
(Continued)

(52) U.S. Cl.
CPC ........ *H01L 51/0072* (2013.01); *C07D 403/14* (2013.01); *C07D 405/14* (2013.01);
(Continued)

(58) Field of Classification Search
None
See application file for complete search history.

(56) References Cited

U.S. PATENT DOCUMENTS 7,635,526 B2 * 12/2009 Stossel .............. C07F 15/0033
136/263
RE45,216 E   10/2014 Tanaka et al.
(Continued)

FOREIGN PATENT DOCUMENTS

JP       2012216801 A    11/2012
KR  10-2011-0048840 A     5/2011
(Continued)

OTHER PUBLICATIONS

Official Action dated May 30, 2016 in counterpart Japanese patent application No. 2015-517225.

*Primary Examiner* — Robert S Loewe
(74) *Attorney, Agent, or Firm* — Duane Morris LLP

(57) ABSTRACT

An organic electroluminescence device utilizes a novel combination comprising one or more biscarbazole derivative compounds as the phosphorescent host material in combination with a green phosphorescent dopant material in the light emitting region of the device, where the biscarbazole derivative compounds are represented by a formula (1A) or (1B) below; where $A_1$ represents a substituted or unsubstituted nitrogen-containing heterocyclic group having 1 to 30 ring carbon atoms; $A_2$ represents a substituted or unsubstituted aromatic hydrocarbon group having 6 to 30 ring carbon atoms, or substituted or unsubstituted nitrogen-containing heterocyclic group having 1 to 30 ring carbon atoms; $X_1$ and $X_2$ each are a linking group; $Y_1$ to $Y_4$ each represent a substituent; p and q represent an integer of 1 to 4; and r and s represent an integer of 1 to 3; and the green phosphorescent dopant material is a phosphorescent organometallic complex having a chemical structure represented by LL'L"M wherein M is a metal that forms octahedral complexes, L, L', and L" are equivalent or inequivalent bidentate ligands wherein each L comprises a substituted or
(Continued)

unsubstituted phenylpyridine ligand coordinated to M through an sp² hybridized carbon and N; and, one of L, L' and L" is different from at least one of the other two.

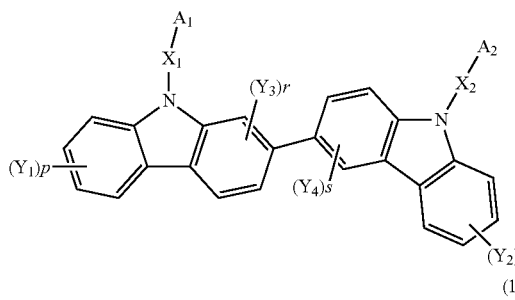

(1A)

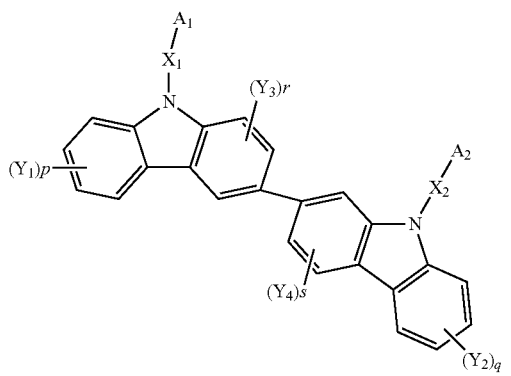

(1B)

11 Claims, 1 Drawing Sheet

(51) Int. Cl.
| | |
|---|---|
| *C09K 11/06* | (2006.01) |
| *C07D 405/14* | (2006.01) |
| *H01L 51/50* | (2006.01) |
| *H01L 51/52* | (2006.01) |

(52) U.S. Cl.
CPC .......... *C09K 11/06* (2013.01); *H01L 51/0052* (2013.01); *H01L 51/0067* (2013.01); *H01L 51/0073* (2013.01); *H01L 51/0085* (2013.01); *H01L 51/0094* (2013.01); *C09K 2211/1014* (2013.01); *C09K 2211/1029* (2013.01); *C09K 2211/1044* (2013.01); *C09K 2211/1048* (2013.01); *C09K 2211/1059* (2013.01); *C09K 2211/1074* (2013.01); *C09K 2211/1088* (2013.01); *C09K 2211/185* (2013.01); *H01L 51/5016* (2013.01); *H01L 51/5056* (2013.01); *H01L 51/5072* (2013.01); *H01L 51/5088* (2013.01); *H01L 51/5206* (2013.01); *H01L 51/5221* (2013.01); *H01L 2251/301* (2013.01); *H01L 2251/308* (2013.01); *H01L 2251/5384* (2013.01)

(56) References Cited

U.S. PATENT DOCUMENTS

| | | | | |
|---|---|---|---|---|
| 2009/0124805 | A1* | 5/2009 | Alleyne | C09K 11/06 546/4 |
| 2010/0270916 | A1 | 10/2010 | Xia et al. | |
| 2011/0057171 | A1 | 3/2011 | Adamovich et al. | |
| 2011/0227049 | A1* | 9/2011 | Xia | C07F 15/0033 257/40 |
| 2011/0260138 | A1* | 10/2011 | Xia | C07D 405/14 257/40 |
| 2011/0278555 | A1 | 11/2011 | Inoue | |
| 2011/0279020 | A1* | 11/2011 | Inoue | C07D 209/82 313/504 |
| 2012/0012829 | A1 | 1/2012 | Lin et al. | |
| 2012/0181518 | A1* | 7/2012 | Ogiwara | H01L 51/5004 257/40 |
| 2012/0211736 | A1 | 8/2012 | Kim et al. | |
| 2013/0092913 | A1* | 4/2013 | Nishimura | C09K 11/06 257/40 |
| 2014/0151647 | A1* | 6/2014 | Mizuki | H05B 33/20 257/40 |

FOREIGN PATENT DOCUMENTS

| | | |
|---|---|---|
| WO | 2010-027583 A1 | 3/2010 |
| WO | 2012108881 A1 | 8/2012 |
| WO | 2013162284 A1 | 10/2013 |
| WO | 2013172835 A1 | 11/2013 |

* cited by examiner

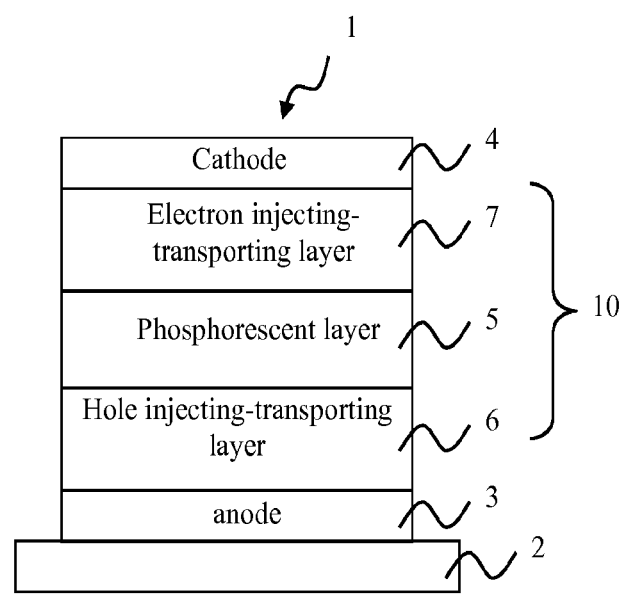

BISCARBAZOLE DERIVATIVE HOST MATERIALS AND GREEN EMITTER FOR OLED EMISSIVE REGION

BACKGROUND OF THE INVENTION

The present invention relates to an organic electroluminescent (EL) device such as an organic light emitting device (hereinafter abbreviated as an OLED) and materials capable of being used in such an OLED. In particular, it relates to an OLED which comprises a light emitting layer which emits a green light, and materials for an OLED which are used for the same.

RELATED ART

OLEDs which comprise an organic thin film layer which includes a light emitting layer located between an anode and a cathode are known in the art. In such devices, emission of light may be obtained from exciton energy, produced by recombination of a hole injected into a light emitting layer with an electron.

Generally, OLEDs are comprised of several organic layers in which at least one of the layers can be made to electroluminesce by applying a voltage across the device. When a voltage is applied across a device, the cathode effectively reduces the adjacent organic layers (i.e., injects electrons), and the anode effectively oxidizes the adjacent organic layers (i.e., injects holes). Holes and electrons migrate across the device toward their respective oppositely charged electrodes. When a hole and electron meet on the same molecule, recombination is said to occur, and an exciton is formed. Recombination of the hole and electron in luminescent compounds is accompanied by radiative emission, thereby producing electroluminescence.

Depending on the spin states of the hole and electron, the exciton resulting from hole and electron recombination can have either a triplet or singlet spin state. Luminescence from a singlet exciton results in fluorescence, whereas luminescence from a triplet exciton results in phosphorescence. Statistically, for organic materials typically used in OLEDs, one quarter of the excitons are singlets, and the remaining three-quarters are triplets (see, e.g., Baldo, et al., Phys. Rev. B, 1999, 60, 14422). Until the discovery that there were certain phosphorescent materials that could be used to fabricate practical electro-phosphorescent OLEDs (U.S. Pat. No. 6,303,238) and, subsequently, demonstration that such electro-phosphorescent OLEDs could have a theoretical quantum efficiency of up to 100% (i.e., harvesting all of both triplets and singlets), the most efficient OLEDs were typically based on materials that fluoresced. Fluorescent materials luminesce with a maximum theoretical quantum efficiency of only 25% (where quantum efficiency of an OLED refers to the efficiency with which holes and electrons recombine to produce luminescence), since the triplet to ground state transition of phosphorescent emission is formally a spin forbidden process. Electro-phosphorescent OLEDs have now been shown to have superior overall device efficiencies as compared with electro-fluorescent OLEDs (see, e.g., Baldo, et al., Nature, 1998, 395, 151 and Baldo, et al., Appl. Phys. Lett. 1999, 75(3), 4).

Due to strong spin-orbit coupling that leads to singlet-triplet state mixing, heavy metal complexes often display efficient phosphorescent emission from such triplets at room temperature. Accordingly, OLEDs comprising such complexes have been shown to have internal quantum efficiencies of more than 75% (Adachi, et al., Appl. Phys. Lett., 2000, 77, 904). Certain organometallic iridium complexes have been reported as having intense phosphorescence (Lamansky, et al., Inorganic Chemistry, 2001, 40, 1704), and efficient OLEDs emitting in the green to red spectrum have been prepared with these complexes (Lamansky, et al., J. Am. Chem. Soc., 2001, 123, 4304). Phosphorescent heavy metal organometallic complexes and their respective devices have been the subject of U.S. Pat. Nos. 6,830,828 and 6,902,830; U.S. Publications 2006/0202194 and 2006/0204785; and U.S. Pat. Nos. 7,001,536; 6,911,271; 6,939,624; and 6,835,469.

OLEDs, as described above, generally provide excellent luminous efficiency, image quality, power consumption and the ability to be incorporated into thin design products such as flat screens, and therefore hold many advantages over prior technology, such as cathode ray devices.

However, improved OLEDs, including, for example, the preparation of OLEDs having greater current efficiency are desirable. In this regard, light emitting materials (phosphorescent materials) have been developed in which light emission is obtained from a triplet exciton in order to enhance internal quantum efficiency.

As discussed above, such OLEDs can have a theoretical internal quantum efficiency up to 100% by using such phosphorescent materials in the light emitting layer (phosphorescent layer), and the resulting OLED will have a high efficiency and low power consumption. Such phosphorescent materials may be used as a dopant in a host material which comprises such a light emitting layer.

In a light emitting layer formed by doping with a light emitting material such as a phosphorescent material, excitons can efficiently be produced from a charge injected into a host material. Exciton energy of an exciton produced may be transferred to a dopant, and emission may be obtained from the dopant at high efficiency. Exitons may be formed either on the host materials or directly on the dopant.

In order to achieve intermolecular energy transfer from a host material to a phosphorescent dopant with high device efficiencies, the excited triplet energy EgH of the host material must be greater than the excited triplet energy EgD of the phosphorescent dopant.

In order to carry out intermolecular energy transfer from a host material to a phosphorescent dopant, an excited triplet energy Eg (T) of the host material has to be larger than an excited triplet energy Eg (S) of the phosphorescent dopant.

CBP (4,4'-bis(N-carbazolyl)biphenyl) is known to be a representative example of a material having an efficient and large excited triplet energy. See, e.g., U.S. Pat. No. 6,939,624. If CBP is used as a host material, energy can be transferred to a phosphorescent dopant having a prescribed emission wavelength, such as green, and an OLED having a high efficiency can be obtained. When CBP is used as a host material, the luminous efficiency is notably enhanced by phosphorescent emission. However, CBP is known to have a very short lifetime, and therefore it is not suitable for practical use in EL devices such as an OLED. Without being bound by scientific theory, it is believed that this is because CBP may be heavily deteriorated by a hole due to its oxidative stability not being high, in terms of molecular structure.

International Patent Application Publication WO 2005/112519 discloses a technique in which a condensed ring derivative having a nitrogen-containing ring such as carbazole and the like is used as a host material for a phosphorescent layer showing green phosphorescence. The current efficiency and the lifetime are improved by the above technique, but it is not satisfactory in a certain case for practical use.

On the other hand, a wide variety of host materials (fluorescent hosts) for a fluorescent dopant showing fluorescent emission are known, and various host materials can be proposed which, by combination with a fluorescent dopant, may form a fluorescent layer which exhibits excellent luminous efficiency and lifetime.

In a fluorescent host, an excited singlet energy Eg (S) is larger than in a fluorescent dopant, but an excited triplet energy Eg (T) of such a host is not necessarily larger. Accordingly, a fluorescent host cannot simply be used in place of a phosphorescent host as a host material to provide a phosphorescent emitting layer.

For example, anthracene derivatives are known well as a fluorescent host. However, an excited state triplet energy Eg (T) of anthracene derivatives may be as small as about 1.9 eV. Thus, energy transfer to a phosphorescent dopant having an emission wavelength in a visible light region of 500 nm to 720 nm cannot be achieved using such a host, since the excited state triplet energy would be quenched by a host having such a low triplet state energy. Accordingly, anthracene derivatives are unsuitable as a phosphorescent host.

Perylene derivatives, pyrene derivatives and naphthacene derivatives are not preferred as phosphorescent hosts for the same reason.

The use of aromatic hydrocarbon compounds as phosphorescent hosts is disclosed in Japanese Patent Application Laid-Open No. 142267/2003. That application discloses phosphorescent host compounds with a benzene skeleton core and with two aromatic substituents bonded at meta positions.

However, the aromatic hydrocarbon compounds described in Japanese Patent Application Laid-Open No. 142267/2003 assume a rigid molecular structure having a good symmetric property and provided with five aromatic rings in which molecules are arranged in a bilaterally symmetrical manner toward a central benzene skeleton. Such an arrangement has the drawback of a likelihood of crystallization of the light emitting layer.

On the other hand, OLEDs in which various aromatic hydrocarbon compounds are used are disclosed in International Patent Application Publications WO 2007/046685; Japanese Patent Application Laid-Open No. 151966/2006; Japanese Patent Application Laid-Open No. 8588/2005; Japanese Patent Application Laid-Open No. 19219/2005; Japanese Patent Application Laid-Open No. 19219/2005; and Japanese Patent Application Laid-Open No. 75567/2004. However, the efficiency of these materials as a phosphorescent host is not disclosed.

In addition, OLEDs prepared by using various fluorene compounds are disclosed in Japanese Patent Application Laid-Open No. 043349/2004; Japanese Patent Application Laid-Open No. 314506/2007; and Japanese Patent Application Laid-Open No. 042485/2004. However, the effectiveness of these materials as a phosphorescent host is not disclosed.

Further, Japanese Patent Application Laid-Open No. 042485/2004 discloses hydrocarbon compounds in which a condensed polycyclic aromatic ring is bonded directly to a fluorene ring. However, the effectiveness of an OLED prepared by combining such materials with a phosphorescent material is not disclosed, and the application discloses perylene and pyrene rings which are known to have a small triplet energy level as condensed polycyclic aromatic rings, and which are not preferred for use as a light emitting layer of a phosphorescent device, and materials which are effective for a phosphorescent device are not selected.

Despite the recent advancements in OLED technology, there remains a need for host materials which can transfer energy to a phosphorescent material with high efficiency and with an extended lifetime.

SUMMARY OF THE INVENTION

One embodiment of the present disclosure provides an organic electroluminescence device such as an OLED that utilizes a novel combination comprising a biscarbazole derivative compound as a host compound and a green phosphorescent dopant material in the light emitting region of the device. The green phosphorescent dopant material is an organometallic phosphorescent material. The organic electroluminescence device of the present disclosure comprises a cathode, an anode, and a plurality of organic thin-film layers provided between the cathode and the anode. At least one of the organic thin-film layers is an emitting layer comprising a green phosphorescent dopant material and a host material that is a biscarbazole derivative compound represented by a formula (1A) or (1B) below:

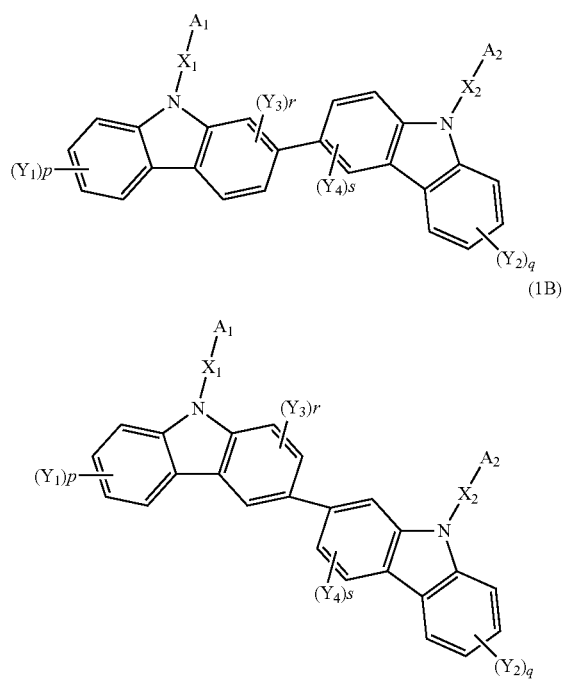

where $A_1$ represents a substituted or unsubstituted nitrogen-containing heterocyclic group having 1 to 30 carbon atoms forming a ring;

$A_2$ represents a substituted or unsubstituted aromatic hydrocarbon group having 6 to 30 ring carbon atoms, or substituted or unsubstituted nitrogen-containing heterocyclic group having 1 to 30 ring carbon atoms;

$X_1$ and $X_2$ each are a linking group and independently represents a single bond, substituted or unsubstituted aromatic hydrocarbon group having 6 to 30 ring carbon atoms, substituted or unsubstituted fused aromatic hydrocarbon group having 6 to 30 ring carbon atoms, substituted or unsubstituted aromatic heterocyclic group having 2 to 30 ring carbon atoms, or substituted or unsubstituted fused aromatic heterocyclic group having 2 to 30 ring carbon atoms;

$Y_1$ to $Y_4$ independently represent a hydrogen atom, fluorine atom, cyano group, substituted or unsubstituted alkyl group having 1 to 20 carbon atoms, substituted or unsubstituted alkoxy group having 1 to 20 carbon atoms, substituted or unsubstituted haloalkyl group having 1 to 20 carbon atoms, substituted or unsubstituted haloalkoxy group having 1 to 20 carbon atoms, substituted or unsubstituted alkylsilyl having 1 to 10 carbon atoms, substituted or unsubstituted arylsilyl having 6 to 30 carbon atoms, substituted or unsubstituted aromatic hydrocarbon group having 6 to 30 ring carbon atoms, substituted or unsubstituted fused aromatic hydrocarbon group having 6 to 30 ring carbon atoms, substituted or unsubstituted aromatic heterocyclic group having 2 to 30 ring carbon atoms, or substituted or unsubstituted fused aromatic heterocyclic group having 2 to 30 ring carbon atoms;

adjacent ones of $Y_1$ to $Y_4$ are allowed to be bonded to each other to form a ring structure;

p and q represent an integer of 1 to 4; r and s represent an integer of 1 to 3; and when p and q are an integer of 2 to 4 and r and s are an integer of 2 to 3, a plurality of $Y_1$ to $Y_4$ are allowed to be the same or different.

The green phosphorescent dopant material is a phosphorescent organometallic complex having a chemical structure represented by

LL'L"M wherein M is a metal that forms octahedral complexes, L, L', and L" are equivalent or inequivalent bidentate ligands wherein each L comprises a substituted or unsubstituted phenylpyridine ligand coordinated to M through an sp2 hybridized carbon and N; and, one of L, L' and L" is different from at least one of the other two. The ligand L, L', and L" are coordinated to the metal M having atomic number greater than 40. Preferably, the metal M is Ir.

As used herein, "hydrogen atom" includes hydrogen isotopes such as protium, deuterium, and tritium.

According to an aspect of the present disclosure, the green phosphorescent dopant material is an organometallic compound having a substituted chemical structure represented by the following formula (4A):

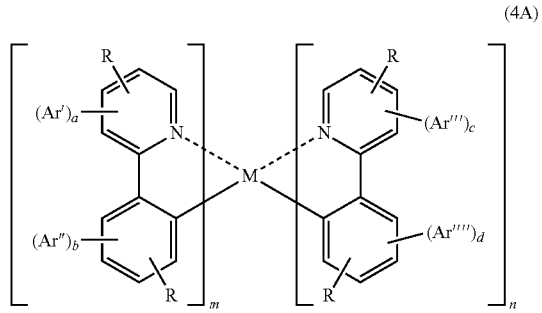

(4A)

where each R is independently selected from the group consisting of H, alkyl, alkenyl, alkynyl, alkylaryl, CN, $CF_3$, $C_nF_{2n+1}$, trifluorovinyl, $CO_2R$, $C(O)R$, $NR_2$, $NO_2$, OR, halo, aryl, heteroaryl, substituted aryl, substituted heteroaryl or a heterocyclic group;

Ar', Ar", Ar'" and Ar"" each independently represent a substituted or unsubstituted aryl or heteroaryl substituent on the phenylpyridine ligand;

a is 0 or 1;

b is 0 or 1;

c is 0 or 1;

d is 0 or 1;

m is 1 or 2;

n is 1 or 2;

m+n is the maximum number of ligands that can be coordinated to M, and wherein at least one of a, b, c, and d is 1 and when at least one of a and b is 1 and at least one of b and c is 1, at least one of Ar' and Ar" is different from at least one of Ar'" and Ar"".

According to an aspect of the present disclosure, the green phosphorescent dopant material is an organometallic compound represented by the following formula 4B:

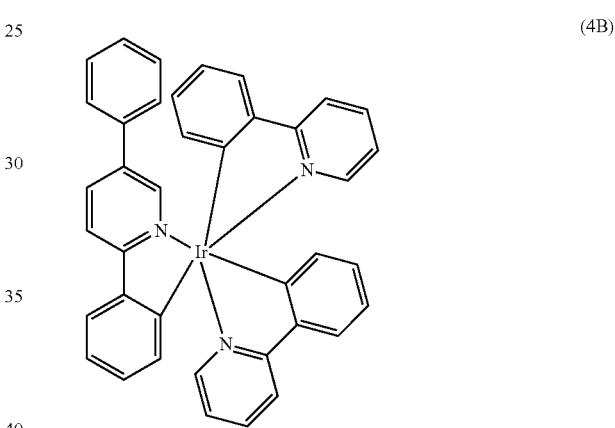

(4B)

According to another aspect of the present disclosure, the organic EL device comprises the green phosphorescent dopant material represented by the formula 4B and the host material is a biscarbazole derivative compound represented by a formula 1H or 2H shown below:

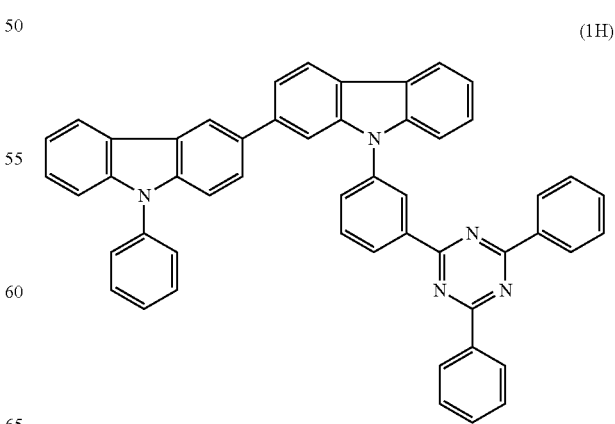

(1H)

(2H)

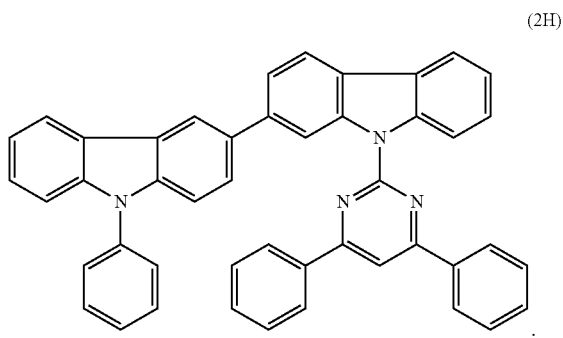

In another embodiment, the organic electroluminescence device comprises a cathode, an anode, and a plurality of organic thin-film layers provided between the cathode and the anode, wherein at least one of the organic thin-film layers is an emitting layer comprising a first host material, a second host material, and a green phosphorescent dopant material as emitter. The first host material of the pair of co-host materials is a biscarbazole derivative compound represented by the formula (1A) or (1B) as described above:

(1A)

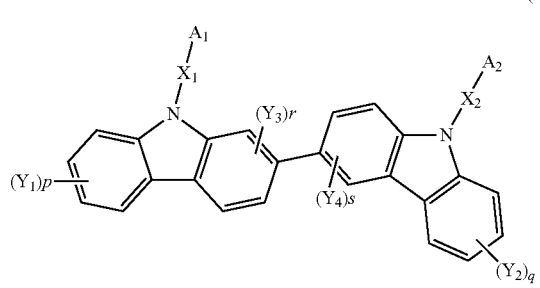

(1B)

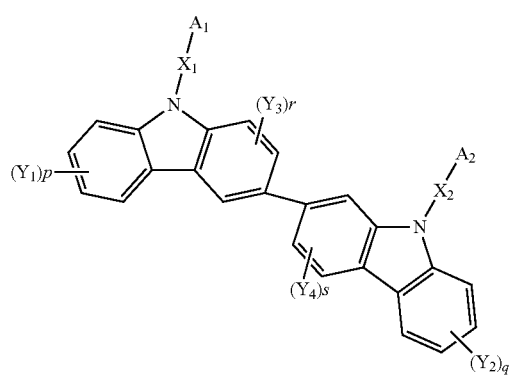

The second host material of the pair of co-host mateirals is a biscarbazole derivative compound represented by a formula (1A'), (1B') or (2) below:

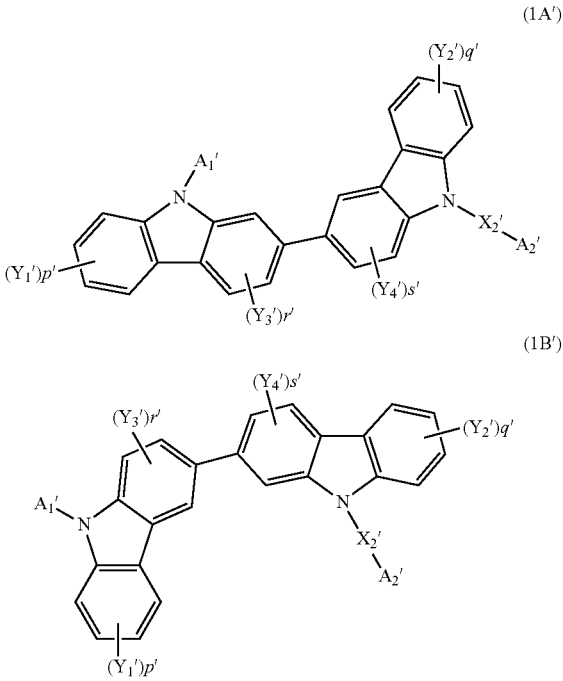

where $A_1'$ represents a substituted or unsubstituted nitrogen-containing heterocyclic group having 1 to 30 carbon atoms forming a ring;

$A_2'$ represents a substituted or unsubstituted aromatic hydrocarbon group having 6 to 30 ring carbon atoms, or substituted or unsubstituted nitrogen-containing heterocyclic group having 1 to 30 ring carbon atoms;

$X_2'$ is a linking group and independently represent, a single bond, substituted or unsubstituted aromatic hydrocarbon group having 6 to 30 ring carbon atoms, substituted or unsubstituted fused aromatic hydrocarbon group having 6 to 30 ring carbon atoms, substituted or unsubstituted aromatic heterocyclic group having 2 to 30 ring carbon atoms, or substituted or unsubstituted fused aromatic heterocyclic group having 2 to 30 ring carbon atoms;

$Y_1'$ to $Y_4'$ independently represent a hydrogen atom, fluorine atom, cyano group, substituted or unsubstituted alkyl group having 1 to 20 carbon atoms, substituted or unsubstituted alkoxy group having 1 to 20 carbon atoms, substituted or unsubstituted haloalkyl group having 1 to 20 carbon atoms, substituted or unsubstituted haloalkoxy group having 1 to 20 carbon atoms, substituted or unsubstituted alkylsilyl having 1 to 10 carbon atoms, substituted or unsubstituted arylsilyl having 6 to 30 carbon atoms, substituted or unsubstituted aromatic hydrocarbon group having 6 to 30 ring carbon atoms, substituted or unsubstituted fused aromatic hydrocarbon group having 6 to 30 ring carbon atoms, substituted or unsubstituted aromatic heterocyclic group having 2 to 30 ring carbon atoms, or substituted or unsubstituted fused aromatic heterocyclic group having 2 to 30 ring carbon atoms;

adjacent ones of $Y_1'$ to $Y_4'$ are allowed to be bonded to each other to form a ring structure;

p' and q' represent an integer of 1 to 4; r' and s' represent an integer of 1 to 3; and when p' and q' are an integer of 2 to 4 and r' and s' are an integer of 2 to 3, a plurality of $Y_1'$ to $Y_4'$ are allowed to be the same or different;

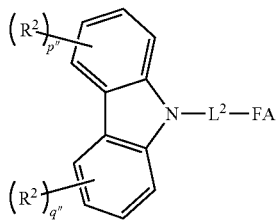

(2)

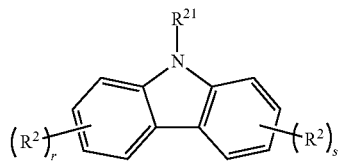

(2-3)

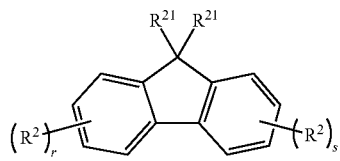

(2-4)

where R² independently represents a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 6 to 30 ring carbon atoms, or a substituted or unsubstituted aryloxy group having 6 to 30 ring carbon atoms;

p″ and q″ are independently an integer of 0 to 4;

a plurality of R² are mutually the same or different;

adjacent groups of R² are allowed to bond with each other to form a ring;

L² represents a single bond or a linking group, the linking group being one or a combination of a substituted or unsubstituted aryl group having 6 to 30 ring carbon atoms, a substituted or unsubstituted heterocyclic group having 5 to 30 ring atoms, and a cycloalkyl group having 5 to 30 ring carbon atoms; and FA represents a substituted or unsubstituted fused aromatic cyclic group having 6 to 30 ring carbon atoms, or a substituted or unsubstituted fused aromatic heterocyclic group having 5 to 30 ring atoms. Examples of FA in the second host material represented by formula (2) are represented by any one of the formulas (2-1) to (2-4):

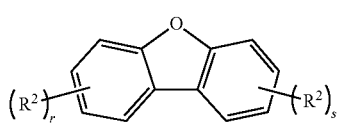

(2-1)

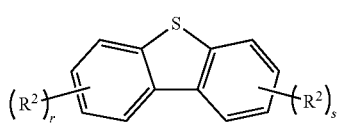

(2-2)

where R² and R²¹ represent the same as R² of the formula (2);

one of R² is a single bond to bond with L² in the formula (2); and r and s are an integer of 0 to 4.

The green phosphorescent dopant material as emitter is an organometallic complex having a chemical structure represented by

LL′L″M where M is a metal that forms octahedral complexes, L, L′, and L″ are equivalent or inequivalent bidentate ligands wherein each L comprises a substituted or unsubstituted phenylpyridine ligand coordinated to M through an sp2 hybridized carbon and N; and, one of L, L′ and L″ is different from at least one of the other two. The ligand L, L′, and L″ are coordinated to the metal M having atomic number greater than 40. Preferably, the metal M is Ir.

According to an aspect of the organic EL device having the first and second host materials in the emitting layer, examples of the green phosphorescent dopant material are organometallic compounds having a substituted chemical structure represented by the formula (4A) as described above.

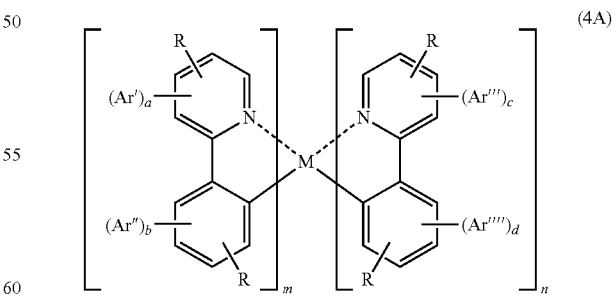

(4A)

According to another aspect of the organic EL device having the first and second host materials in the emitting layer, the green phosphorescent dopant material is an organometallic compound represented by the formula (4B)

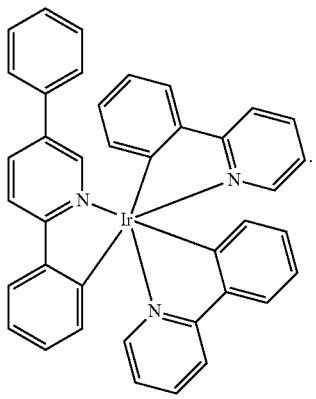

(4B)

According to another aspect of the organic EL device having the first and second host materials in the emitting layer, the green phostphorescent dopant material is an organometallic compound represented by the formula 4B, the first host material is a biscarbazole derivative compound represented by the formula 1H, and the second host material is a biscarbasole derivative compound represented by the formula 2H or a formula 3H shown below

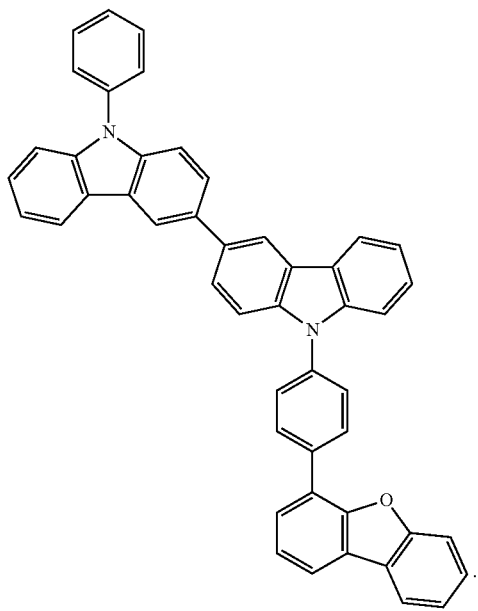

(3H)

The inventors have found that the organic EL devices containing the host materials and phosphorescent materials according to the present disclosure exhibit low voltage requirement with high luninous efficiency. Additionally, the devices having the combination of the co-host materials and the phosphorescent dopant materials in the emitting layer according to the present disclosure can exhibit additional improvement in the life time of the device.

A luminous efficiency and a lifetime of the multilayered organic EL device depend on a carrier balance of the entire organic EL device. The main factors that control the carrier balance are carrier transporting capability of each of the organic layers and carrier injecting capability in the interfacial region of separate organic layers. In the organic EL devices having the cohost combinations according to the present disclosure, the cohost materials provide an improved charge carrier balance of the entire organic EL device by putting two of positive hole transportability materials and electronic transportability materials together. The provision of such co-host materials reduce deterioration by the carrier invasion to the adjacent layer.

For example, the emitter host materials disclosed in the present disclosure can function well not only as a single host in an emitter layer but also as a cohost material in combination with a second host material that is different from them. Providing two compounds as a host material in the emitter layer, the carrier injecting capability to neighboring layers in the emitting layer (recombination region) can be balanced.

The combination of the emitter layer host material and the red phosphorescent dopant material of the present disclosure resulted in an organic EL device having an enhanced life.

BRIEF DESCRIPTION OF THE DRAWING

FIG. 1 is a schematic drawing of an exemplary arrangement for an OLED according to an exemplary embodiment of the present disclosure.

DETAILED DESCRIPTION

The OLEDs of the present invention may comprise a plurality of layers located between an anode and a cathode. Representative OLEDs according to the invention include, but are not limited to, structures having constituent layers as described below:

(1) anode/light emitting layer/cathode;
(2) anode/hole injecting layer/light emitting layer/cathode;
(3) anode/light emitting layer/electron injecting•transporting layer/cathode;
(4) anode/hole injecting layer/light emitting layer/electron injecting•transporting layer/cathode;
(5) anode/organic semiconductor layer/light emitting layer/cathode;
(6) anode/organic semiconductor layer/electron blocking layer/light emitting layer/cathode;
(7) anode/organic semiconductor layer/light emitting layer/adhesion improving layer/cathode;
(8) anode/hole injecting•transporting layer/light emitting layer/electron injecting•transporting layer/cathode;
(9) anode/insulating layer/light emitting layer/insulating layer/cathode;
(10) anode/inorganic semiconductor layer/insulating layer/light emitting layer/insulating layer/cathode;
(11) anode/organic semiconductor layer/insulating layer/light emitting layer/insulating layer/cathode;
(12) anode/insulating layer/hole injecting•transporting layer/light emitting layer/insulating layer/cathode; and
(13) anode/insulating layer/hole injecting•transporting layer/light emitting layer/electron injecting•transporting layer/cathode.

Among the OLED constituent structures described above, constituent structure number (8) is a preferred structure, but the present invention is not limited to these disclosed constituent structures.

FIG. 1 shows an OLED 1 according to an embodiment. The OLED 1 comprises a transparent substrate 2, an anode 3, a cathode 4 and a plurality of organic thin film layers 10 disposed between the anode 3 and the cathode 4. At least one of the plurality of organic thin film layers 10 is a phosphorescence emitting layer 5 comprising one or more phosphorescent host material and a phosphorescent dopant material.

The plurality of organic thin film layers 10 can include other layers such as a hole injecting•transporting layer 6 and the like between the phosphorescence emitting layer 5 and the anode 3. The plurality of organic thin film layers 10 can also include layers such as an electron injecting•transporting layer 7 and the like between the phosphorescence emitting layer 5 and the cathode 4.

Further, there may be provided respectively an electron blocking layer disposed between the anode 3 and the phosphorescence emitting layer 5, and a hole blocking layer disposed between the cathode 4 and the phosphorescence emitting layer 5. This makes it possible to contain electrons and holes in the phosphorescence emitting layer 5 to enhance the production rate of excitons in the phosphorescence emitting layer 5.

In the present disclosure, the term "phosphorescent host" is used to refer to a host material that functions as a phosphorescent host when combined with a phosphorescent dopant and should not be limited to a classification of the host material based solely on molecular structure.

Thus, a phosphorescent host means a material constituting the phosphorescence emitting layer containing a phosphorescent dopant and does not mean a material which can be used only for a host of a phosphorescent material. A phosphorescence emitting layer is also referred to herein as a light emitting layer.

In the present specification, "a hole injecting•transporting layer" means at least either one of a hole injecting layer and a hole transporting layer, and "an electron injecting•transporting layer" means at least either one of an electron injecting layer and an electron transporting layer.

[Substrate]

The OLED of the present disclosure may be prepared on a substrate. The substrate referred to in this case is a substrate for supporting the OLED, and it is preferably a flat substrate in which light in the visible region of about 400 to about 700 nm has a transmittance of at least about 50%.

The substrate may include a glass plate, a polymer plate and the like. In particular, the glass plate may include soda lime glass, barium•strontium-containing glass, lead glass, aluminosilicate glass, borosilicate glass, barium borosilicate glass, quartz and the like. The polymer plate may include polycarbonate, acryl, polyethylene terephthalate, polyether sulfide, polysulfone and the like.

[Anode and Cathode]

An anode in the OLED of the present disclosure assumes the role of injecting a hole into the hole injecting layer, the hole transporting layer or the light emitting layer. Typically the anode has a work function of 4.5 eV or more.

Specific examples of a material suitable for use as the anode include indium tin oxide alloy (ITO), tin oxide (NESA glass), indium zinc oxide, gold, silver, platinum, copper and the like. The anode can be prepared by forming a thin film from electrode substances, such as those discussed above, by a method such as a vapor deposition method, a sputtering method and the like.

When light is emitted from the light emitting layer, the transmittance of light in the visible light region in the anode is preferably larger than 10%. The sheet resistance of the anode is preferably several hundred a/square or less. The film thickness of the anode is selected, depending on the material, and is typically in the range of from about 10 nm to about 1 μm, and preferably from about 10 nm to about 200 nm.

The cathode comprises preferably a material having a small work function for the purpose of injecting an electron into the electron injecting layer, the electron transporting layer or the light emitting layer. Materials suitable for use as the cathode include, but are not limited to indium, aluminum, magnesium, magnesium-indium alloys, magnesium-aluminum alloys, aluminum-lithium alloys, aluminum-scandium-lithium alloys, magnesium-silver alloys and the like. For transparent or top-emitting devices, a TOLED cathode such as disclosed in U.S. Pat. No. 6,548,956 is preferred.

The cathode can be prepared, as is the case with the anode, by forming a thin film by a method such as a vapor deposition method, a sputtering method and the like. Further, an embodiment in which light emission is taken out from a cathode side can be employed as well.

[Light Emitting Layer According to First Embodiment]

The light emitting layer in the OLED of the present disclosure may be capable of carrying out the following functions singly or in combination:

(1) injecting function: a function in which a hole can be injected from an anode or a hole injecting layer in applying an electric field and in which an electron can be injected from a cathode or an electron injecting layer;

(2) transporting function: a function in which a charge (electron and hole) injected may be transferred by virtue of a force of an electric field; and (3) light emitting function: a function in which a region for recombination of an electron and a hole may be provided, and which results in the emission of light.

A difference may be present between ease of injection of a hole and ease of injection of an electron, and a difference may be present in the transporting ability shown by the mobilities of a hole and an electron.

Known methods including, for example, vapor deposition, spin coating, Langmuir Blodgett methods and the like can be used to prepare the light emitting layer. The light emitting layer is preferably a molecularly deposited film. In this regard, the term "molecularly deposited film" means a thin film formed by depositing a compound from the gas phase and a film formed by solidifying a material compound in a solution state or a liquid phase state, and usually the above-referenced molecular deposit film can be distinguished from a thin film (molecular accumulation film) formed by an LB method by a difference in an aggregation structure and a higher order structure and a functional difference originating in it.

In preferred embodiments, the film thickness of the light emitting layer is preferably from about 5 to about 50 nm, more preferably from about 7 to about 50 nm and most preferably from about 10 to about 50 nm. If the film thickness is less than 5 nm, it is likely to be difficult to form the light emitting layer and control the chromaticity. On the other hand, if it exceeds about 50 nm, the operating voltage is likely to go up.

[Host Material]

The at least one of the plurality of organic thin film layers 10 in the OLED according to an embodiment of the present disclosure is the light emitting layer comprising novel combination of a biscarbazole derivative compound as a host material in the light emitting region of the device and a green phosphorescent dopant material (the emitter) in the light emitting region. The host material is a biscarbazole derivative compound represented by a formula (1A) or (1B) below:

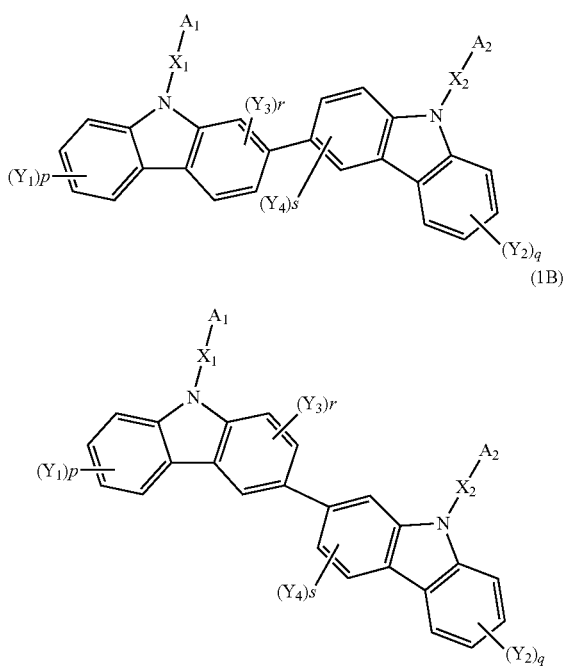

(1A)

(1B)

where $A_1$ represents a substituted or unsubstituted nitrogen-containing heterocyclic group having 1 to 30 carbon atoms forming a ring;

$A_2$ represents a substituted or unsubstituted aromatic hydrocarbon group having 6 to 30 ring carbon atoms, or substituted or unsubstituted nitrogen-containing heterocyclic group having 1 to 30 ring carbon atoms;

$X_1$ and $X_2$ each are a linking group and independently represents a single bond, substituted or unsubstituted aromatic hydrocarbon group having 6 to 30 ring carbon atoms, substituted or unsubstituted fused aromatic hydrocarbon group having 6 to 30 ring carbon atoms, substituted or unsubstituted aromatic heterocyclic group having 2 to 30 ring carbon atoms, or substituted or unsubstituted fused aromatic heterocyclic group having 2 to 30 ring carbon atoms;

$Y_1$ to $Y_4$ independently represent a hydrogen atom, fluorine atom, cyano group, substituted or unsubstituted alkyl group having 1 to 20 carbon atoms, substituted or unsubstituted alkoxy group having 1 to 20 carbon atoms, substituted or unsubstituted haloalkyl group having 1 to 20 carbon atoms, substituted or unsubstituted haloalkoxy group having 1 to 20 carbon atoms, substituted or unsubstituted alkylsilyl having 1 to 10 carbon atoms, substituted or unsubstituted arylsilyl having 6 to 30 carbon atoms, substituted or unsubstituted aromatic hydrocarbon group having 6 to 30 ring carbon atoms, substituted or unsubstituted fused aromatic hydrocarbon group having 6 to 30 ring carbon atoms, substituted or unsubstituted aromatic heterocyclic group having 2 to 30 ring carbon atoms, or substituted or unsubstituted fused aromatic heterocyclic group having 2 to 30 ring carbon atoms;

adjacent ones of $Y_1$ to $Y_4$ are allowed to be bonded to each other to form a ring structure;

p and q represent an integer of 1 to 4; r and s represent an integer of 1 to 3; and when p and q are an integer of 2 to 4 and r and s are an integer of 2 to 3, a plurality of $Y_1$ to $Y_4$ are allowed to be the same or different.

According to another aspect of the present disclosure, in the devices of the present embodiment, the $A_1$ in the host compound can be selected from the group consisting of a substituted or unsubstituted pyridine ring, substituted or unsubstituted pyrimidine ring, substituted or unsubstituted triazine ring, and a substituted or unsubstituted quinazoline ring.

According to another aspect of the present disclosure, in the devices of the present embodiment, the $A_1$ in the host compound can be selected from a substituted or unsubstituted benzofuranyl group, a substituted or unsubstituted dibenzofuranyl group, a substituted or unsubstituted benzothiophenyl group, a substituted or unsubstituted dibenzothiophenyl group, a substituted or unsubstituted benzonaphthofuranyl group, or a substituted or unsubstituted benzonaphthothiophenyl group.

Examples of the biscarbazole derivative compound as the host material represented by the formula (1A) or (1B) are described later in this document as chemical formulas 10, 20, 30, 40, 50, 60, 70, 80, 90, 100, 110, 120, 130, 140 and 150. According to one embodiment, the host material can be a biscarbazole derivative compound represented by the following formula 1H or 2H:

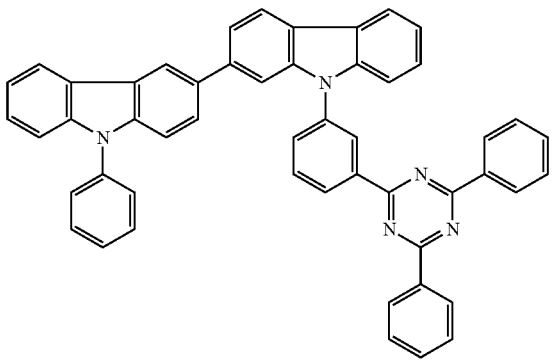

(1H)

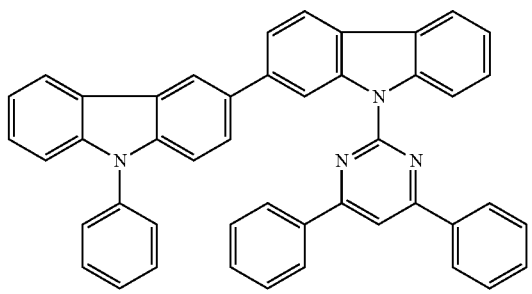

(2H)

[Green Phosphorescent Dopant Material]

The green phosphorescent dopant material is a phosphorescent organometallic complex having a chemical structure represented by

LL'L"M where M is a metal that forms octahedral complexes, L, L', and L" are equivalent or inequivalent bidentate ligands wherein each L comprises a substituted or unsubstituted phenylpyridine ligand coordinated to M through an sp2 hybridized carbon and N; and, one of L, L' and L" is different from at least one of the other two. The ligand L, L', and L"

are coordinated to the metal M having atomic number greater than 40. Preferably, the metal M is Ir.

Examples of the green phosphorescent dopant material may be an organometallic compound having a substituted chemical structure represented by the formula 4A:

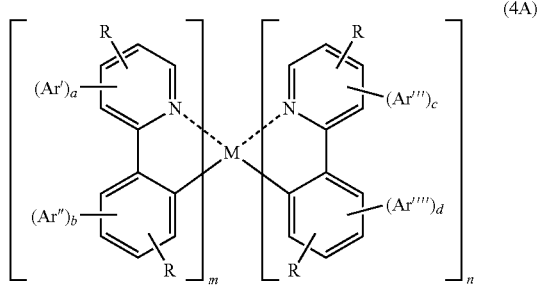

where each R is independently selected from the group consisting of H, alkyl, alkenyl, alkynyl, alkylaryl, CN, $CF_3$, $C_nF_{2n+1}$, trifluorovinyl, $CO_2R$, $C(O)R$, $NR_2$, $NO_2$, OR, halo, aryl, heteroaryl, substituted aryl, substituted heteroaryl or a heterocyclic group;

Ar', Ar'', Ar''' and Ar'''' each independently represent a substituted or unsubstituted aryl or heteroaryl substituent on the phenylpyridine ligand;
a is 0 or 1;
b is 0 or 1;
c is 0 or 1;
d is 0 or 1;
m is 1 or 2;
n is 1 or 2;
m+n is the maximum number of ligands that can be coordinated to M, and
wherein at least one of a, b, c, and d is 1 and when at least one of a and b is 1 and at least one of b and c is 1, at least one of Ar' and Ar'' is different from at least one of Ar''' and Ar''''.

In the organic EL device of the present embodiment, the phosphorescent dopant material can be an organometallic compound represented by the formula 4B below:

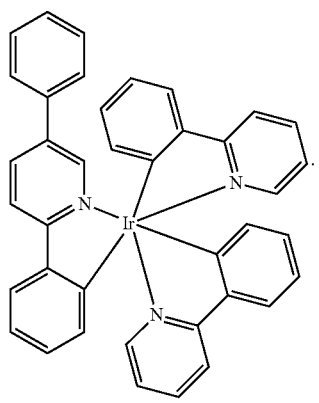

[EIL/ETL]

The electron injecting layer or the electron transporting layer, which aids injection of the electrons into the emitting layer, has a large electron mobility. The electron injecting layer is provided for adjusting energy level, by which, for instance, sudden changes of the energy level can be reduced.

The organic EL device according to this embodiment preferably includes the electron injecting layer between the emitting layer and the cathode, and the electron injecting layer preferably contains a nitrogen-containing cyclic derivative as the main component. The electron injecting layer may serve as the electron transporting layer. It should be noted that "as the main component" means that the nitrogen-containing cyclic derivative is contained in the electron injecting layer at a content of 50 mass % or more.

A preferable example of an electron transporting material for forming the electron injecting layer is an aromatic heterocyclic compound having in the molecule at least one heteroatom. Particularly, a nitrogen-containing cyclic derivative is preferable. The nitrogen-containing cyclic derivative is preferably an aromatic ring having a nitrogen-containing six-membered or five-membered ring skeleton, or a fused aromatic cyclic compound having a nitrogen-containing six-membered or five-membered ring skeleton.

The nitrogen-containing cyclic derivative is preferably exemplified by a nitrogen-containing cyclic metal chelate complex represented by the following formula E1.

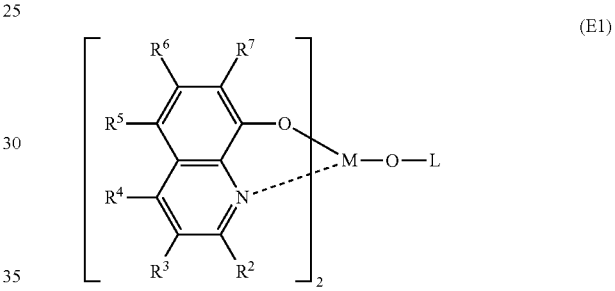

$R^2$ to $R^7$ in the formula E1 each independently represent a hydrogen atom, a halogen atom, an oxy group, an amino group, a hydrocarbon group having 1 to 40 carbon atoms, an alkoxy group, an aryloxy group, an alkoxycarbonyl group, or an aromatic heterocyclic group. These groups may be substituted or unsubstituted.

Examples of the halogen atom include fluorine, chlorine, bromine, and iodine. In addition, examples of the substituted or unsubstituted amino group include an alkylamino group, an arylamino group, and an aralkylamino group.

The alkoxycarbonyl group is represented by —COOY'. Examples of Y' are the same as the examples of the alkyl group. The alkylamino group and the aralkylamino group are represented by —$NQ^1Q^2$. Examples for each of $Q^1$ and $Q^2$ are the same as the examples described in relation to the alkyl group and the aralkyl group, and preferred examples for each of $Q^1$ and $Q^2$ are also the same as those described in relation to the alkyl group and the aralkyl group. Either one of $Q^1$ and $Q^2$ may be a hydrogen atom.

The arylamino group is represented by —$NAr^1Ar^2$. Examples for each of $Ar^1$ and $Ar^2$ are the same as the examples described in relation to the non-fused aromatic hydrocarbon group and the fused aromatic hydrocarbon group. Either one of $Ar^1$ and $Ar^2$ may be a hydrogen atom.

M in the formula E1 represents aluminum (Al), gallium (Ga) or indium (In), among which In is preferable.

L in the formula E1 represents a group represented by a formula (A') or (A'') below.

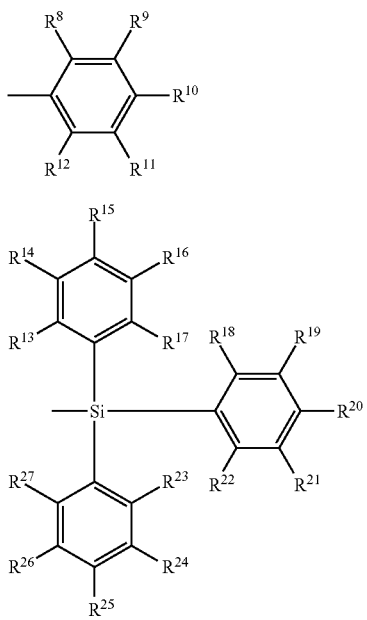

(A')

(A")

In the formula A', $R^8$ to $R^{12}$ each independently represent a hydrogen atom or a substituted or unsubstituted hydrocarbon group having 1 to 40 carbon atoms. Adjacent groups may form a cyclic structure. In the formula A", $R^{13}$ to $R^{27}$ each independently represent a hydrogen atom or a substituted or unsubstituted hydrocarbon group having 1 to 40 carbon atoms. Adjacent groups may form a cyclic structure.

Examples of the hydrocarbon group having 1 to 40 carbon atoms represented by each of $R^8$ to $R^{12}$ and $R^{13}$ to $R^{27}$ in the formulas A' and A" are the same as those of $R^2$ to $R^7$ in the formula E1.

Examples of a divalent group formed when an adjacent set of $R^8$ to $R^{12}$ and $R^{13}$ to $R^{27}$ forms a cyclic structure are a tetramethylene group, a pentamethylene group, a hexamethylene group, a diphenylmethane-2,2'-diyl group, a diphenylethane-3,3'-diyl group, a diphenylpropane-4,4'-diyl group and the like.

As an electron transporting compound for the electron injecting layer or the electron transporting layer, 8-hydroxyquinoline or a metal complex of its derivative, an oxadiazole derivative and a nitrogen-containing heterocyclic derivative are preferable. A specific example of the 8-hydroxyquinoline or the metal complex of its derivative is a metal chelate oxinoid compound containing a chelate of oxine (typically 8-quinolinol or 8-hydroxyquinoline). For instance, tris(8-quinolinol) aluminum can be used. Examples of the oxadiazole derivative are represented by the following formulas:

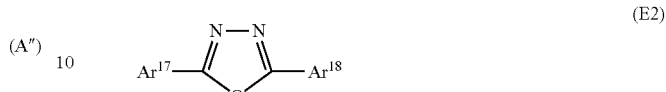

(E2)

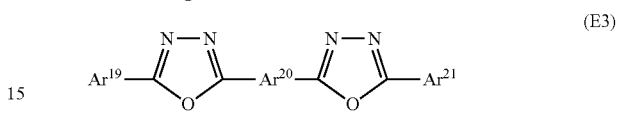

(E3)

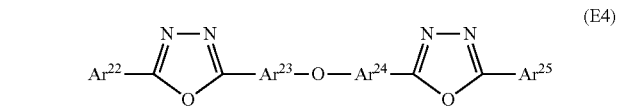

(E4)

In the formulas above, $Ar^{17}$, $Ar^{18}$, $Ar^{19}$, $Ar^{21}$, $Ar^{22}$ and $Ar^{25}$ each represent a substituted or unsubstituted aromatic hydrocarbon group or fused aromatic hydrocarbon group having 6 to 40 ring carbon atoms. $Ar^{17}$, $Ar^{19}$ and $Ar^{22}$ may be the same as or different from $Ar^{18}$, $Ar^{21}$ and $Ar^{25}$ respectively. Examples of the aromatic hydrocarbon group or fused aromatic hydrocarbon group having 6 to 40 ring carbon atoms are a phenyl group, biphenyl group, anthranil group, perylenyl group and pyrenyl group. Examples of the substituent therefor are an alkyl group having 1 to 10 carbon atoms, alkoxy group having 1 to 10 carbon atoms and cyano group.

$Ar^{20}$, $Ar^{23}$ and $Ar^{24}$ each represent a substituted or, unsubstituted divalent aromatic hydrocarbon group or fused aromatic hydrocarbon group having 6 to 40 ring carbon atoms. $Ar^{23}$ and $Ar^{24}$ may be mutually the same or different. Examples of the divalent aromatic hydrocarbon group or fused aromatic hydrocarbon group having 6 to 40 ring carbon atoms are a phenylene group, naphthylene group, biphenylene group, anthranylene group, perylenylene group and pyrenylene group. Examples of the substituent therefor are an alkyl group having 1 to 10 carbon atoms, alkoxy group having 1 to 10 carbon atoms and cyano group.

Preferably, such electron transport compound can be favorably formed into a thin film(s). Some examples of the electron transporting compounds are as follows.

(E5)

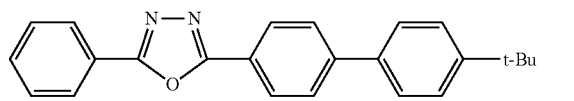
(E6)

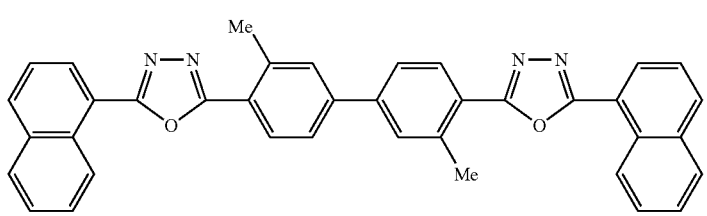
(E7)

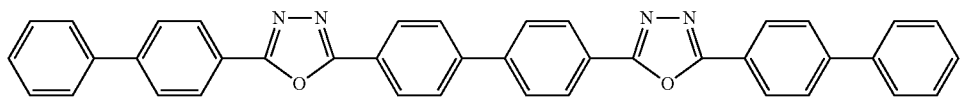
(E8)

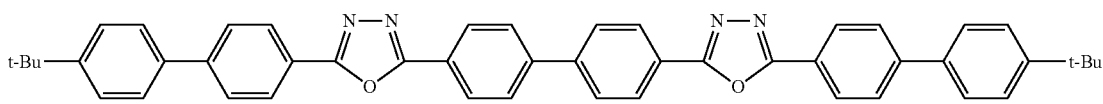
(E9)

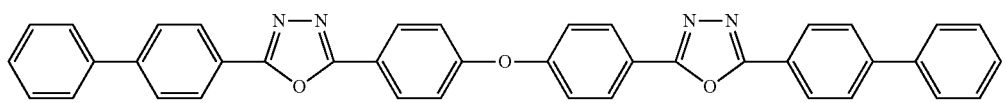
(E10)

An example of the nitrogen-containing heterocyclic derivative as the electron transporting compound is a nitrogen-containing compound that is not a metal complex, the derivative being formed of an organic compound represented by one of the following general formulae. Examples of the nitrogen-containing heterocyclic derivative are a five-membered ring or six-membered ring derivative having a skeleton represented by the following formula AA and a derivative having a structure represented by the following formula BB.

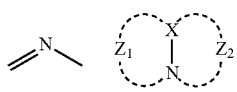

In the formula BB above, X represents a carbon atom or a nitrogen atom. $Z_1$ and $Z_2$ each independently represent a group of atoms capable of forming a nitrogen-containing heterocycle.

Preferably, the nitrogen-containing heterocyclic derivative is an organic compound having a nitrogen-containing aromatic polycyclic group having a five-membered ring or six-membered ring. When the nitrogen-containing heterocyclic derivative includes such nitrogen-containing aromatic polycyclic series having plural nitrogen atoms, the nitrogen-containing heterocyclic derivative may be a nitrogen-containing aromatic polycyclic organic compound having a skeleton formed by a combination of the skeletons respectively represented by the formulas AA and BB, or by a combination of the skeletons respectively represented by the formulas AA and CC.

A nitrogen-containing group of the nitrogen-containing aromatic polycyclic organic compound is selected from nitrogen-containing heterocyclic groups respectively represented by the following general formulas:

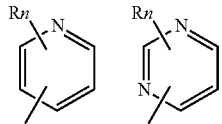

-continued

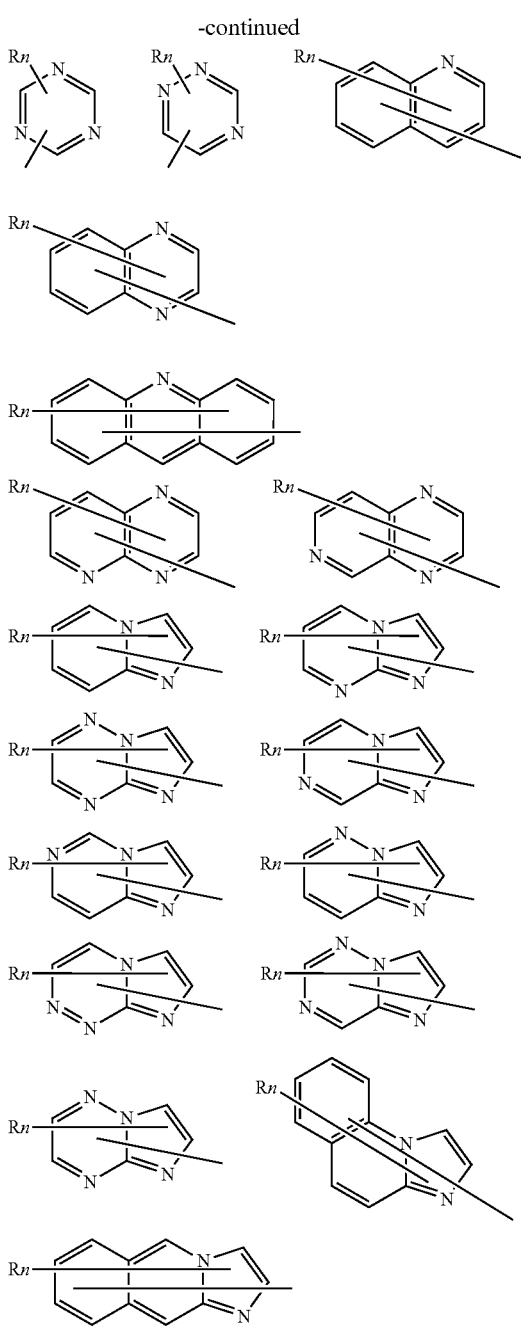

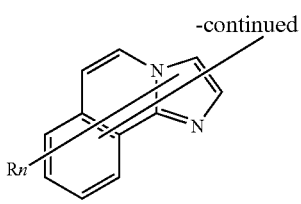

where, R represents an aromatic hydrocarbon group or fused aromatic hydrocarbon group having 6 to 40 ring carbon atoms, an aromatic heterocyclic group or fused aromatic heterocyclic group having 2 to 40 ring carbon atoms, an alkyl group having 1 to 20 carbon atoms or alkoxy group having 1 to 20 carbon atoms, and n represents an integer in a range of 0 to 5. When n is an integer of 2 or more, plural R may be mutually the same or different.

An example of a preferable specific compound is a nitrogen-containing heterocyclic derivative represented by the following formula:

$$HAr\text{-}L^1\text{-}Ar^1\text{—}Ar^2$$

Where, HAr represents a substituted or unsubstituted nitrogen-containing heterocyclic group having 1 to 40 ring carbon atoms, $L^1$ represents a single bond, substituted or unsubstituted aromatic hydrocarbon group or fused aromatic hydrocarbon group having 6 to 40 ring carbon atoms, or substituted or unsubstituted aromatic heterocyclic group or fused aromatic heterocyclic group having 2 to 40 ring carbon atoms, $Ar^1$ represents a substituted or unsubstituted divalent aromatic hydrocarbon group having 6 to 40 ring carbon atoms; and $Ar^2$ represents a substituted or unsubstituted aromatic hydrocarbon group or fused aromatic hydrocarbon group having 6 to 40 ring carbon atoms, or substituted or unsubstituted aromatic heterocyclic group or fused aromatic heterocyclic group having 2 to 40 ring carbon atoms.

Some examples of HAr can be selected from the following group:

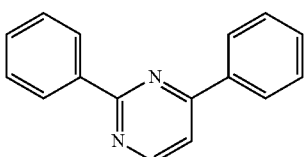

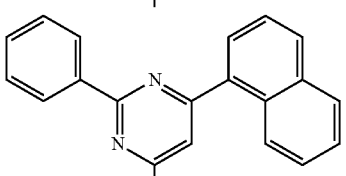

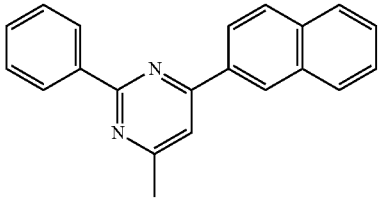

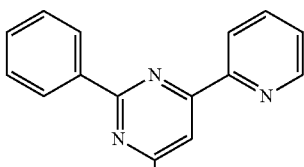

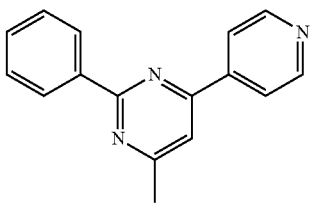

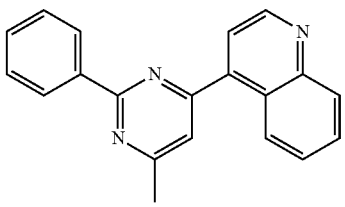

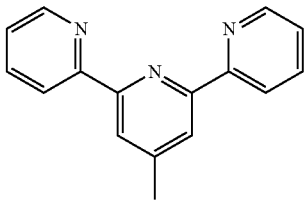

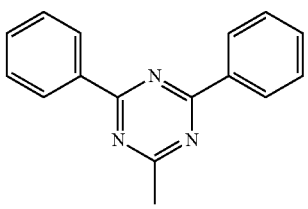

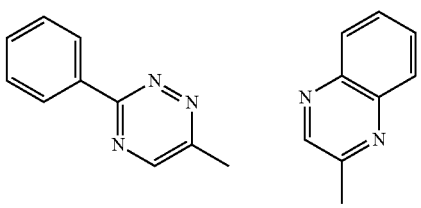

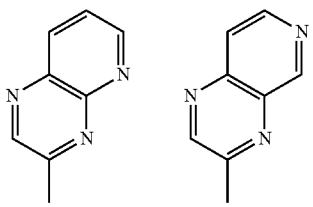

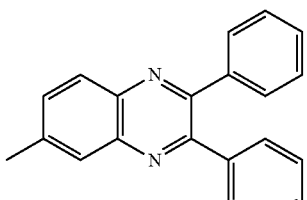

-continued

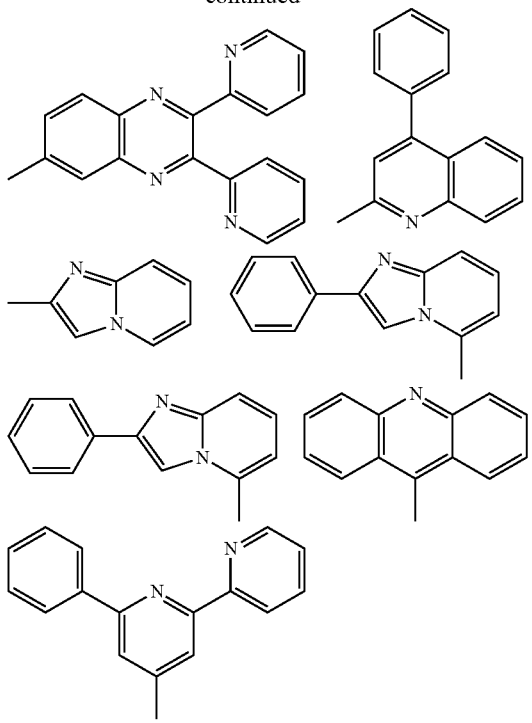

Some examples of $L^1$ can be selected from the following group:

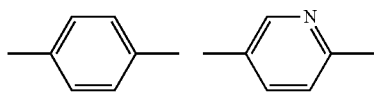

Some examples of $Ar^1$ can be selected from the following group:

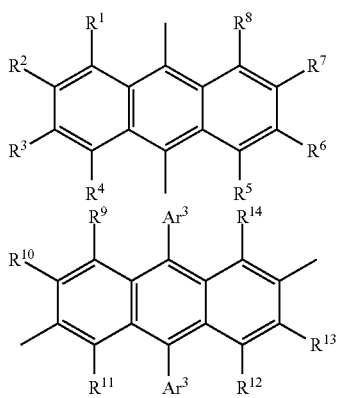

where, $R^1$ to $R^{14}$ each independently represent a hydrogen atom, halogen atom, alkyl group having 1 to 20 carbon atoms, alkoxy group having 1 to 20 carbon atoms, aryloxy group having 6 to 40 ring carbon atoms, substituted or unsubstituted aromatic hydrocarbon group or fused aromatic hydrocarbon group having 6 to 40 ring carbon atoms, or aromatic heterocyclic group or fused aromatic heterocyclic group having 2 to 40 ring carbon atoms; and $Ar^3$ represents aromatic hydrocarbon group or fused aromatic hydrocarbon group having 6 to 40 ring carbon atoms, or aromatic heterocyclic group or fused aromatic heterocyclic group having 2 to 40 ring carbon atoms.

All of $R^1$ to $R^8$ of a nitrogen-containing heterocyclic derivative may be hydrogen atoms.

Examples of $Ar^2$ can be selected from the following group:

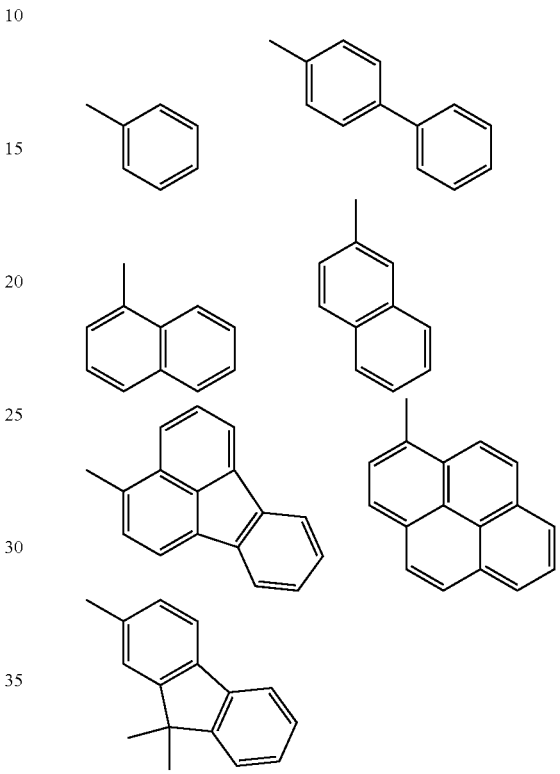

In addition to the above examples, the following nitrogen-containing aromatic polycyclic organic compound (see JP-A-9-3448) can be favorably used as the electron transporting compound.

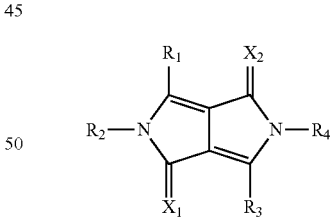

where, $R_1$ to $R_4$ each independently represent a hydrogen atom, substituted or unsubstituted aliphatic group, substituted or unsubstituted alicyclic group, substituted or unsubstituted carbocyclic aromatic cyclic group or substituted or unsubstituted heterocyclic group; and $X_1$ and $X_2$ each independently represent an oxygen atom, sulfur atom or dicyanomethylene group.

Additional examples of compounds that can be used as electron transporting material can be found in JP-A-2000-173774.

The electron injecting layer preferably contains an inorganic compound such as an insulator or a semiconductor in addition to the nitrogen-containing cyclic derivative. Such an insulator or a semiconductor, when contained in the electron injecting layer, can effectively prevent a current leak, thereby enhancing electron capability of the electron injecting layer.

As the insulator, it is preferable to use at least one metal compound selected from the group consisting of an alkali metal chalcogenide, an alkali earth metal chalcogenide, a halogenide of alkali metal and a halogenide of alkali earth metal. By forming the electron injecting layer from the alkali metal chalcogenide or the like, the electron injecting capability can preferably be further enhanced. Specifically, preferred examples of the alkali metal chalcogenide are $Li_2O$, $K_2O$, $Na_2S$, $Na_2Se$ and $Na_2O$, while preferable example of the alkali earth metal chalcogenide are CaO, BaO, SrO, BeO, BaS and CaSe. Preferred examples of the halogenide of the alkali metal are LiF, NaF, KF, LiCl, KCl and NaCl. Preferred examples of the halogenide of the alkali earth metal are fluorides such as $CaF_2$, $BaF_2$, $SrF_2$, $MgF_2$ and $BeF_2$, and halogenides other than the fluoride.

Examples of the semiconductor are one of or a combination of two or more of an oxide, a nitride or an oxidized nitride containing at least one element selected from Ba, Ca, Sr, Yb, Al, Ga, In, Li, Na, Cd, Mg, Si, Ta, Sb and Zn. An inorganic compound for forming the electron injecting layer is preferably a microcrystalline or amorphous semiconductor film. When the electron injecting layer is formed of such insulator film, more uniform thin film can be formed, thereby reducing pixel defects such as a dark spot. Examples of such an inorganic compound are the above-described alkali metal chalcogenide, alkali earth metal chalcogenide, halogenide of the alkali metal and halogenide of the alkali earth metal.

When the electron injecting layer contains such an insulator or such a semiconductor, a thickness thereof is preferably in a range of approximately 0.1 nm to 15 nm. The electron injecting layer in this exemplary embodiment may preferably contain the above-described reduction-causing dopant.

[HIL/HTL]

The hole injecting layer or the hole transporting layer (including the hole injecting/transporting layer) may contain an aromatic amine compound such as an aromatic amine derivative represented by the following general formula (I).

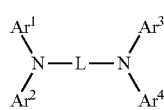

(I)

where, $Ar^1$ to $Ar^4$ each represent a substituted or unsubstituted aromatic hydrocarbon group or fused aromatic hydrocarbon group having 6 to 50 ring carbon atoms, substituted or unsubstituted aromatic heterocyclic group or fused aromatic heterocyclic group having 2 to 40 ring carbon atoms, or a group formed by combining the aromatic hydrocarbon group or the fused aromatic hydrocarbon group with the aromatic heterocyclic group or fused aromatic heterocyclic group.

Some examples of the compound represented by the general formula (I) can be found, for example, in United States Patent Application Publication No. US 2011/0278555 A1, the disclosures of which is incorporated herein by reference. However, the compound represented by the general formula (I) is not limited thereto.

Aromatic amine represented by the following formula (II) can also be used for forming the hole injecting layer or the hole transporting layer.

(II)

where, $Ar^1$ to $Ar^3$ each represent the same as $Ar^1$ to $Ar^4$ of the formula (I) above. Some examples of the compound represented by the general formula (II) can be found, for example, in United States Patent Application Publication No. US 2011/0278555 A1, the disclosures of which is incorporated herein by reference. However, the compound represented by the general formula (II) is not limited thereto.

A method of forming each of the layers in the organic EL device of the various embodiments described herein is not particularly limited. A conventionally-known methods such as vacuum deposition or spin coating may be employed for forming the layers. The organic thin-film layer containing the compound represented by the formula (1A) or (1B), which is used in the organic EL device according to this exemplary embodiment, may be formed by a conventional coating method such as vacuum deposition, molecular beam epitaxy (MBE method) and coating methods using a solution such as a dipping, spin coating, casting, bar coating, and roll coating.

Although the thickness of each organic layer of the organic EL device according to this exemplary embodiment is not particularly limited, the thickness is generally preferably in a range of several nanometers to 1 µm because an excessively-thinned film likely entails defects such as a pin hole while an excessively-thickened film requires high voltage to be applied and deteriorates efficiency.

In an OLED embodiment according to the present disclosure, a plurality of organic thin film layers provided between a cathode and an anode; the plurality of organic thin film layers comprise at least one phosphorescence emitting layer comprising at least one phosphorescent material and at least one biscarbazole derivative host material as described below.

As described above, a phosphorescence emitting layer having high efficiency and long lifetime can be prepared according to the teachings of the present invention, especially a high stability at high operating temperatures.

In this regard, an excited triplet energy gap Eg(T) of the material constituting the OLED of the present disclosure may be prescribed based on its phosphorescence emission spectrum, and it is given as an example in the present disclosure that the energy gap may be prescribed, as is commonly used, in the following manner.

The respective materials are dissolved in an EPA solvent (diethyl ether:isopentane:ethanol=5:5:2 in terms of a volume ratio) in a concentration of 10 µmol/L to prepare a sample for measuring phosphorescence. This phosphorescence measuring sample is placed in a quartz cell and cooled to 77 K, and is subsequently irradiated with exciting light to measure the wavelength of a phosphorescence emitted.

A tangent line is drawn based on the increase of phosphorescence emission spectrum thus obtained at the short wavelength side, and the wavelength value of the intersection point of the above tangent line and the base line is converted to an energy value, which is set as an excited triplet energy gap Eg(T). A commercially available measuring equipment F-4500 (manufactured by Hitachi, Ltd.) can be used for the measurement.

However, a value which can be defined as the triplet energy gap can be used without depending on the above procedure as long as it does not deviate from the scope of the present invention.

[Light Emitting Layer According to Second Embodiment]

According to another embodiment, an organic EL device comprises a cathode, an anode, and a plurality of organic thin-film layers provided between the cathode and the anode and at least one of the plurality of organic thin-film layers comprise an emitting layer comprising a first host material, a second host material, and a green phosphorescent dopant material as emitter. The first host material of the pair of co-host materials is a biscarbazole derivative compound represented by formula (1A) or (1B) as described.

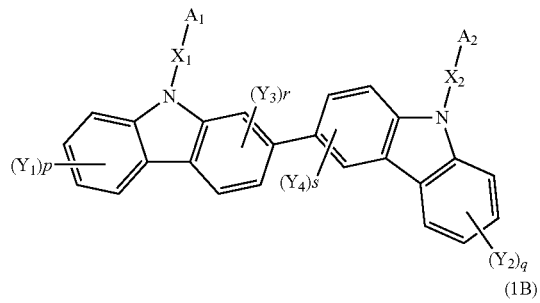
(1A)

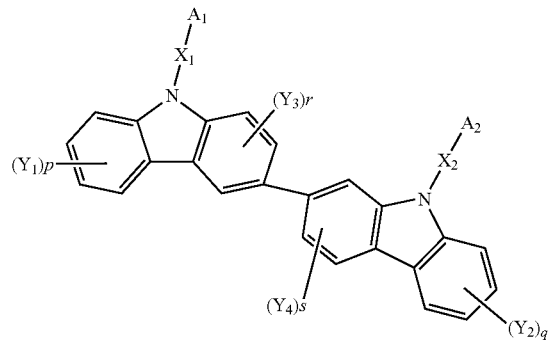
(1B)

A second host material of the pair of co-host materials is a biscarbazole derivative compound represented by a formula (1A'), (1B') or (2) below:

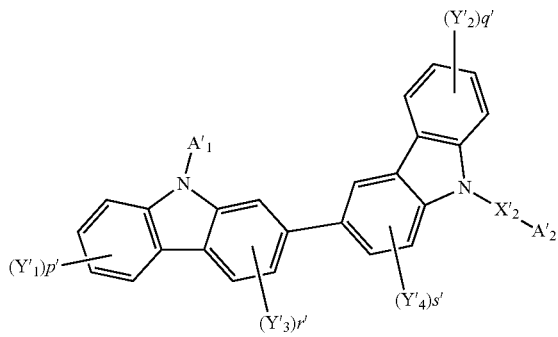
(1A')

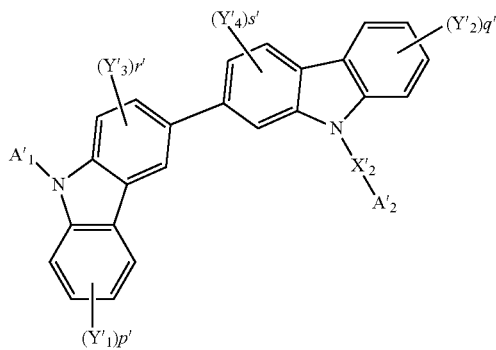
(1B')

wherein $A_1'$ represents a substituted or unsubstituted nitrogen-containing heterocyclic group having 1 to 30 carbon atoms forming a ring;

$A_2'$ represents a substituted or unsubstituted aromatic hydrocarbon group having 6 to 30 ring carbon atoms, or substituted or unsubstituted nitrogen-containing heterocyclic group having 1 to 30 ring carbon atoms;

$X_2'$ is a linking group and independently represent, a single bond, substituted or unsubstituted aromatic hydrocarbon group having 6 to 30 ring carbon atoms, substituted or unsubstituted fused aromatic hydrocarbon group having 6 to 30 ring carbon atoms, substituted or unsubstituted aromatic heterocyclic group having 2 to 30 ring carbon atoms, or substituted or unsubstituted fused aromatic heterocyclic group having 2 to 30 ring carbon atoms;

$Y_1'$ to $Y_4'$ independently represent a hydrogen atom, fluorine atom, cyano group, substituted or unsubstituted alkyl group having 1 to 20 carbon atoms, substituted or unsubstituted alkoxy group having 1 to 20 carbon atoms, substituted or unsubstituted haloalkyl group having 1 to 20 carbon atoms, substituted or unsubstituted haloalkoxy group having 1 to 20 carbon atoms, substituted or unsubstituted alkylsilyl having 1 to 10 carbon atoms, substituted or unsubstituted arylsilyl having 6 to 30 carbon atoms, substituted or unsubstituted aromatic hydrocarbon group having 6 to 30 ring carbon atoms, substituted or unsubstituted fused aromatic hydrocarbon group having 6 to 30 ring carbon atoms, substituted or unsubstituted aromatic heterocyclic group having 2 to 30 ring carbon atoms, or substituted or unsubstituted fused aromatic heterocyclic group having 2 to 30 ring carbon atoms;

adjacent ones of $Y_1'$ to $Y_4'$ are allowed to be bonded to each other to form a ring structure;

p' and q' represent an integer of 1 to 4; r' and s' represent an integer of 1 to 3; and when p' and q' are an integer of 2 to 4 and r' and s' are an integer of 2 to 3, a plurality of $Y_1'$ to $Y_4'$ are allowed to be the same or different;

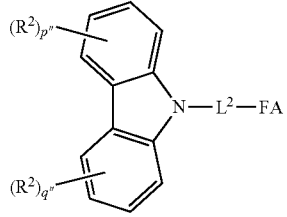
(2)

where $R^2$ independently represents a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 6 to 30 ring carbon atoms, or a substituted or unsubstituted aryloxy group having 6 to 30 ring carbon atoms;

p" and q" are independently an integer of 0 to 4;

a plurality of $R^2$ are mutually the same or different;

adjacent groups of $R^2$ are allowed to bond with each other to form a ring;

$L^2$ represents a single bond or a linking group, the linking group being one or a combination of a substituted or unsubstituted aryl group having 6 to 30 ring carbon atoms, a substituted or unsubstituted heterocyclic group having 5 to 30 ring atoms, and a cycloalkyl group having 5 to 30 ring carbon atoms; and FA represents a substituted or unsubstituted fused aromatic cyclic group having 6 to 30 ring carbon atoms, or a substituted or unsubstituted fused aromatic heterocyclic group having 5 to 30 ring atoms. Examples of FA in the second host material represented by formula (2) are represented by any one of the formulas (2-1) to (2-4):

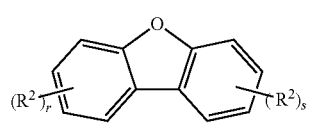
(2-1)

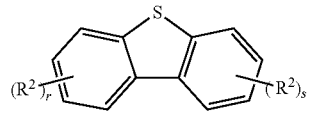
(2-2)

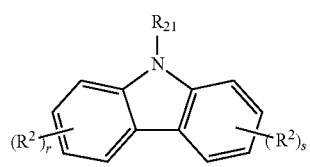
(2-3)

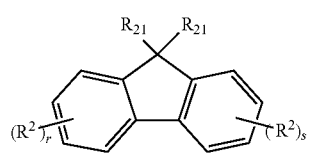
(2-4)

where $R^2$ and $R^{21}$ represent the same as $R^2$ of the formula (2);

one of $R^2$ is a single bond to bond with $L^2$ in the formula (2); and r and s are an integer of 0 to 4.

In the organic EL device of the present embodiment, the second host material represented by a formula (1A') or (1B') can be a compound represented by the following formula (2H) below:

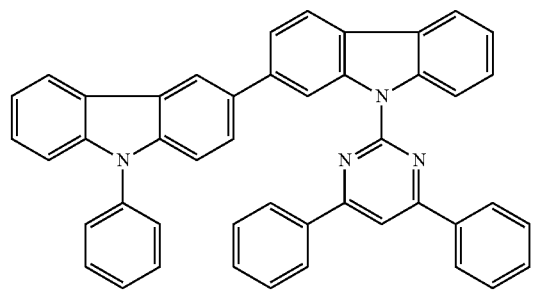 [SMILES: c1ccc(-c2cc(-c3ccccc3)nc(-n3c4ccccc4c4ccc(-c5ccc6c(c5)c5ccccc5n6-c5ccccc5)cc43)n2)cc1]

Examples of a biscarbazole derivative compound as the second host material represented by the formula (2) are described below as chemical formula 260. An example of such a material can be a compound represented by the following formula (3H) below:

(3H)

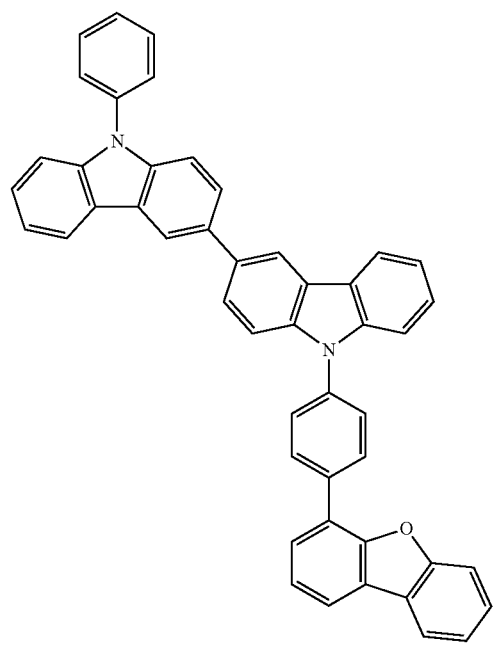

The green phosphorescent dopant material as emitter is an organometallic complex having a chemical structure represented by

LL'L"M where M is a metal that forms octahedral complexes, L, L', and L" are equivalent or inequivalent bidentate ligands wherein each L comprises a substituted or unsubstituted phenylpyridine ligand coordinated to M through an sp² hybridized carbon and N; and, one of L, L' and L" is different from at least one of the other two. The ligand L, L', and L" are coordinated to the metal M having atomic number greater than 40. Preferably, the metal M is Ir. Examples of the green phosphorescent dopant material may be an organometallic compound having a substituted chemical structure represented by the formula (4A) as described above.

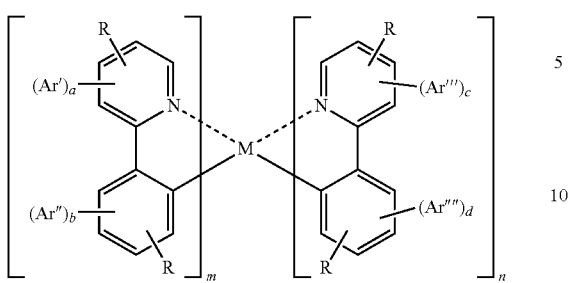

(4A)

In the organic EL device of the present embodiment, the phosphorescent material can be an organometallic compound represented by the following formula (4B) below:

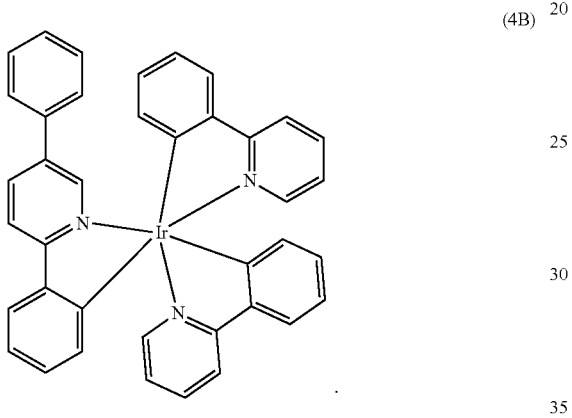

(4B)

According to another aspect of the present disclosure, in the devices of the present embodiment, the $A_1$ in the first host compound and/or the second host compound can represent a substituted or unsubstituted benzofuranyl group, a substituted or unsubstituted dibenzofuranyl group, a substituted or unsubstituted benzothiophenyl group, a substituted or unsubstituted dibenzothiophenyl group, a substituted or unsubstituted benzonaphthofuranyl group, or a substituted or unsubstituted benzonaphthothiophenyl group.

In the devices of the present embodiment, the first host material can be a compound represented by the formula 1H below:

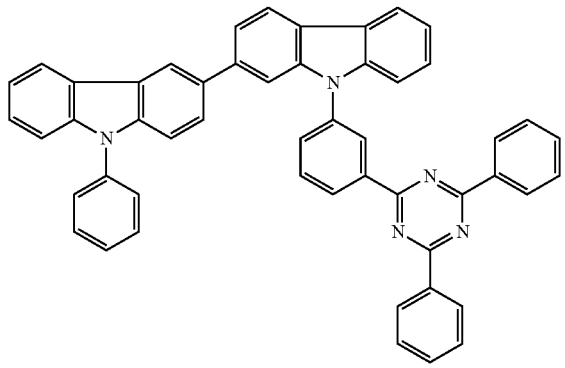

(1H)

In the devices of the present embodiment, the second host material can be a compound represented by the formula 2H or 3H below:

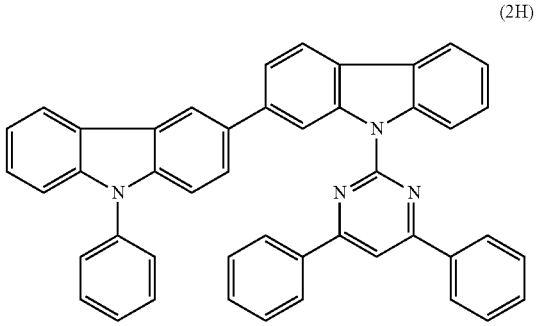

(2H)

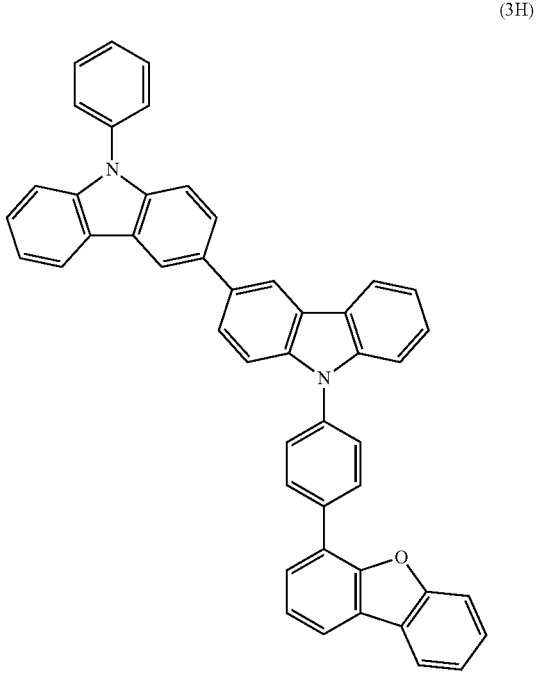 [SMILES: c1ccc(-n2c3ccccc3c3cc(-c4ccc5c(c4)c4ccccc4n5-c4ccc(-c5cccc6c5oc5ccccc56)cc4)ccc32)cc1]

(3H)

In the biscarbazole derivative compounds disclosed herein, when $Y_1$ to $Y_4$ are bonded to each other to form a ring structure, the ring structure is exemplified by structures represented by the following formulas:

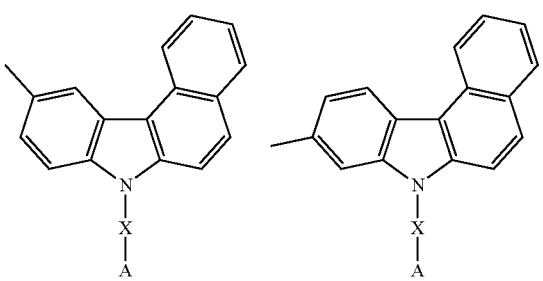

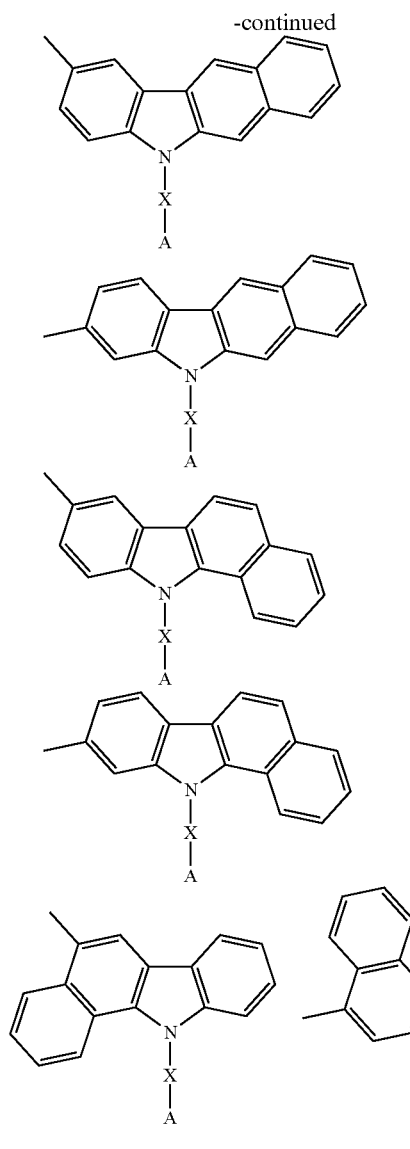

Moreover, $A_1$ in the formula (1A) or (1B) is preferably selected from the group consisting of a substituted or unsubstituted pyridine ring, substituted or unsubstituted pyrimidine ring and substituted or unsubstituted triazine ring, more preferably selected from a substituted or unsubstituted pyrimidine ring or substituted or unsubstituted triazine ring, and further preferably a substituted or unsubstituted pyrimidine ring.

Moreover, according to the above aspect, $A_1$ in the formula (1A) or (1B) is preferably a substituted or unsubstituted quinazoline ring.

In the formula (1A) or (1B) $X_1$ is preferably a single bond or substituted or unsubstituted divalent aromatic hydrocarbon group having 6 to 30 ring carbon atoms, particularly preferably a benzene ring.

In the formula (1A) or (1B) when $X_1$ is a substituted or unsubstituted benzene ring, $A_1$ and the carbazolyl group, which are bonded to $X_1$, are preferably in meta positions or para positions. Particularly preferably, $X_1$ is unsubstituted para-phenylene.

In the formula (1A) or (1B), the pyridine ring, pyrimidine ring and triazine ring are more preferably represented by the following formulas. In the formulas, Y and Y' represent a substituent. Examples of the substituent are the same groups as those represented by $Y_1$ to $Y_4$ as described above. Y and Y' may be the same or different. Preferred examples thereof are the substituted or unsubstituted aromatic hydrocarbon group or fused aromatic hydrocarbon group having 6 to 30 ring carbon atoms, and the substituted or unsubstituted aromatic heterocyclic group or fused aromatic heterocyclic group having 2 to 30 ring carbon atoms. In the following formulas, * represents a bonding position to $X_1$ or $X_2$.

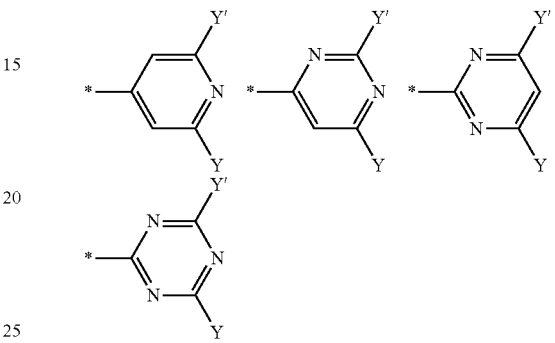

In the formula (1A) or (1B), the quinazoline ring is represented by the following formula. Y represents a substituent. u represents an integer of 1 to 5. When u is an integer of 2 to 5, a plurality of Y may be the same or different. As the substituent Y, the same groups as those for the above $Y_1$ to $Y_4$ are usable, among which preferred examples thereof are the substituted or unsubstituted aromatic hydrocarbon group or fused aromatic hydrocarbon group having 6 to 30 ring carbon atoms, and the substituted or unsubstituted aromatic heterocyclic group or fused aromatic heterocyclic group having 2 to 30 ring carbon atoms. Also in the following formulas, * represents a bonding position to $X_1$ or $X_2$.

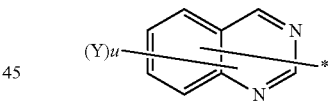

In the formulae (1A) to (1B), the alkyl group, alkoxy group, haloalkyl group, haloalkoxy group and alkylsilyl group, which are represented by $Y_1$ to $Y_5$, may be linear, branched or cyclic.

In the formulae (1A) to (1B), some examples of the alkyl group having 1 to 20 carbon atoms are a methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neo-pentyl group, 1-methylpentyl group, 2-methylpentyl group, 1-pentylhexyl group, 1-butylpentyl group, 1-heptyloctyl group, 3-methylpentyl group, cyclopentyl group, cyclohexyl group, cycloheptyl group, cyclooctyl group and 3,5-tetramethylcyclohexyl group. An alkyl group having 1 to 10 carbon atoms is preferable, examples of which are a methyl group, ethyl group, propyl group, isopropyl group, n-butyl group, s-butyl group, isobutyl group, t-butyl group, cyclopentyl group, cyclohexyl group and cycloheptyl group.

As the alkoxy group having 1 to 20 carbon atoms, an alkoxy group having 1 to 6 carbon atoms is preferable and specific examples thereof are a methoxy group, ethoxy group, propoxy group, butoxy group, pentyloxy group, and hexyloxy group.

The haloalkyl group having 1 to 20 carbon atoms is exemplified by a haloalkyl group provided by substituting the alkyl group having 1 to 20 carbon atoms with one or more halogen atoms. Preferred one of the halogen atoms is fluorine. The haloalkyl group is exemplified by a trifluoromethyl group and a 2,2,2-trifluoroethyl group.

The haloalkoxy group having 1 to 20 carbon atoms is exemplified by a haloalkoxy group provided by substituting the alkoxy group having 1 to 20 carbon atoms with one or more halogen atoms. Preferred one of the halogen atoms is fluorine.

Some examples of the alkylsilyl group having 1 to 10 carbon atoms are a trimethylsilyl group, triethylsilyl group, tributylsilyl group, dimethylethylsilyl group, dimethylisopropylsilyl group, dimethylpropylsilyl group, dimethylbutylsilyl group, dimethyl-tertiary-butylsilyl group and diethylisopropylsilyl group.

Some examples of the arylsilyl group having 6 to 30 carbon atoms are a phenyldimethylsilyl group, diphenylmethylsilyl group, diphenyl-tertiary-butylsilyl group and triphenylsilyl group.

Some examples of the aromatic heterocyclic group or fused aromatic heterocyclic group having 2 to 30 ring carbon atoms are a pyroryl group, pyrazinyl group, pyridinyl group, indolyl group, isoindolyl group, furyl group, benzofuranyl group, isobenzofuranyl group, dibenzofuranyl group, dibenzothiophenyl group, quinolyl group, isoquinolyl group, quinoxalinyl group, carbazolyl group, phenantridinyl group, acridinyl group, phenanthrolinyl group, thienyl group and a group formed from a pyridine ring, pyrazine ring, pyrimidine ring, pyridazine ring, triazine ring, indol ring, quinoline ring, acridine ring, pirrolidine ring, dioxane ring, piperidine ring, morpholine ring, piperadine ring, carbazole ring, furan ring, thiophene ring, oxazole ring, oxadiazole ring, benzooxazole ring, thiazole ring, thiadiazole ring, benzothiazole ring, triazole ring, imidazole ring, benzoimidazole ring, pyrane ring and dibenzofuran ring. Among the above, the aromatic heterocyclic group or fused aromatic heterocyclic group having 2 to 10 ring carbon atoms is preferable.

Some examples of the aromatic hydrocarbon group or fused aromatic hydrocarbon group having 6 to 30 ring carbon atoms are a phenyl group, naphthyl group, phenanthryl group, biphenyl group, terphenyl group, quarterphenyl group, fluoranthenyl group, triphenylenyl group, phenanthrenyl group, pyrenyl group, chrysenyl group, fluorenyl group, and 9,9-dimethylfluorenyl group. Among the above, the aromatic hydrocarbon group or fused aromatic hydrocarbon group having 6 to 20 ring carbon atoms is preferable.

When $A_1$, $A_2$, $X_1$, $X_2$ and $Y_1$ to $Y_5$ in the formula (1A) or (1B) each have one or more substituents, the substituents are preferably a linear, branched or cyclic alkyl group having 1 to 20 carbon atoms; linear, branched or cyclic alkoxy group having 1 to 20 carbon atoms; linear, branched or cyclic haloalkyl group having 1 to 20 carbon atoms; linear, branched or cyclic alkylsilyl group having 1 to 10 carbon atoms; arylsilyl group having 6 to 30 ring carbon atoms; cyano group; halogen atom; aromatic hydrocarbon group or fused aromatic hydrocarbon group having 6 to 30 ring carbon atoms; or aromatic heterocyclic group or fused aromatic heterocyclic group having 2 to 30 ring carbon atoms.

Some examples of the linear, branched or cyclic alkyl group having 1 to 20 carbon atoms; linear, branched or cyclic alkoxy group having 1 to 20 carbon atoms; linear, branched or cyclic haloalkyl group having 1 to 20 carbon atoms; linear, branched or cyclic alkylsilyl group having 1 to 10 carbon atoms; arylsilyl group having 6 to 30 ring carbon atoms; aromatic hydrocarbon group or fused aromatic hydrocarbon group having 6 to 30 ring carbon atoms; and aromatic heterocyclic group or fused aromatic heterocyclic group having 2 to 30 ring carbon atoms are the above-described groups. The halogen atom is exemplified by a fluorine atom.

Examples of compounds for the biscarbazole derivative according to this exemplary embodiment represented by the formula (1A) or (1B) are as follows:

[Chemical formula 10]

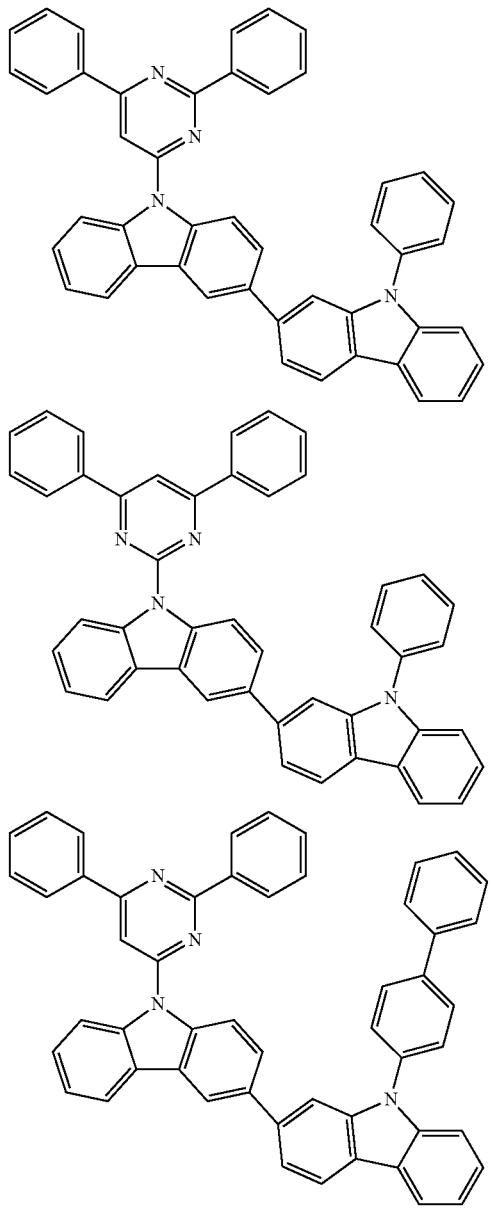

39
-continued
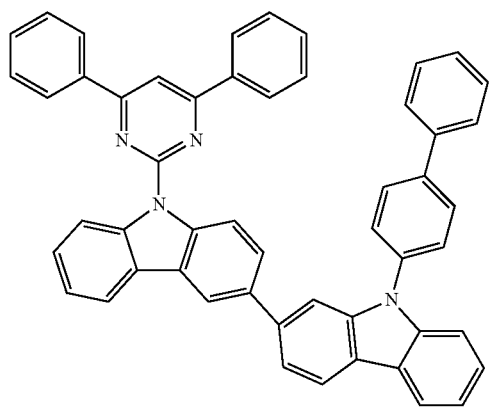
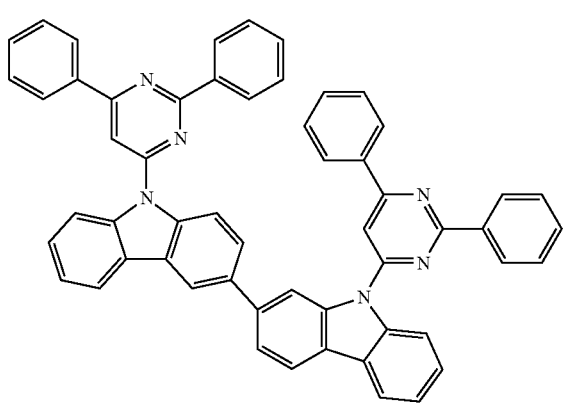
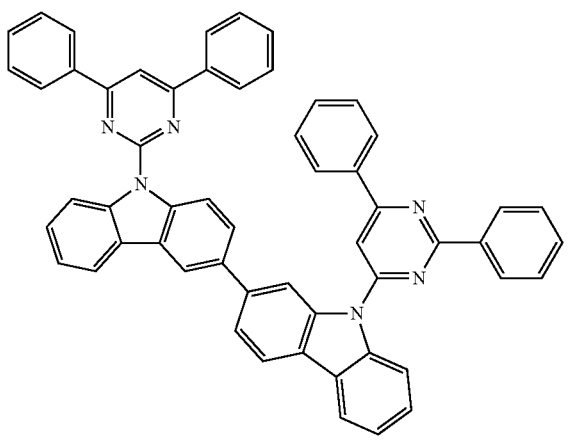
40
-continued
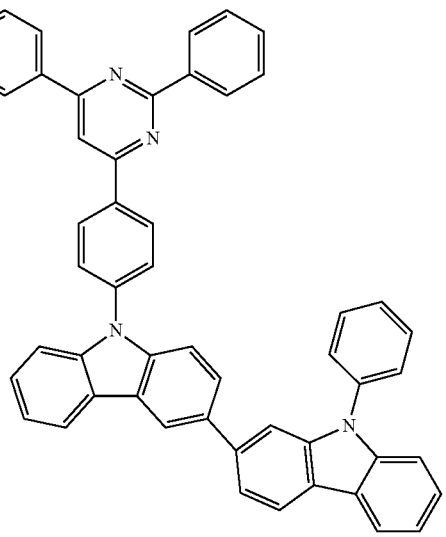
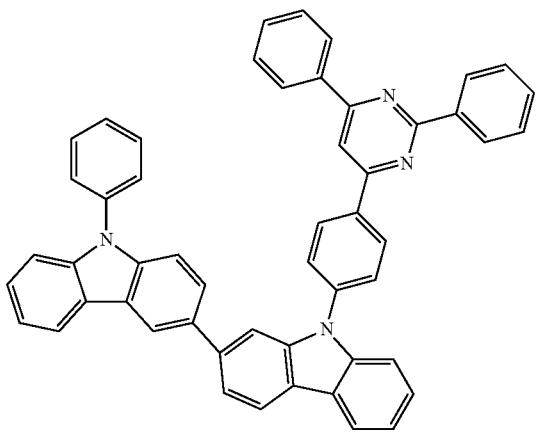

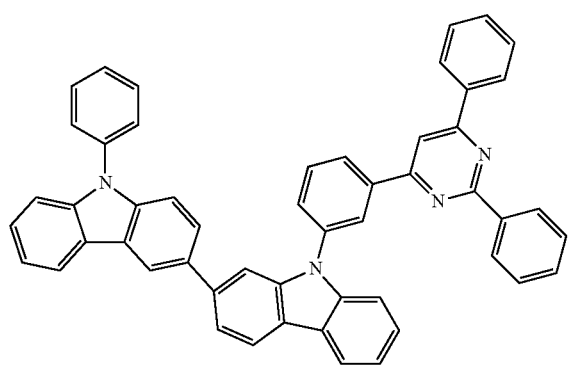
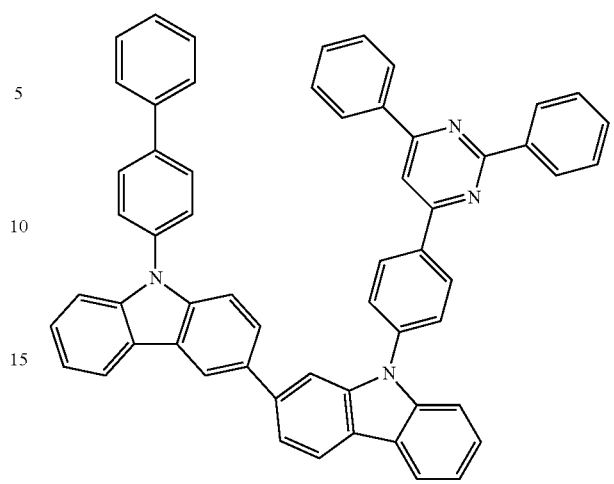
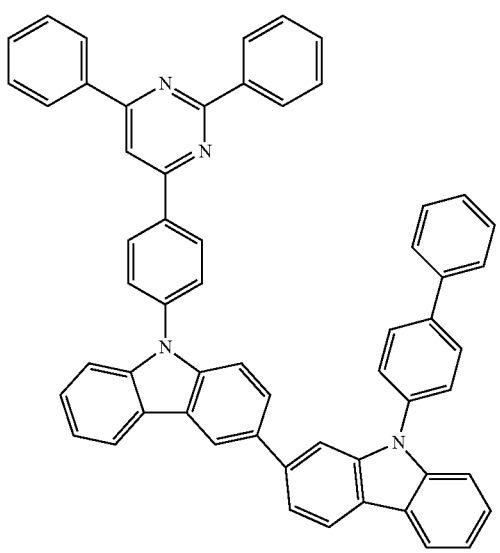
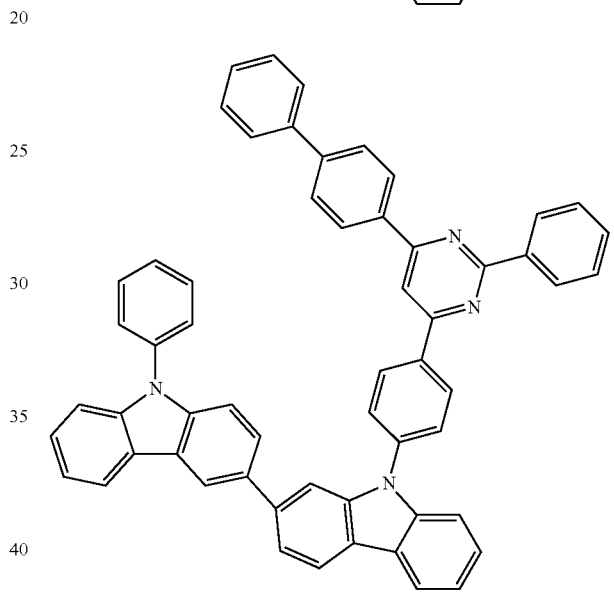
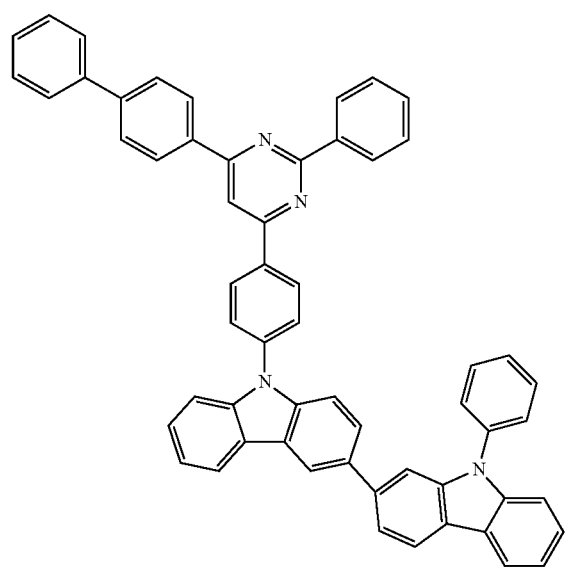
[Chemical formula 20]
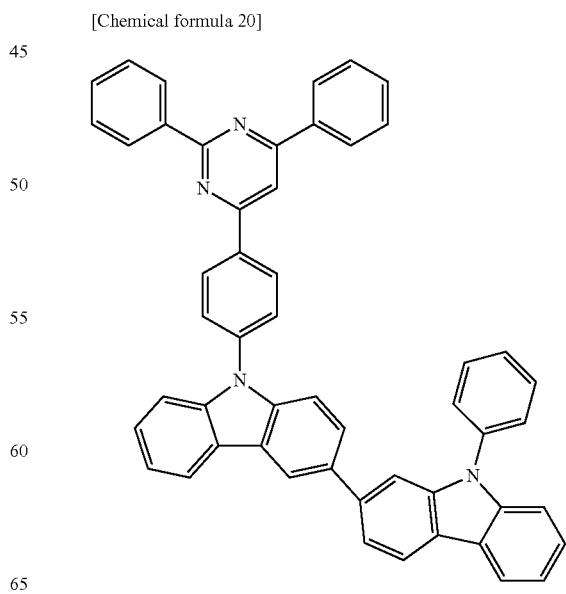

-continued
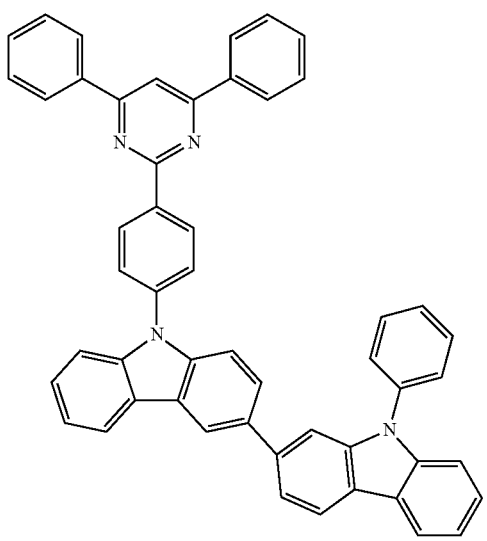
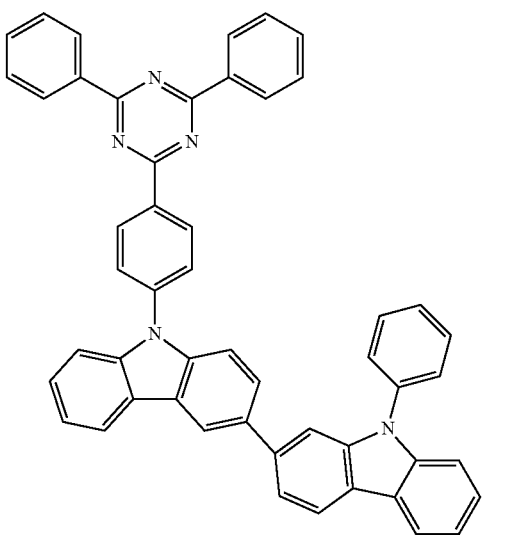
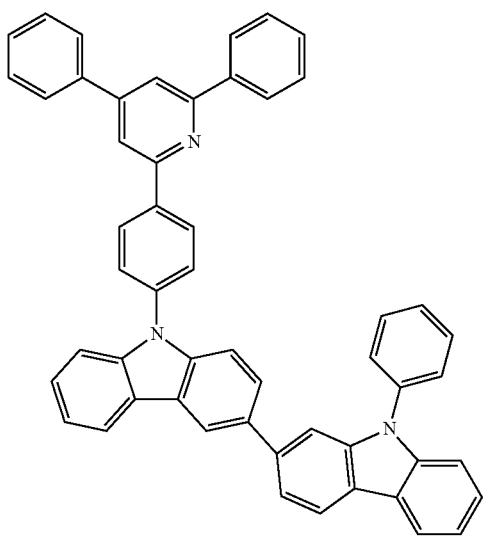
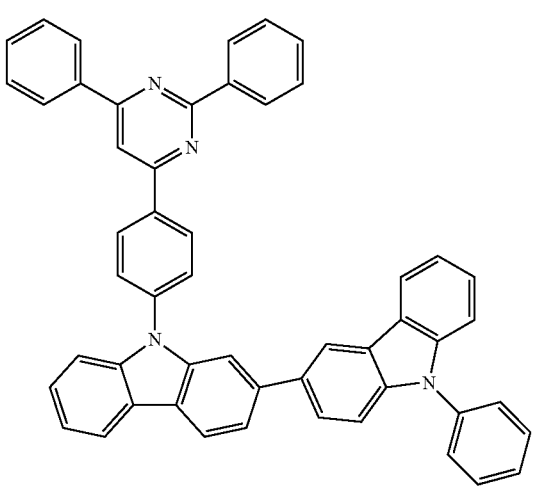
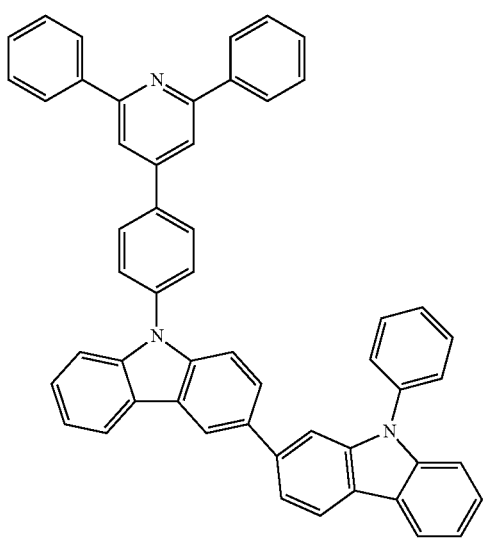
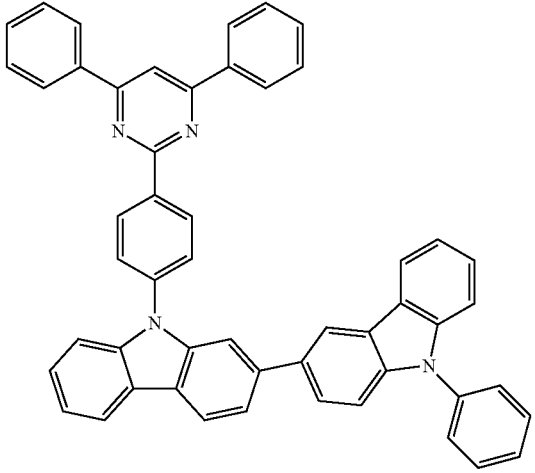 [SMILES: c1ccc(-c2nc(-c3ccccc3)nc(-c3ccc(-n4c5ccccc5c5ccc(-c6ccc7c(c6)c6ccccc6n7-c6ccccc6)cc54)cc3)n2)cc1]

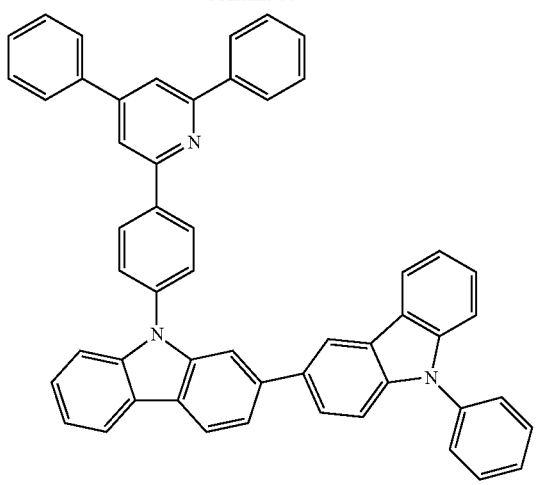
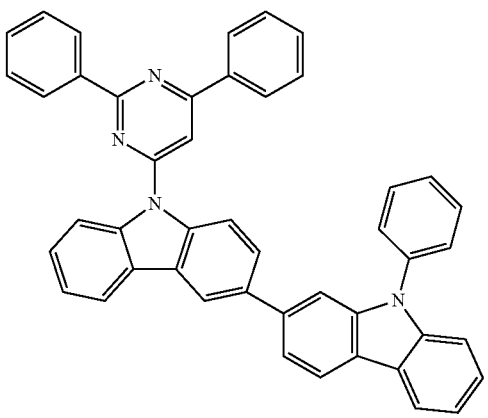
[Chemical formula 30]
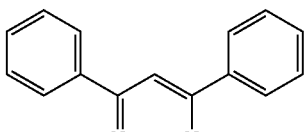
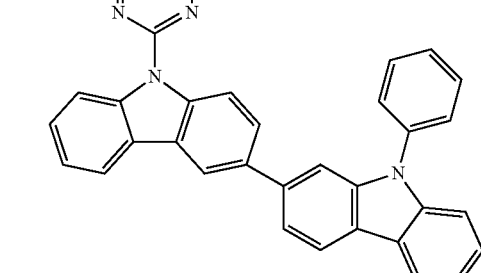
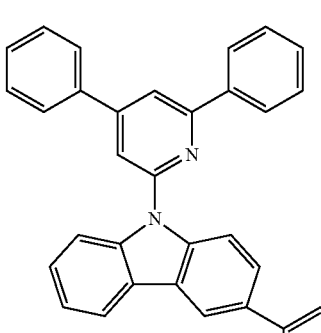
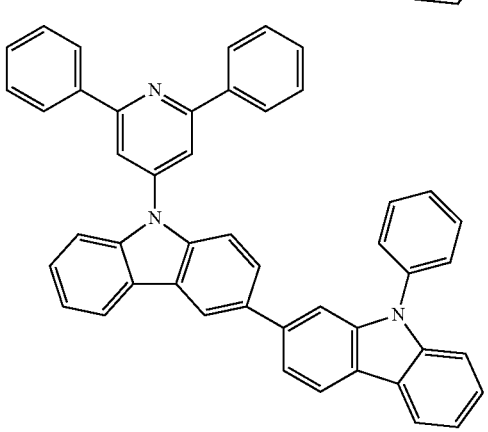

-continued
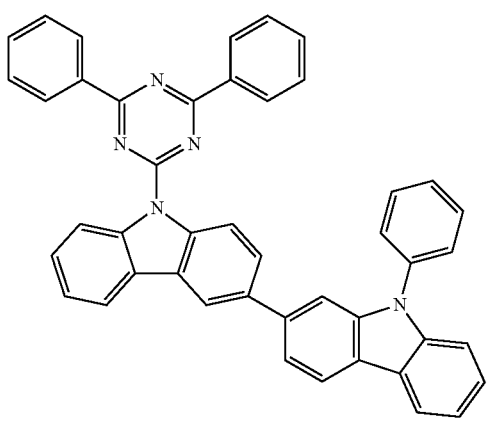
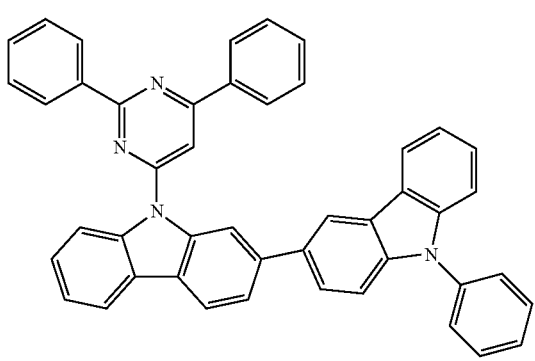
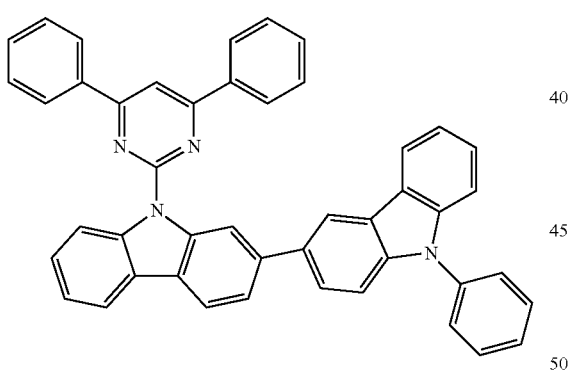
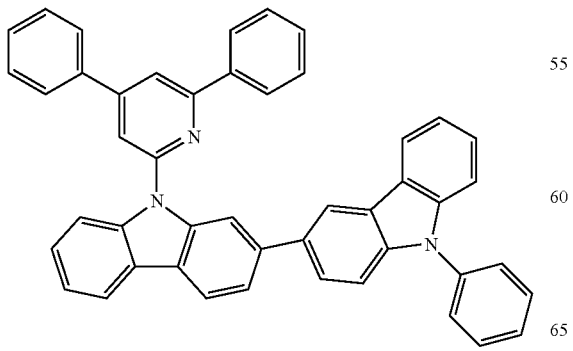
-continued
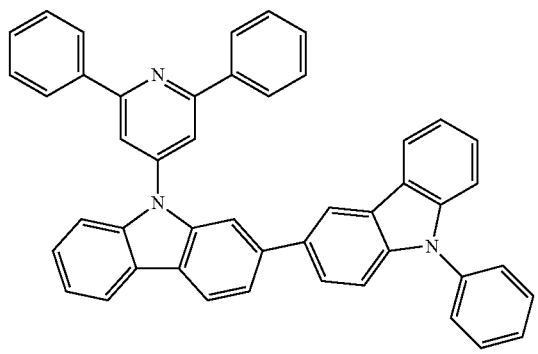
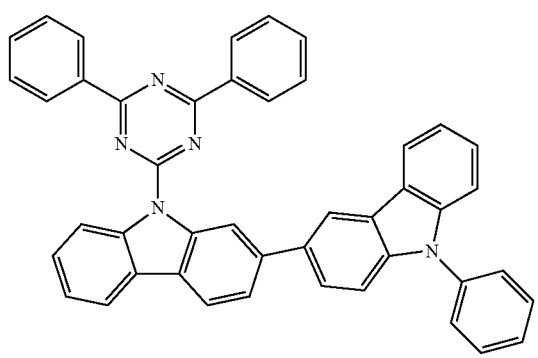
[Chemical formula 40]
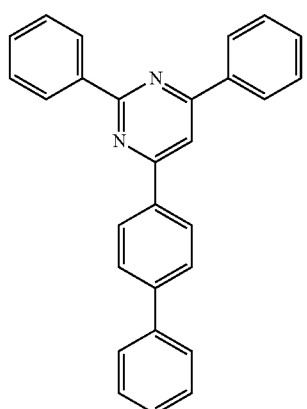
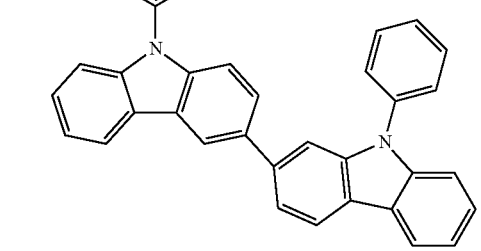

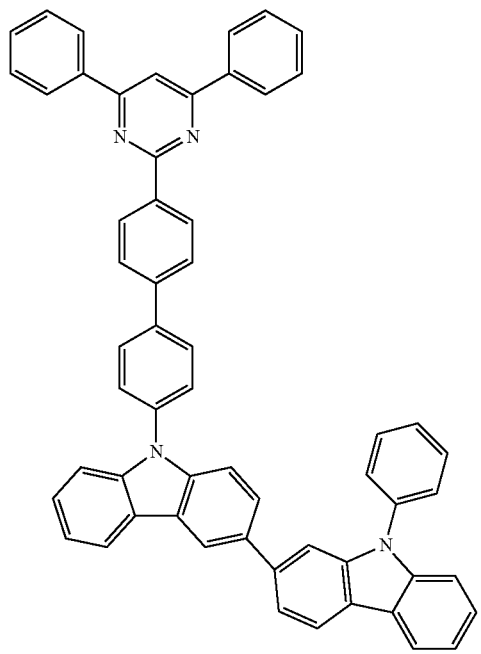
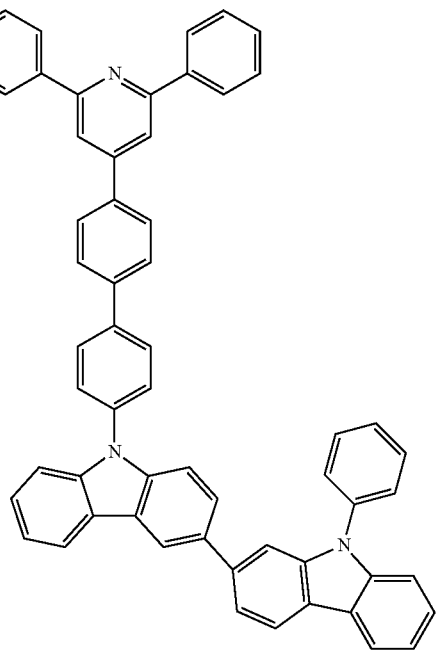
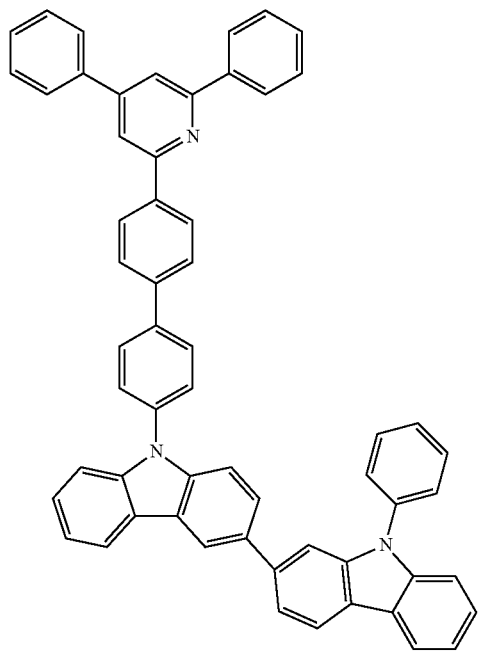
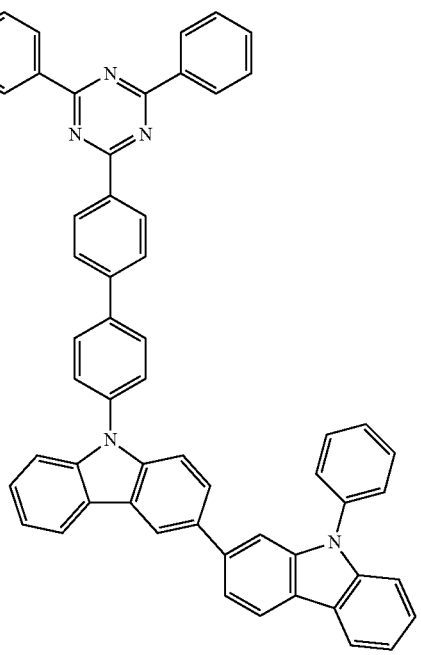

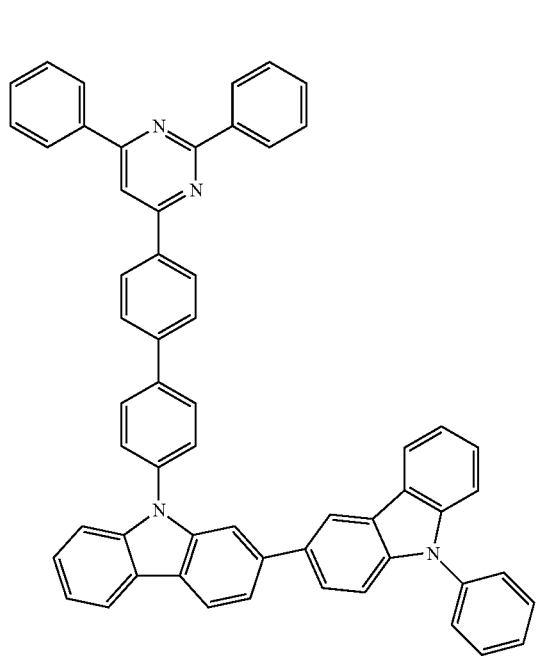
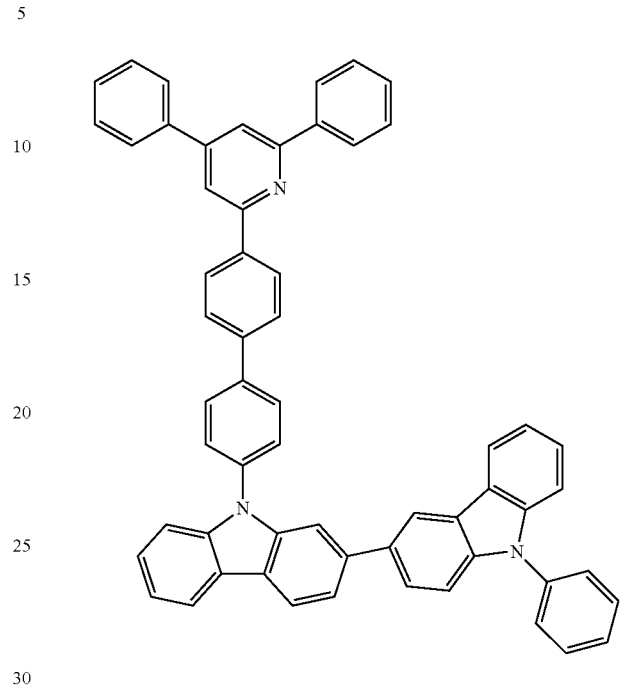
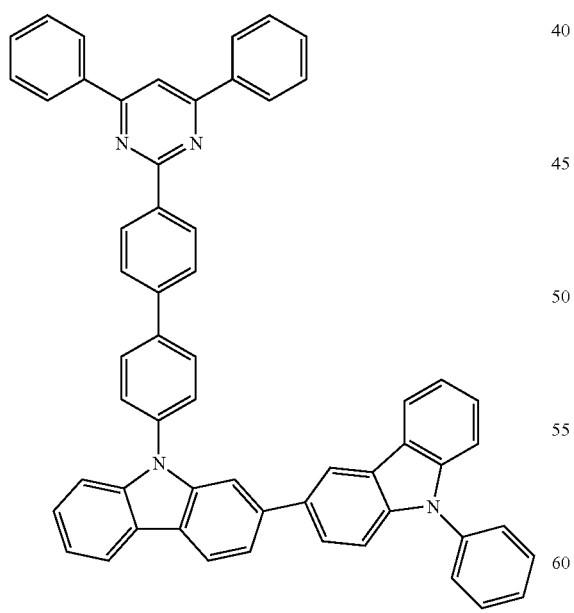
[Chemical formula 50]
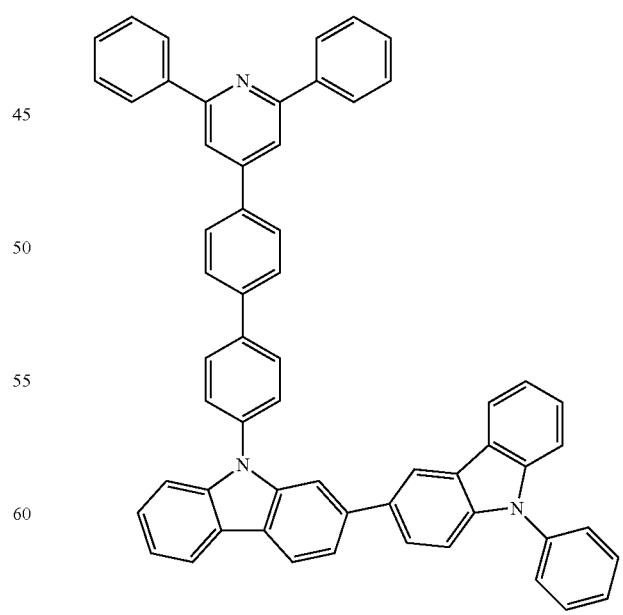

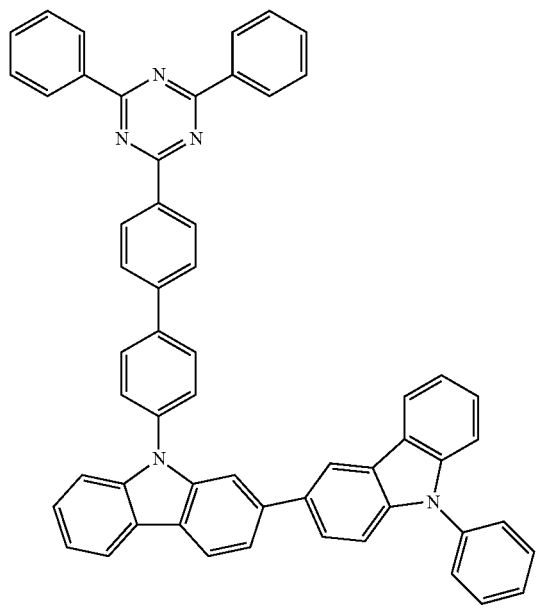
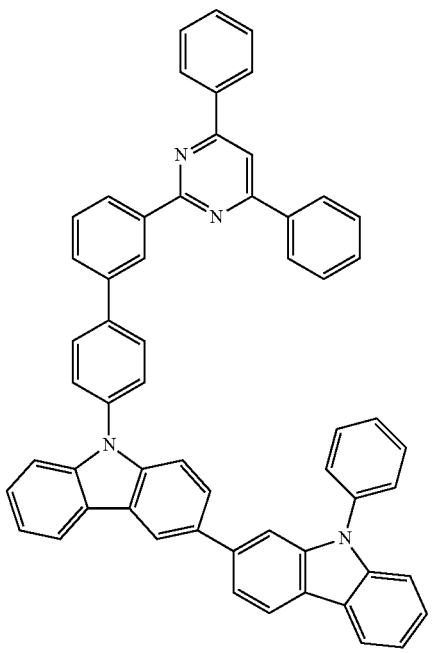
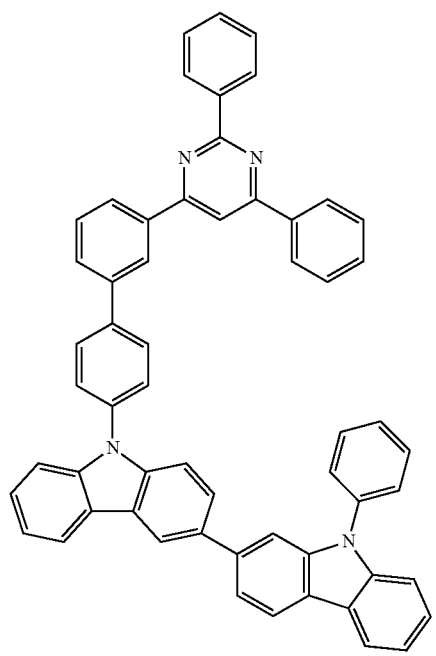
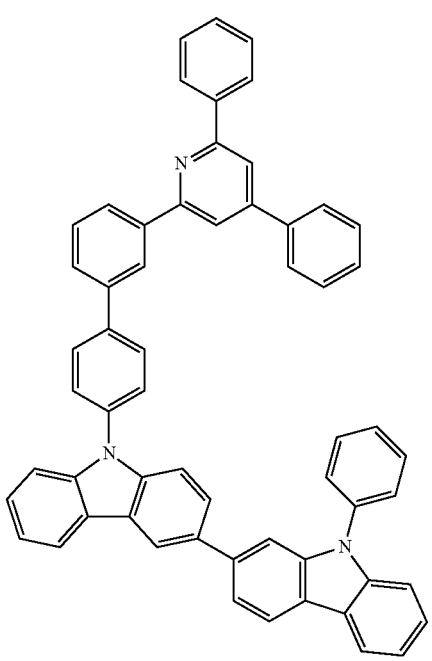

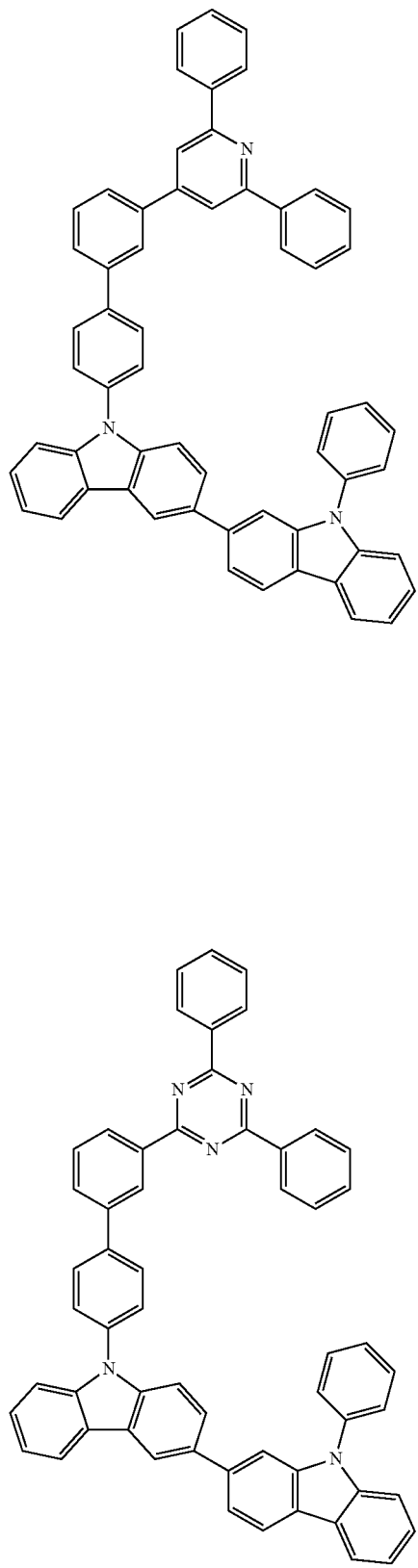
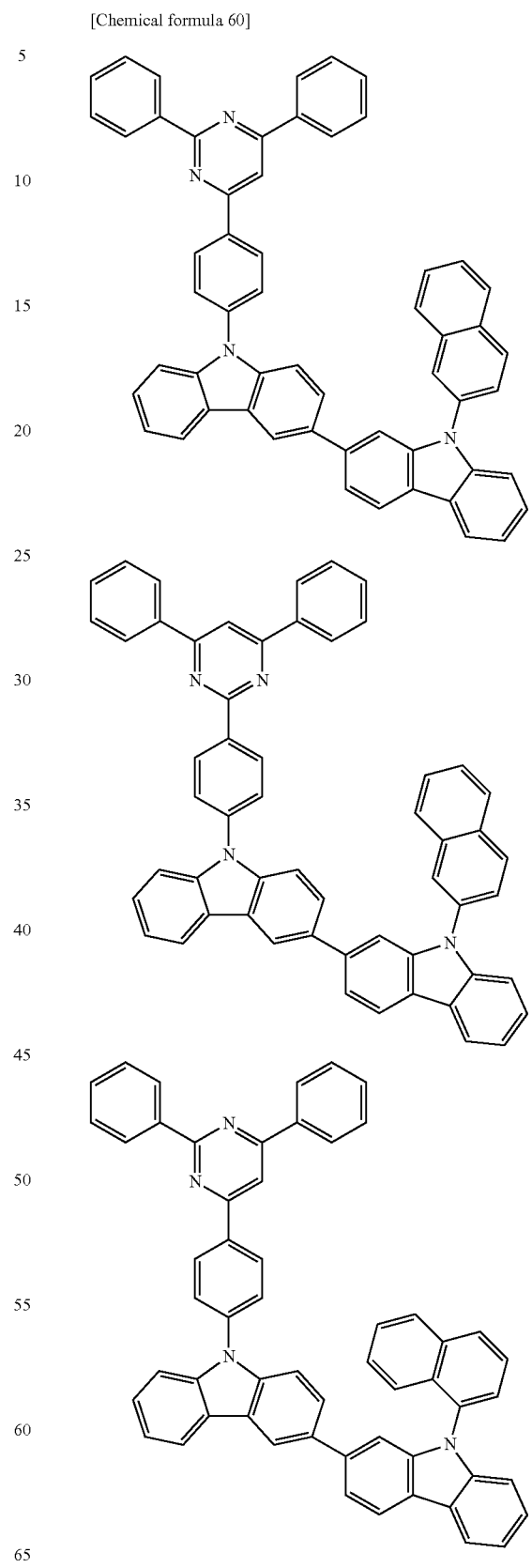
[Chemical formula 60]

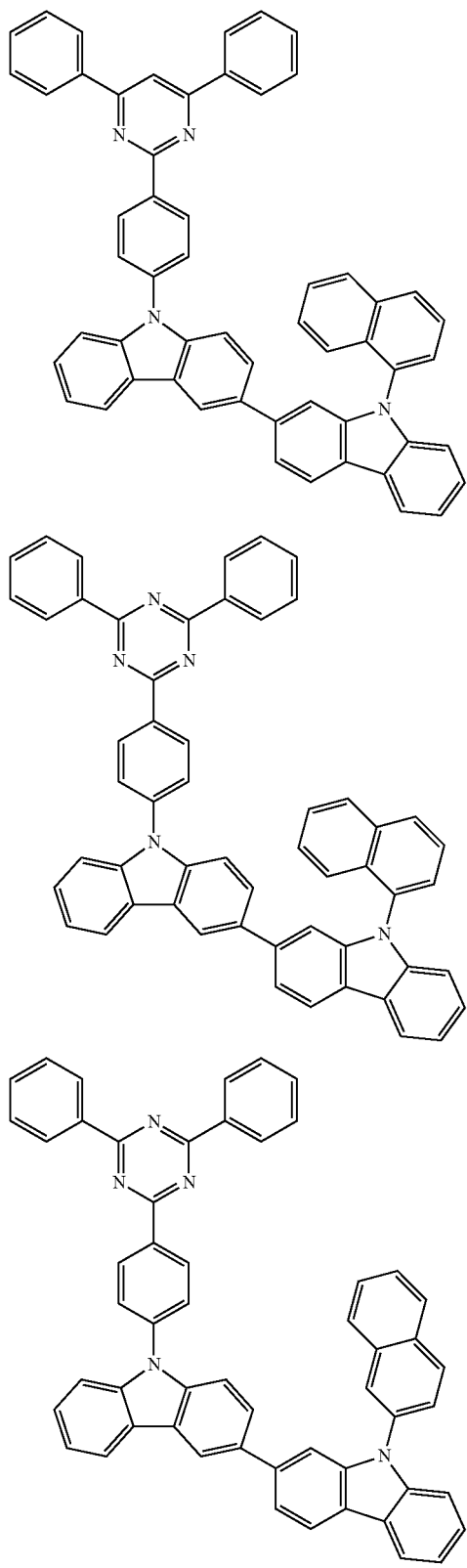
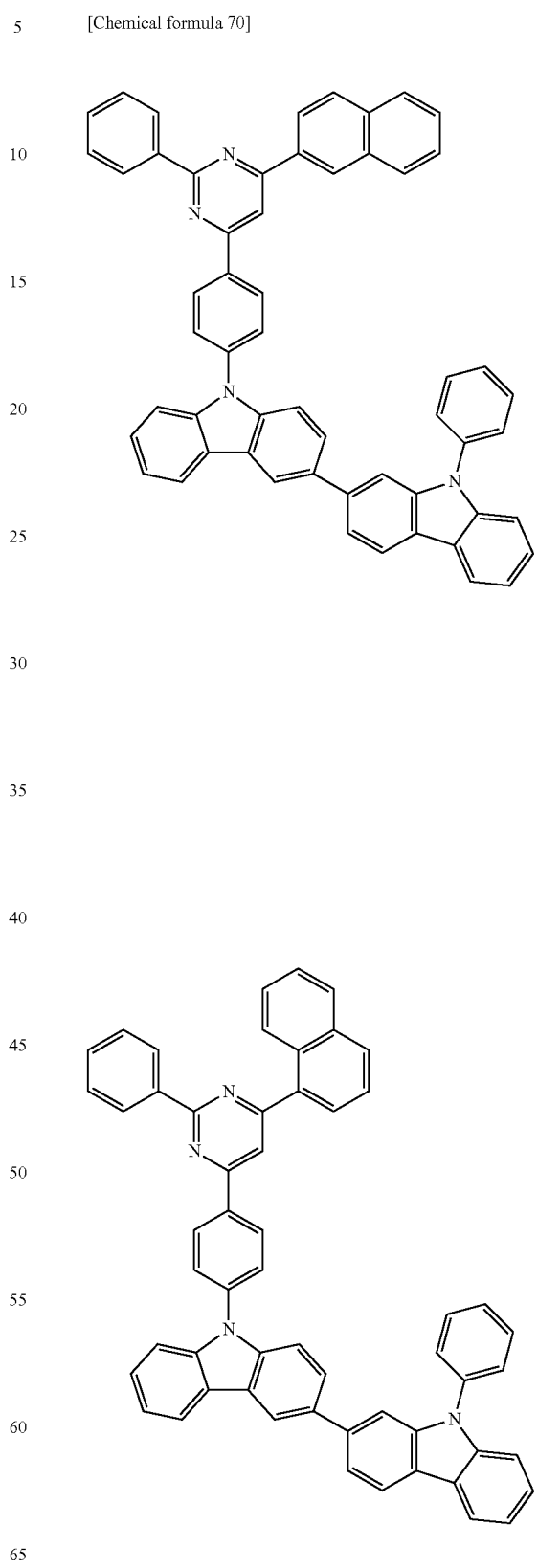
[Chemical formula 70]

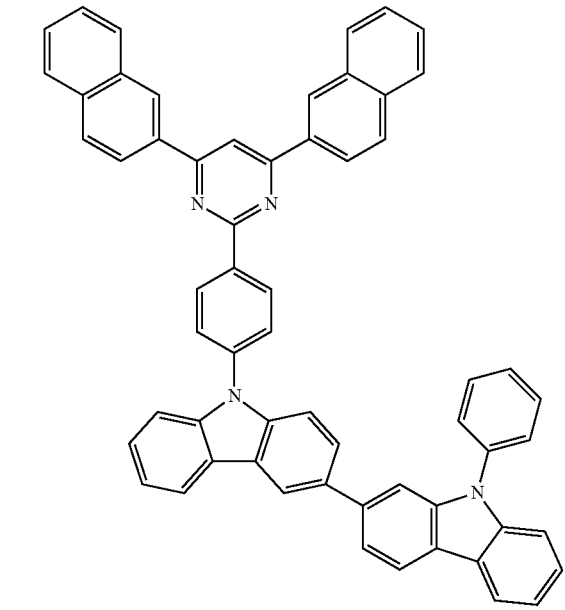
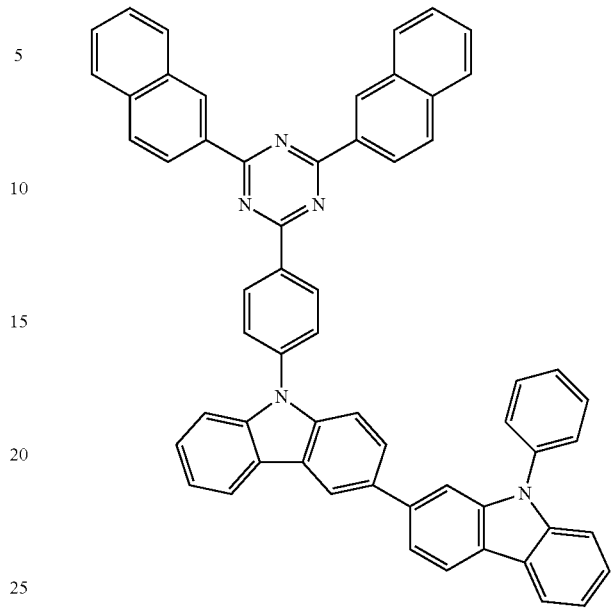
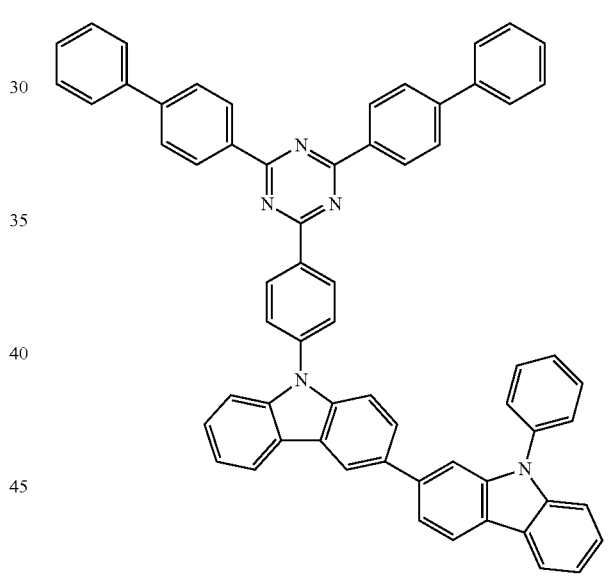
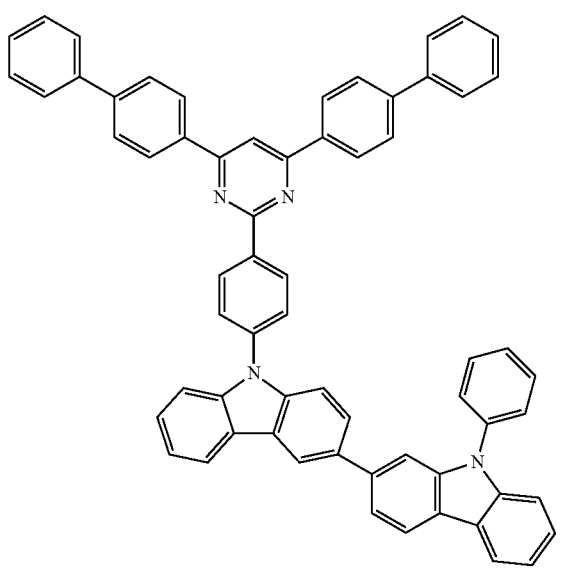
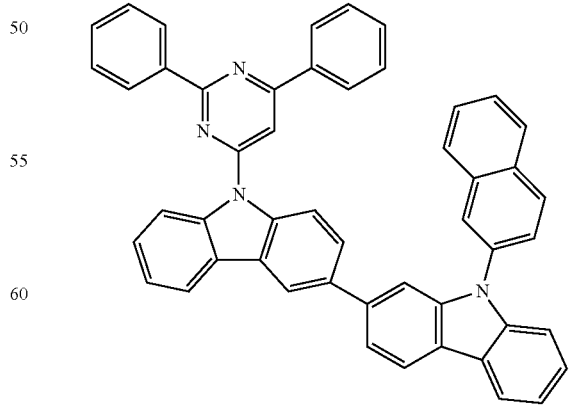

61
-continued
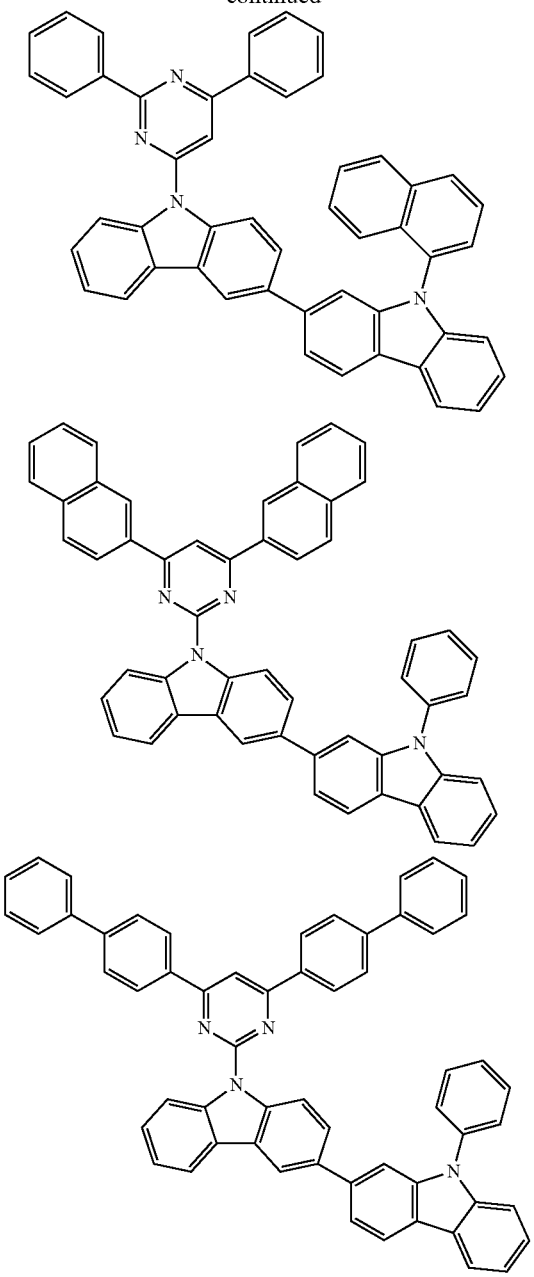
[Chemical formula 80]
62
-continued
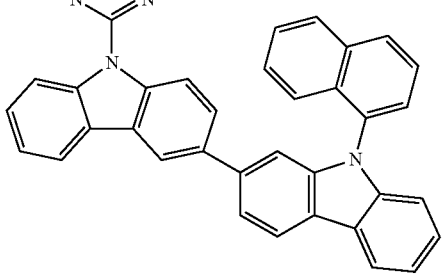
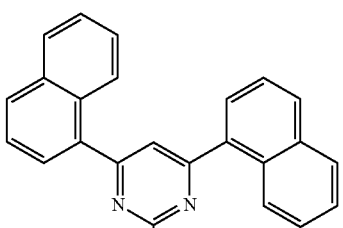
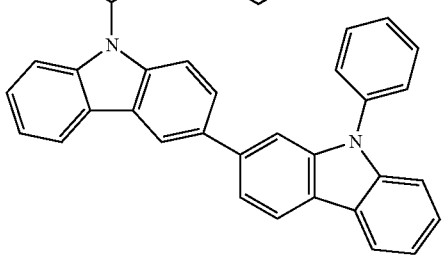
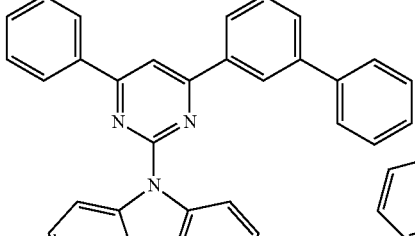
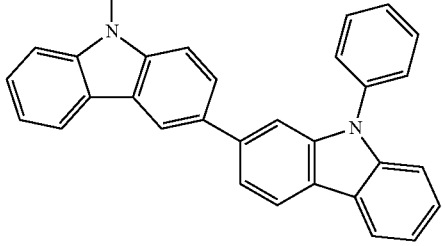

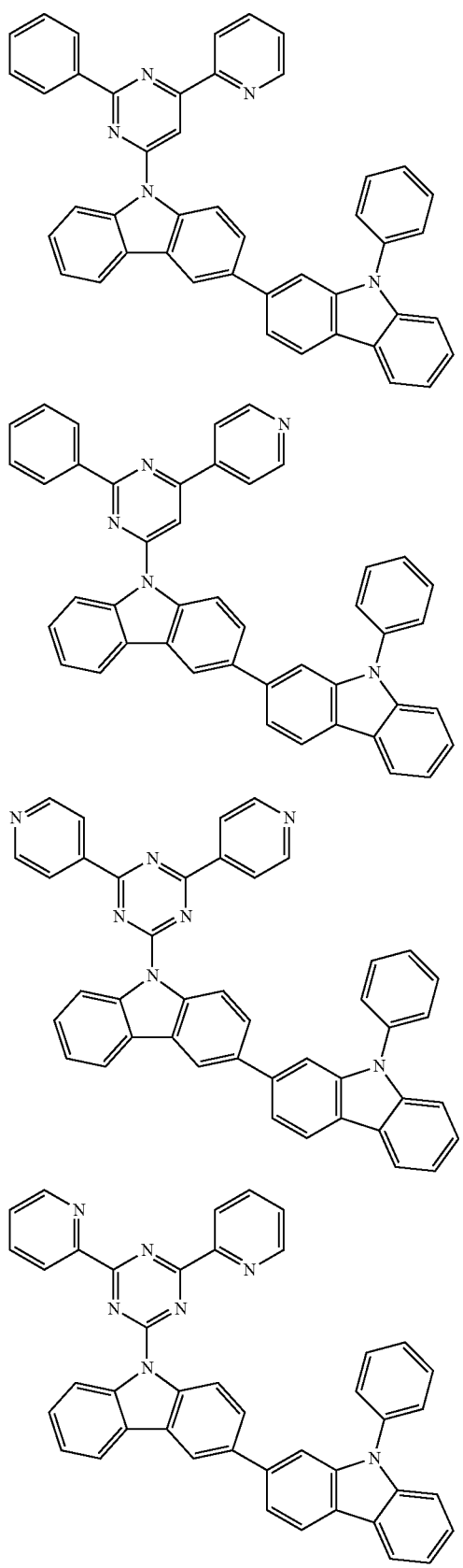
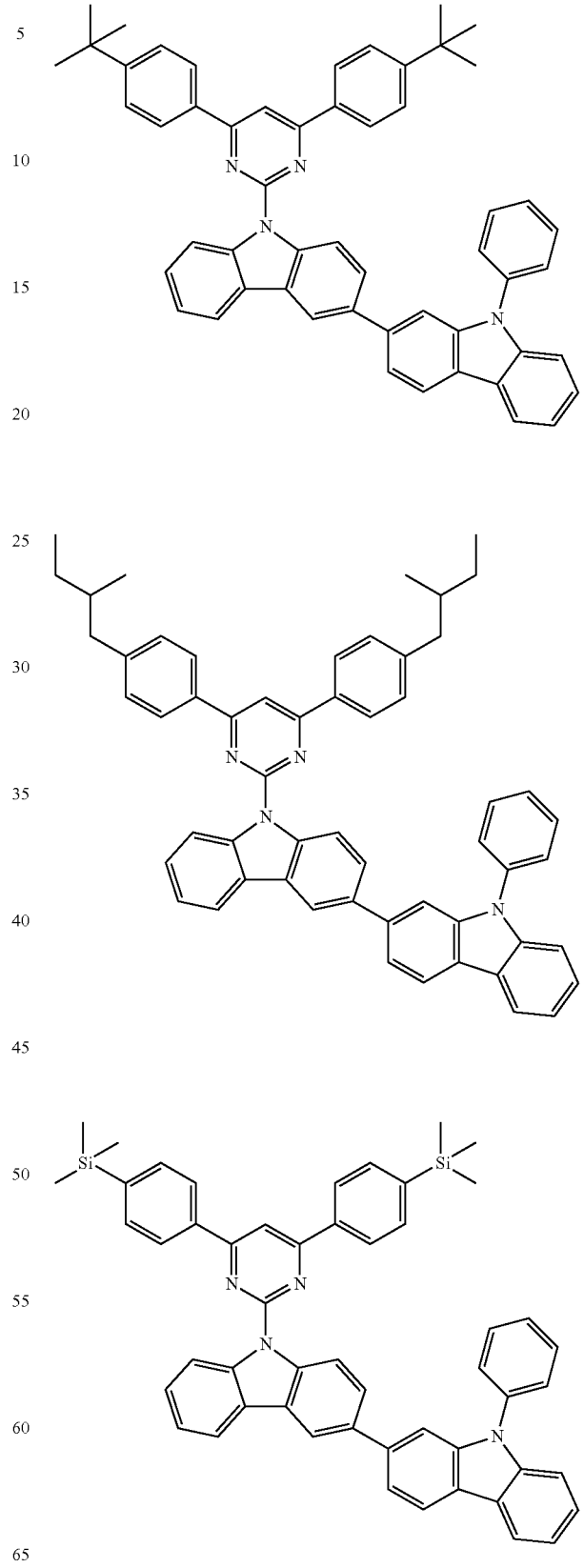
[Chemical fomula 90]

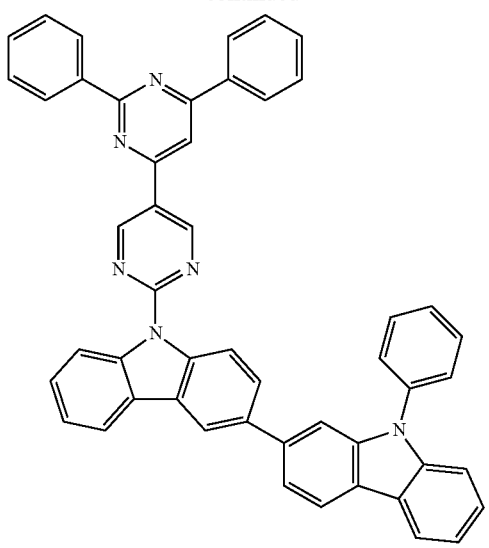
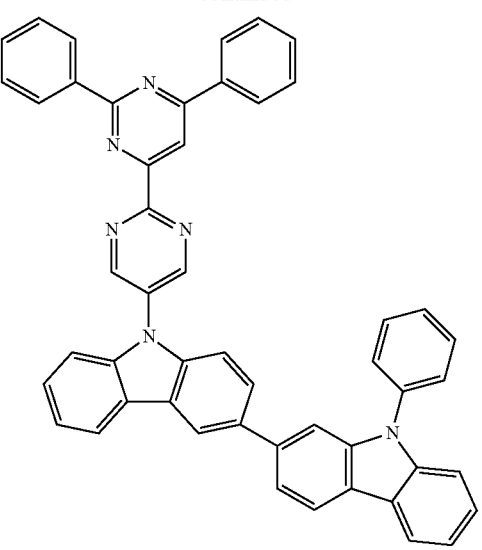
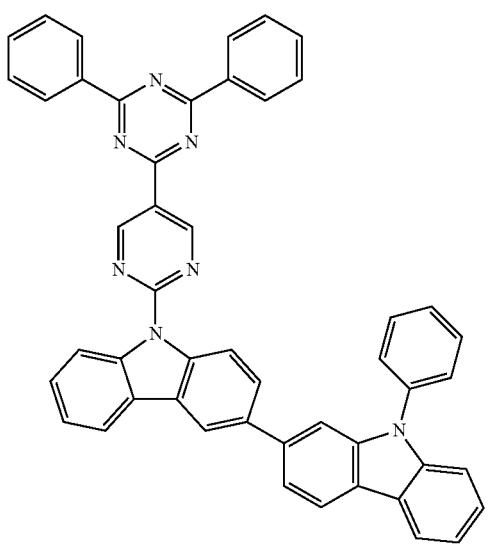
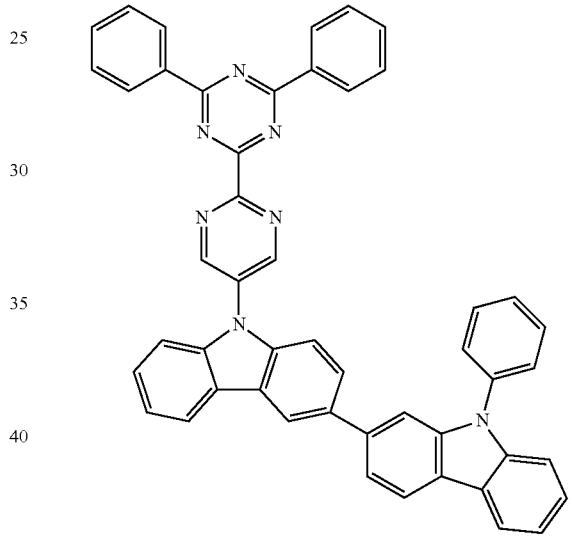
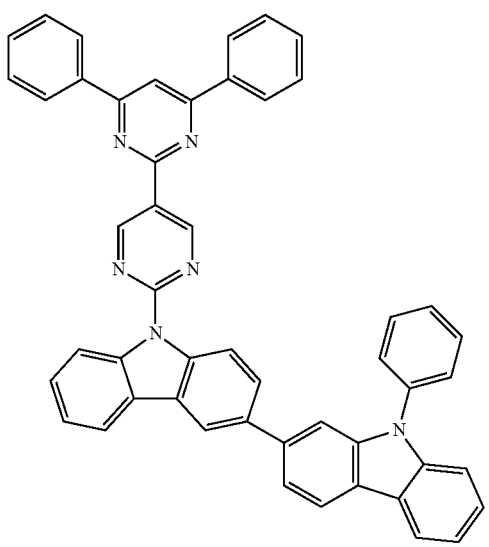
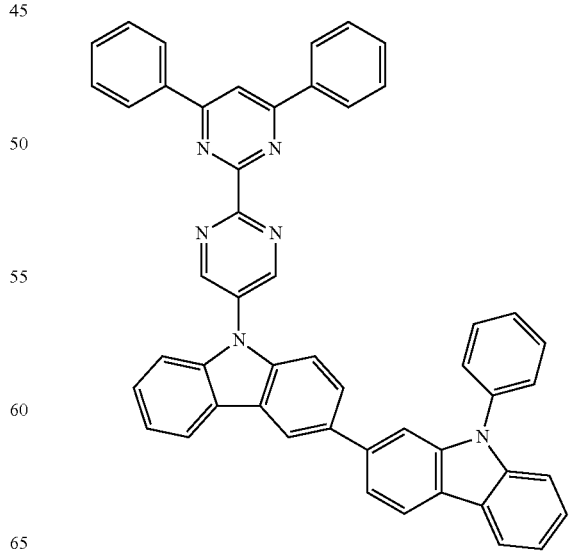

[Chemical formula 100]
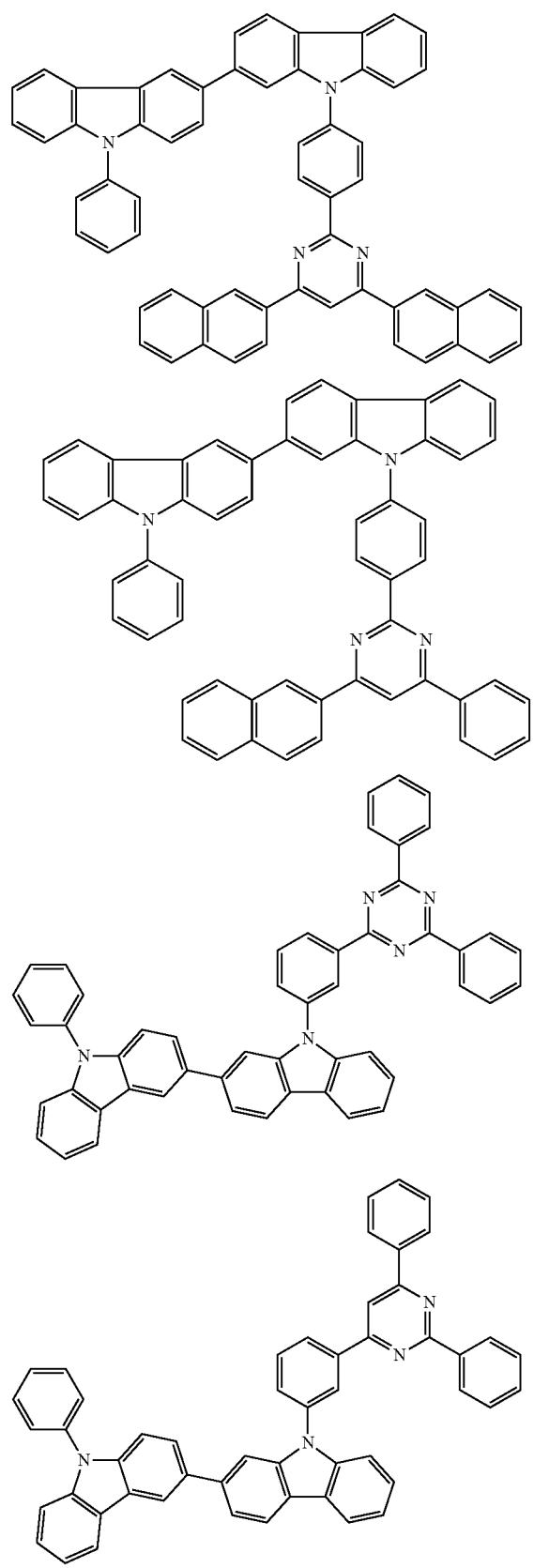
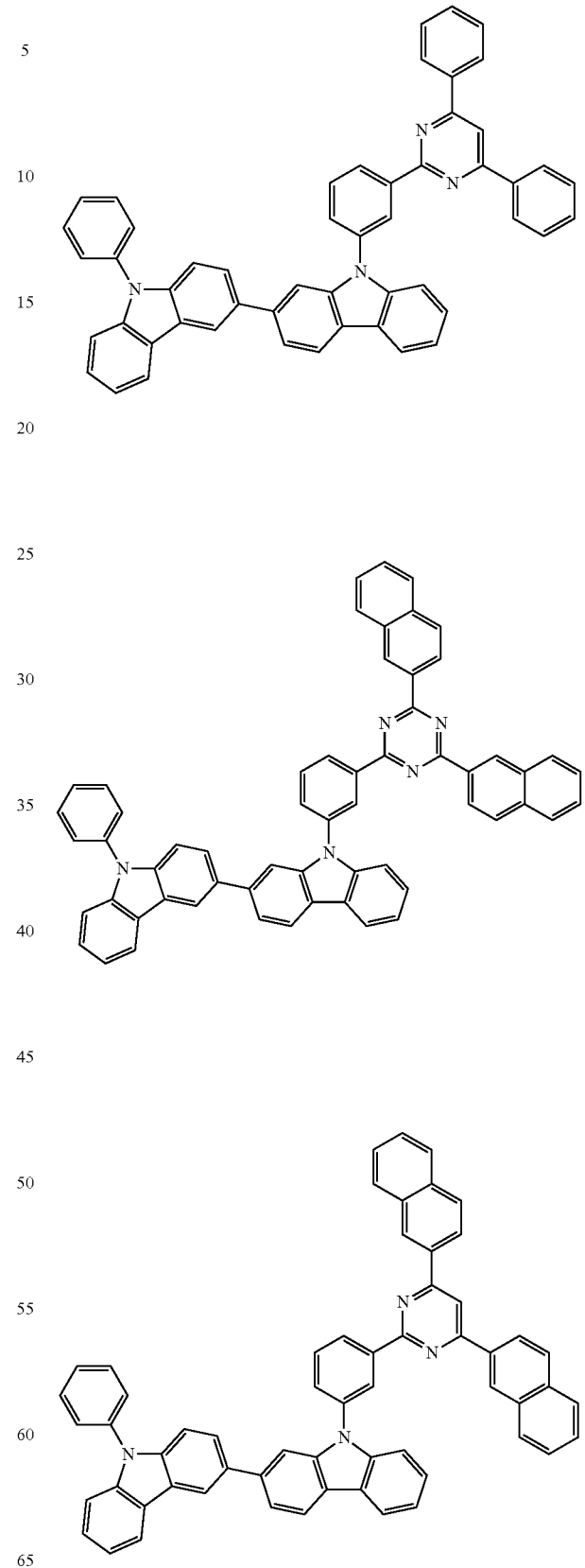

-continued
[Chemical formula 110]
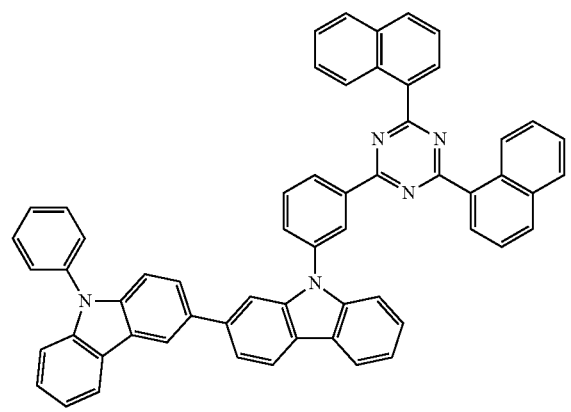
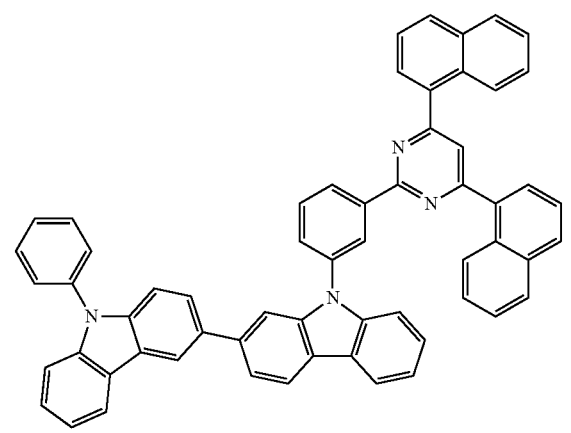
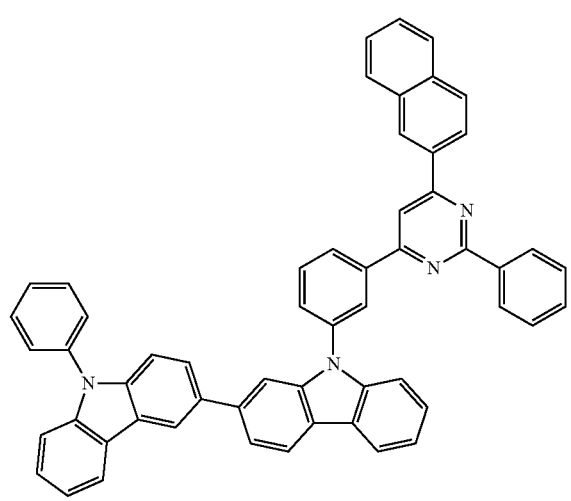
-continued
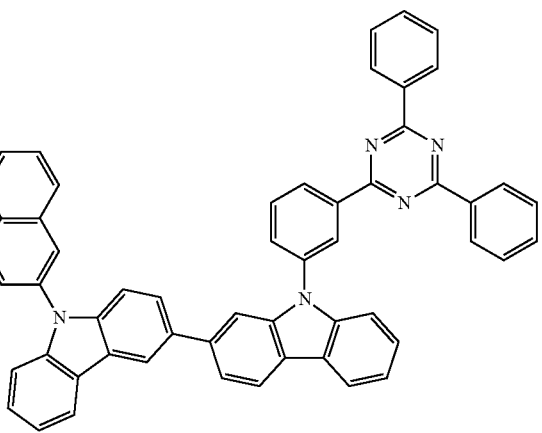
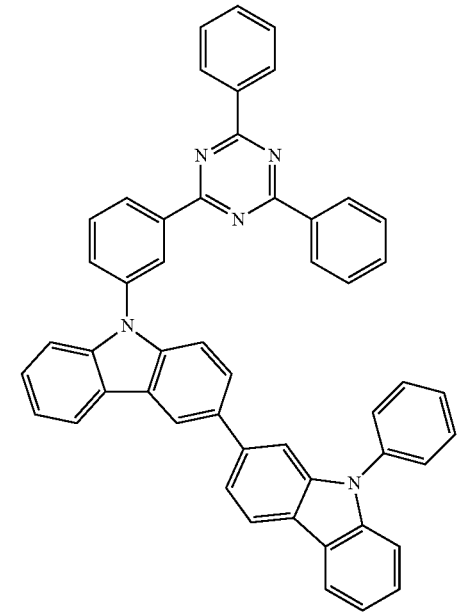
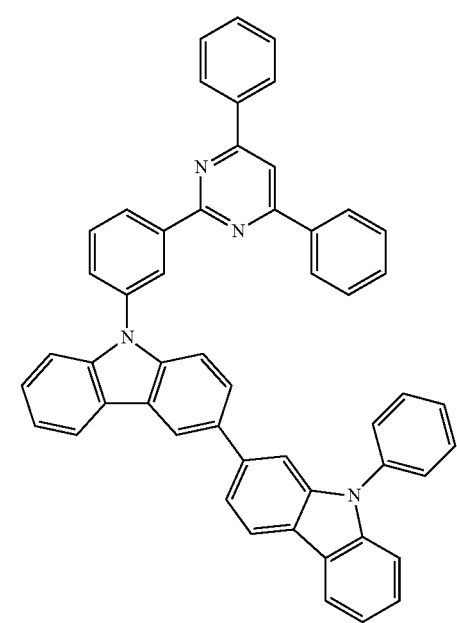

-continued
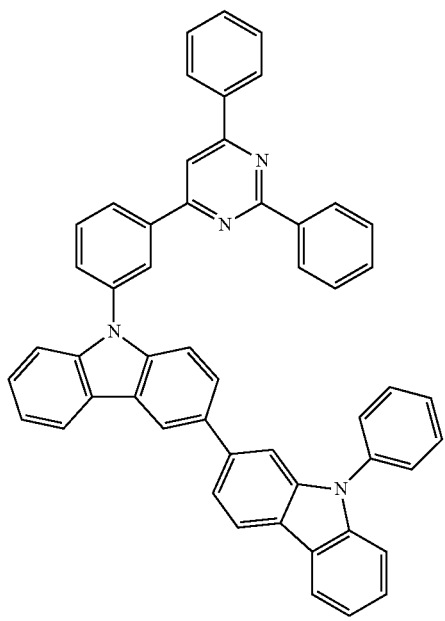
[Chemical formula 120]
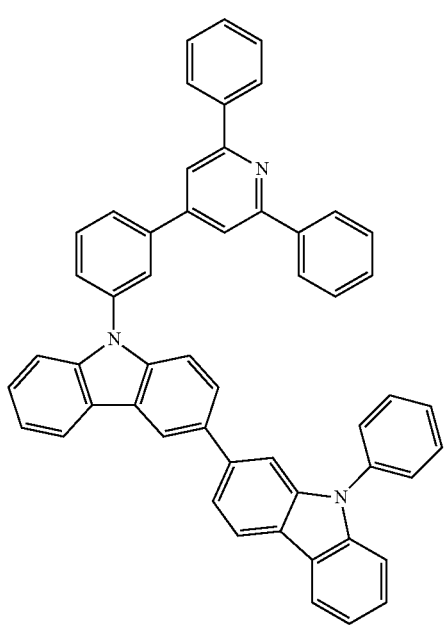
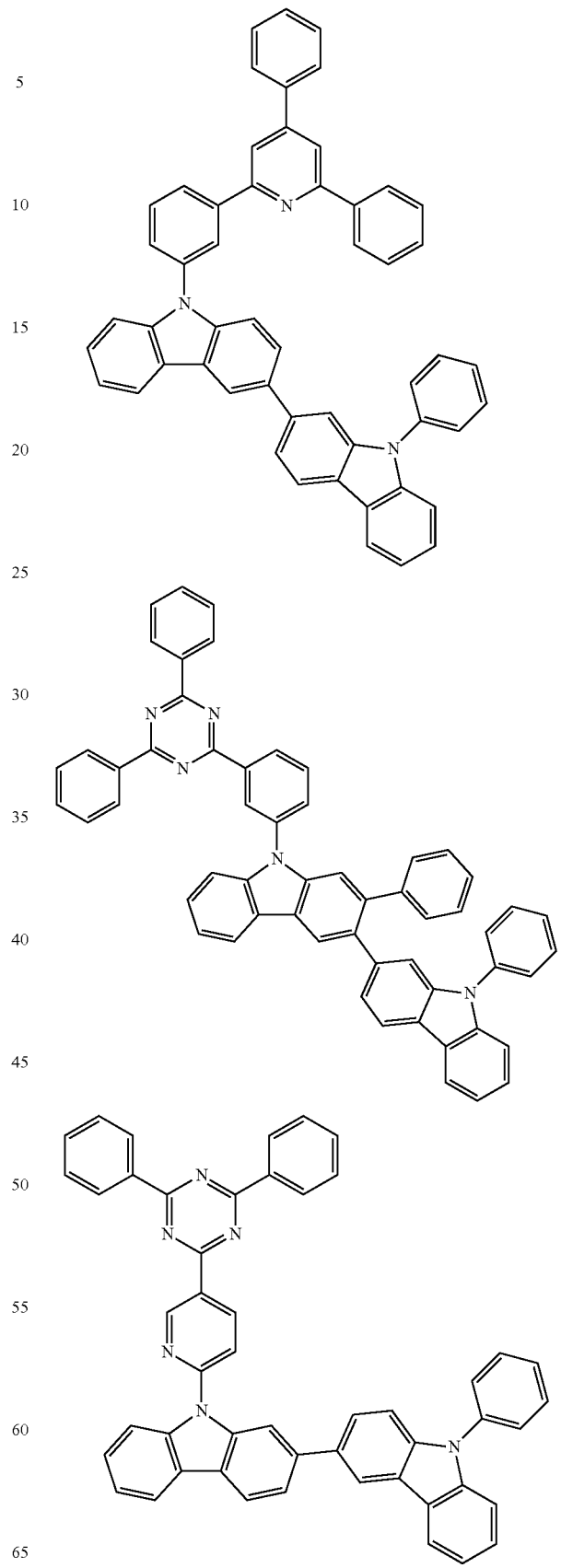

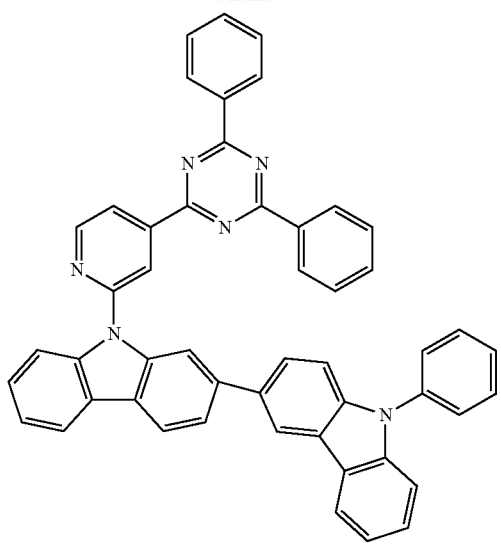
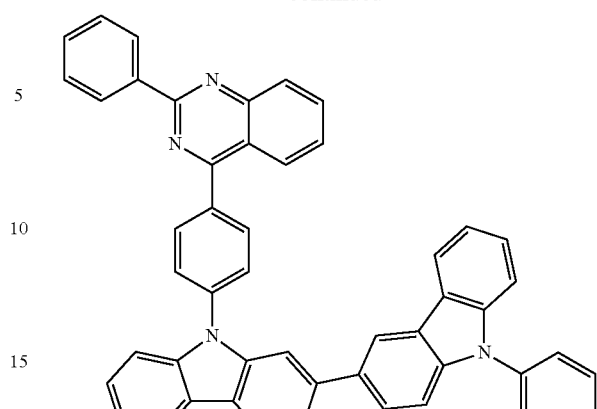
[Chemical formula 130]
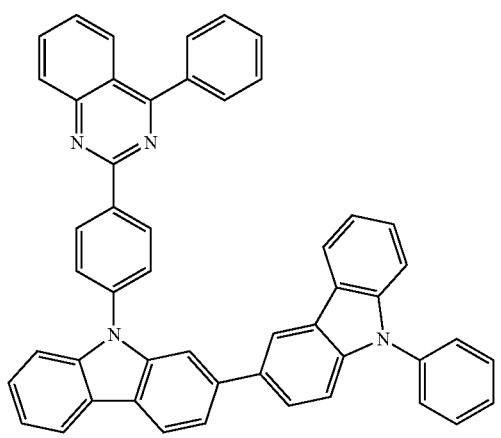
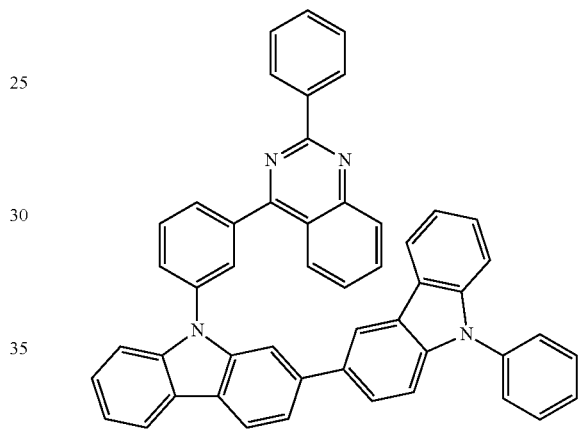
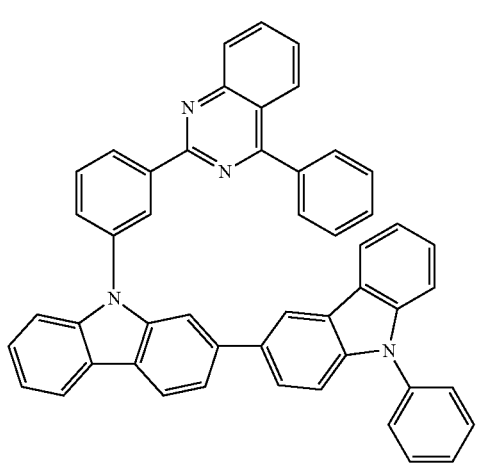
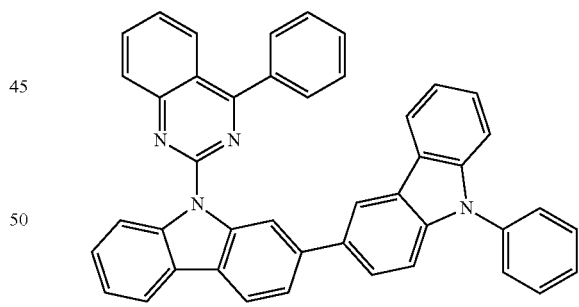
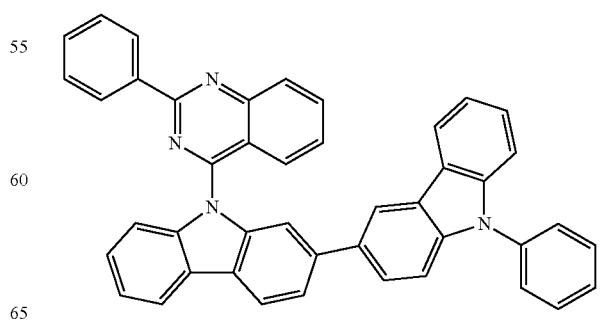

75
-continued
[Chemical formula 140]
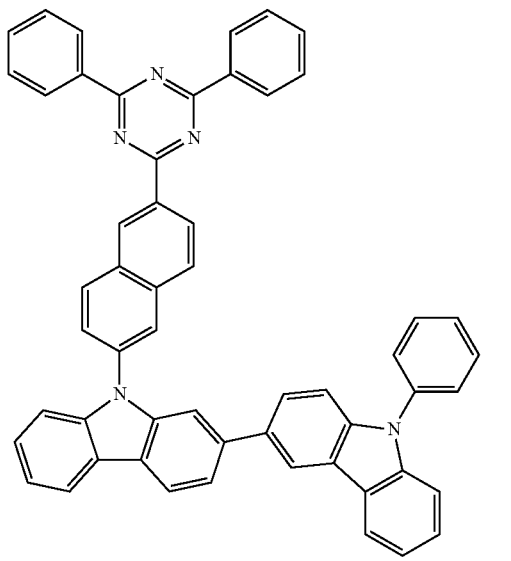
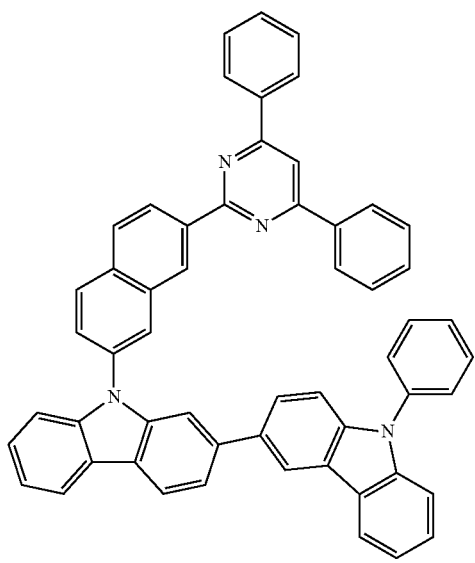
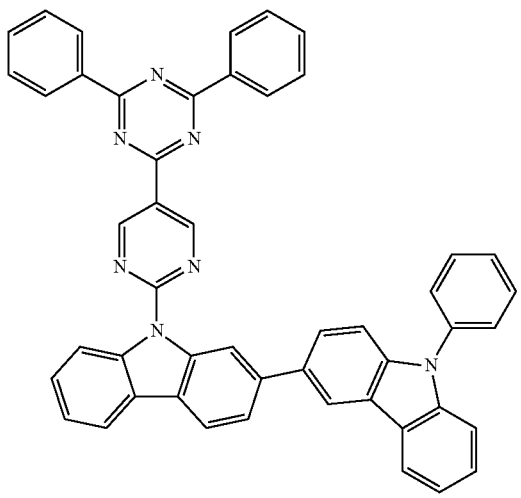
76
-continued
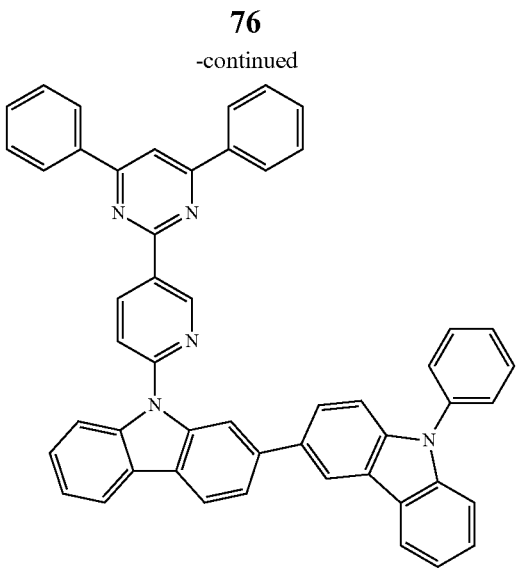
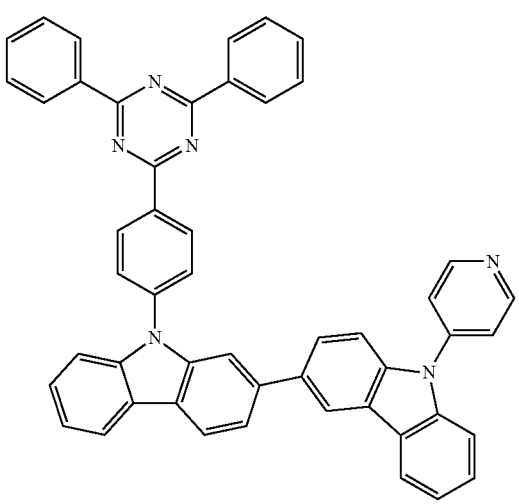
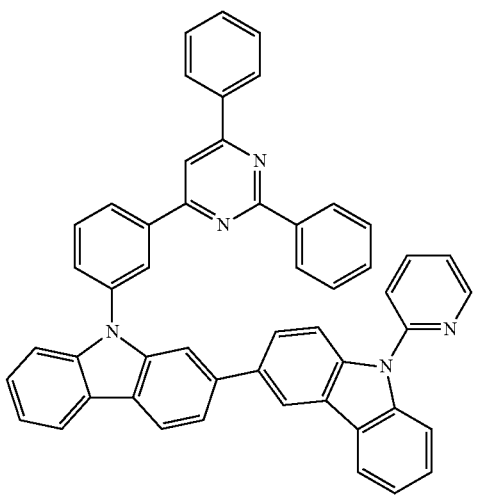

77
-continued
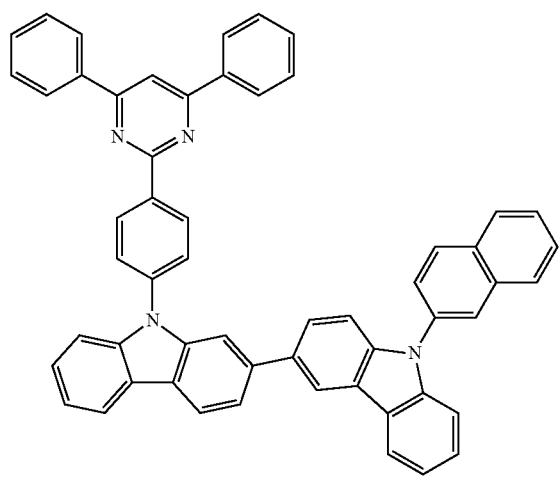
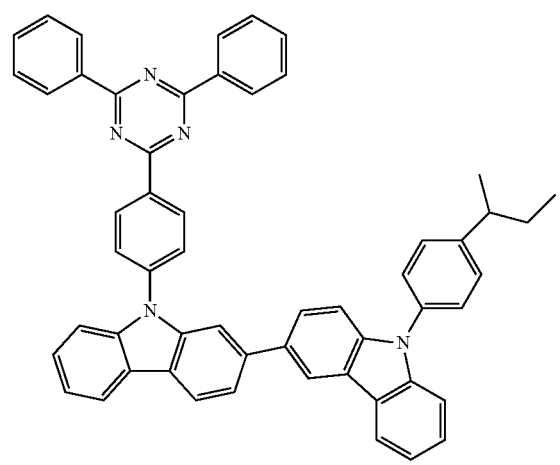
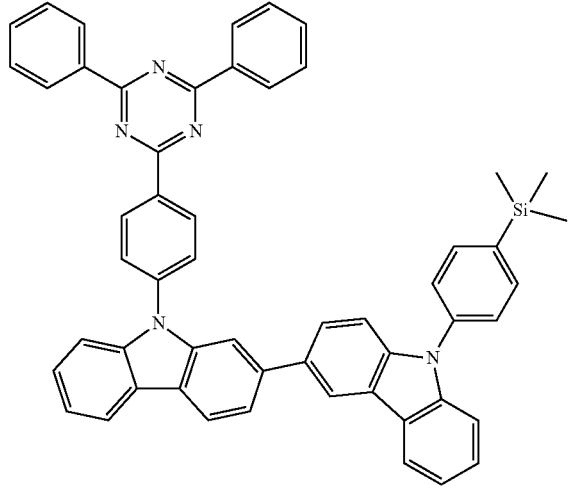
78
-continued
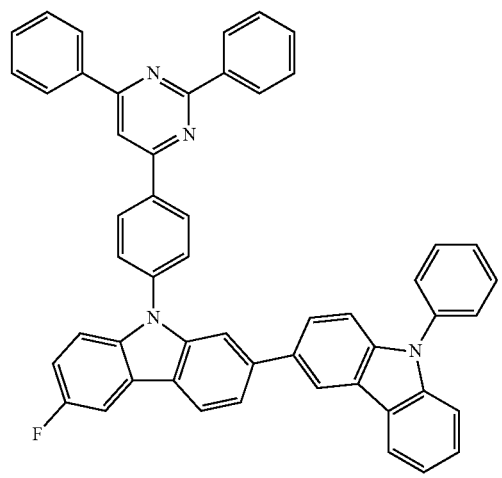
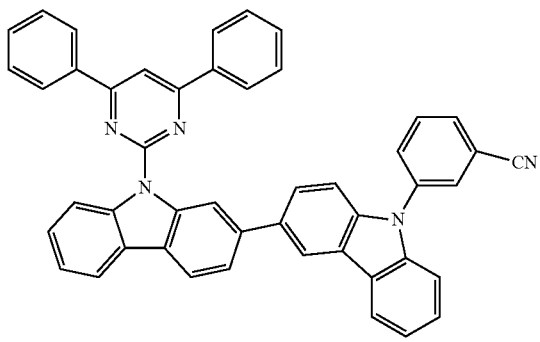
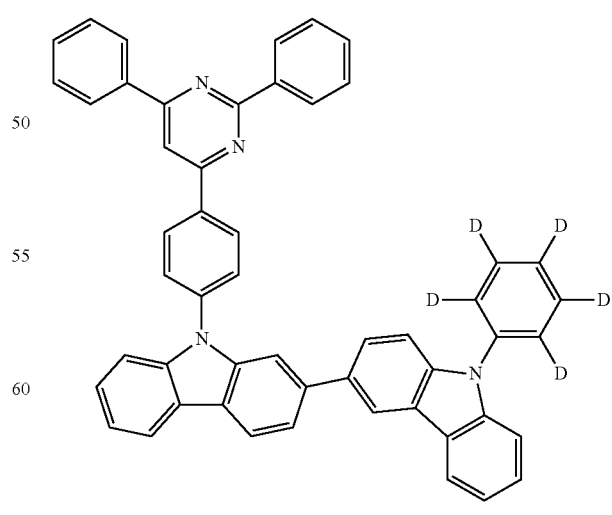

-continued

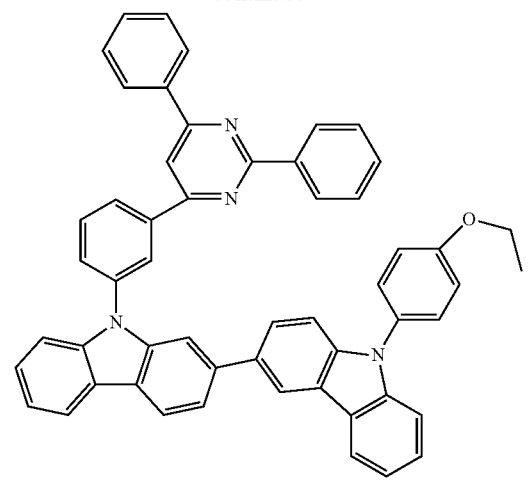

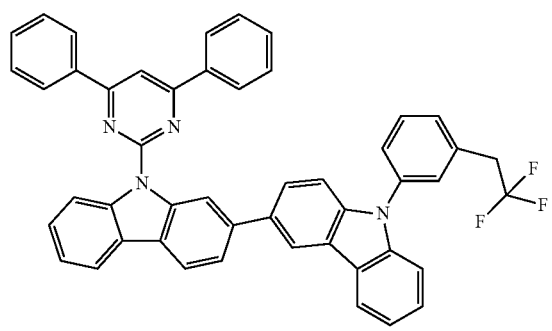

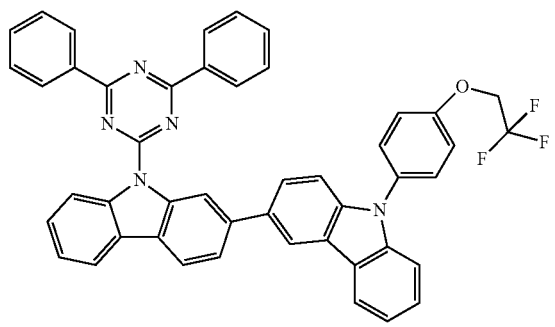

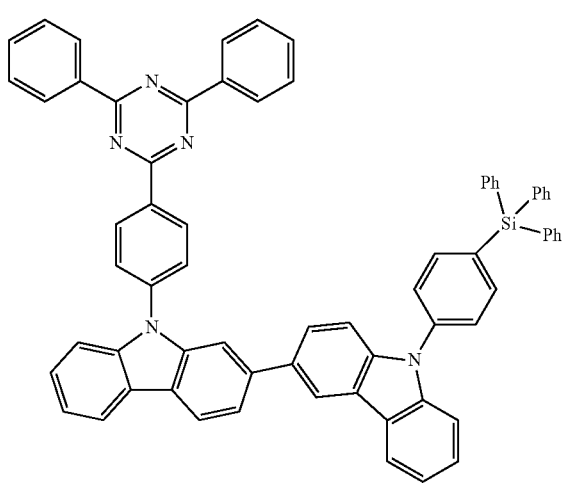

-continued

[Chemical formula 150]

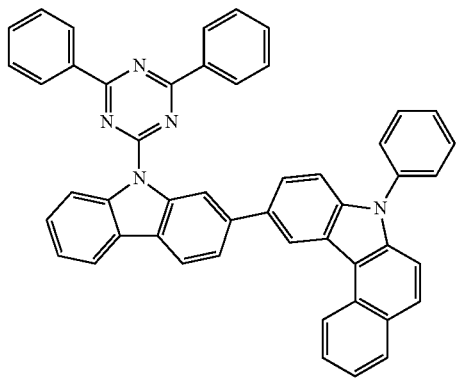

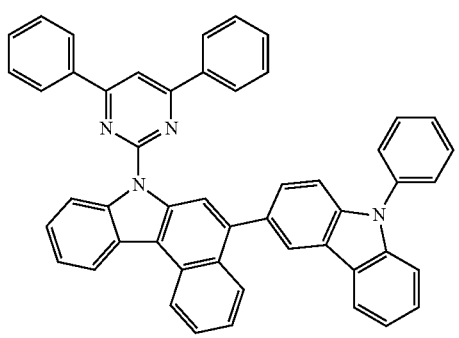

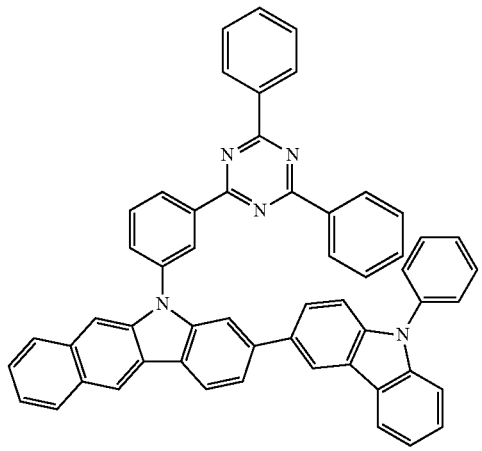

The biscarbazole derivative according to this exemplary embodiment represented by the formula (1A) or (1B) is a biscarbazole derivative in which carbazole skeletons are bonded to each other respectively at a second position and a third position. In general, a reaction active position of carbazole is a third position, not a second position. For this reason, synthesis of carbazole derivatives having a substituent at a second position is more difficult than synthesis of carbazole derivatives having a substituent at a third position, e.g., synthesis of a biscarbazole derivative in which carbazole skeletons are bonded to each other at their third positions. In this exemplary embodiment, these compounds are synthesized by a method described in examples described later in this document.

Some examples of the green phosphorescent dopant material according to this exemplary embodiment represented by the formula (4A) are as follows:

[Chemical formula 160]
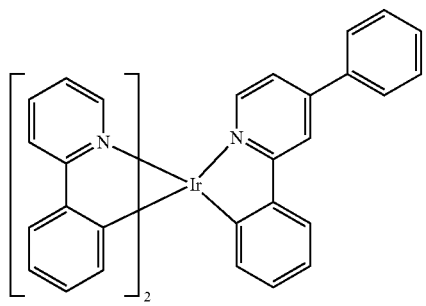
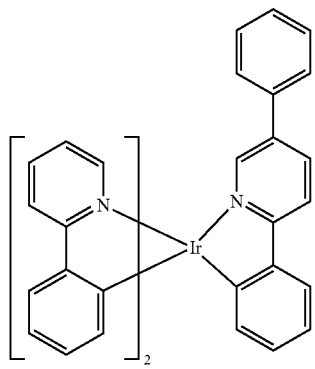
Compound 3
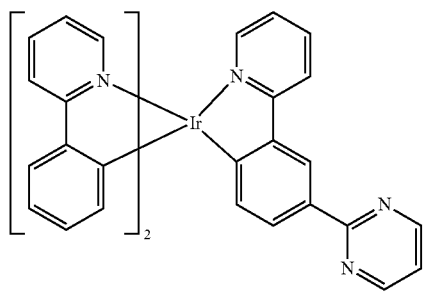
Compound 4
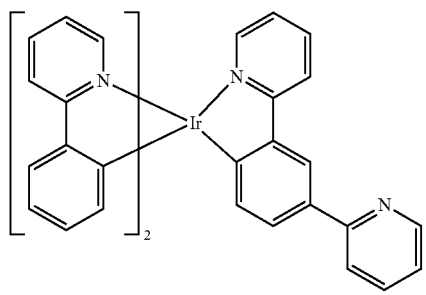
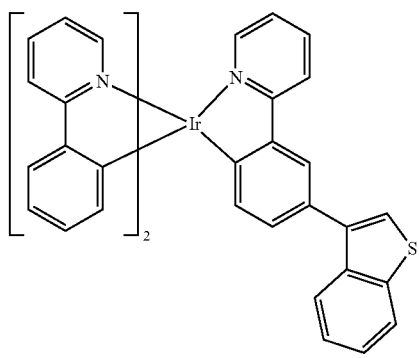
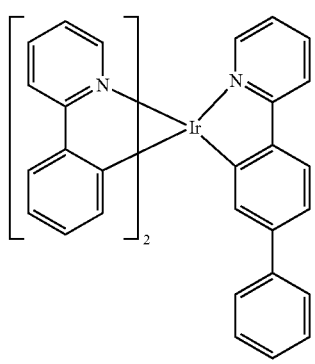
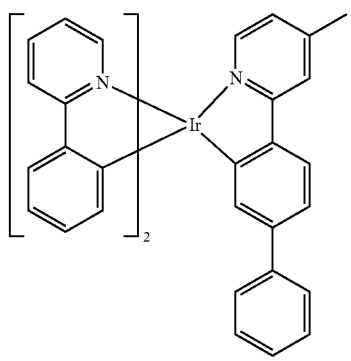
[Chemical formula 170]
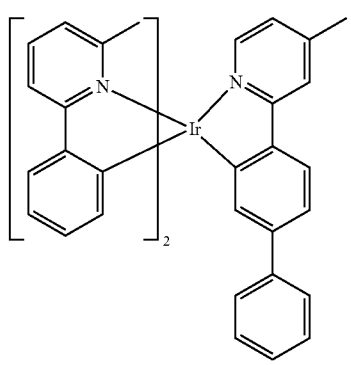

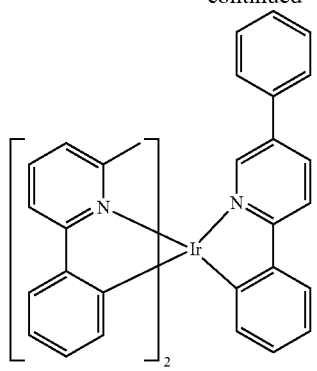
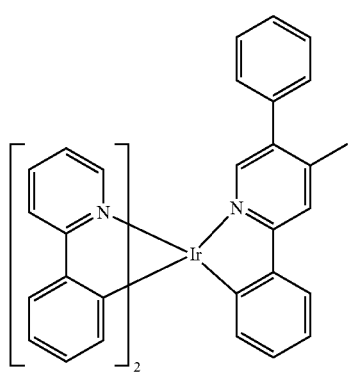
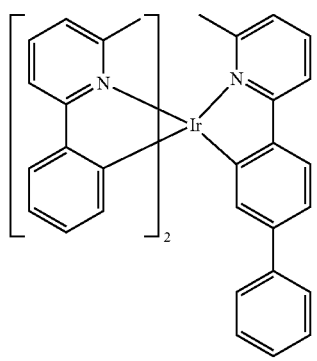
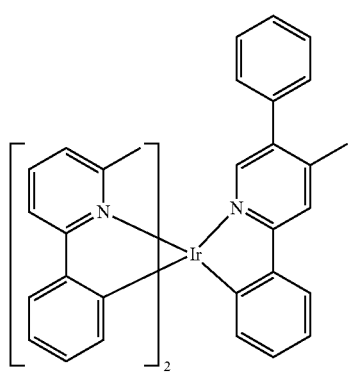
[Chemical formula 180]
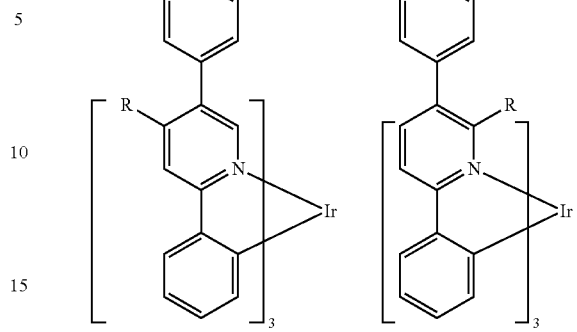
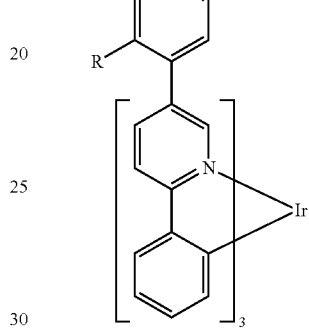
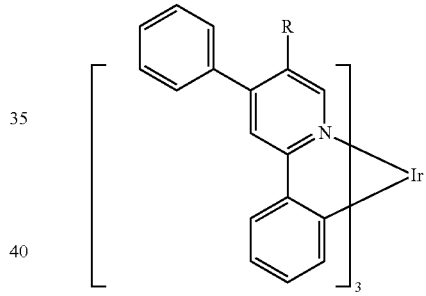
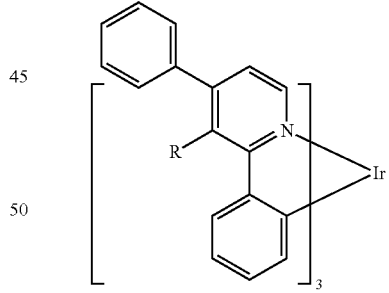
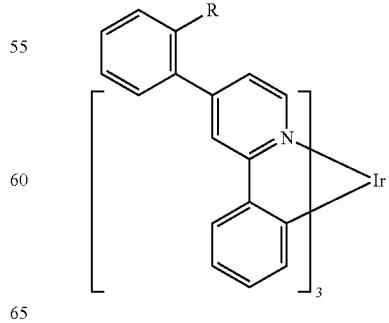
where R is not hydrogen, for example, R is an alkyl.

[Chemical formula 190]
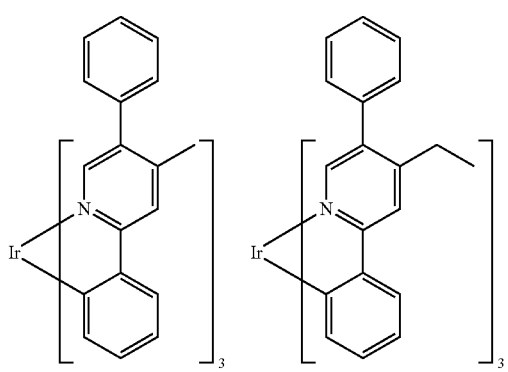
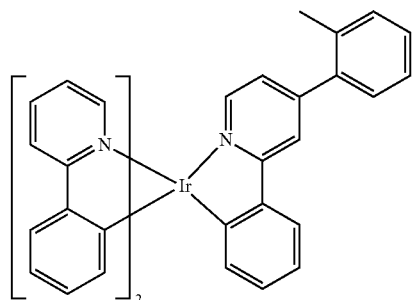
[Chemical formula 200]
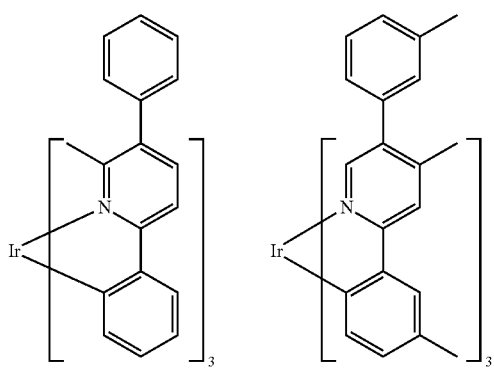
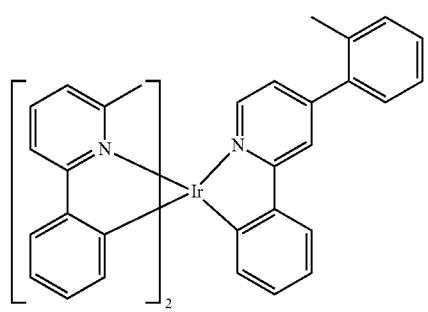
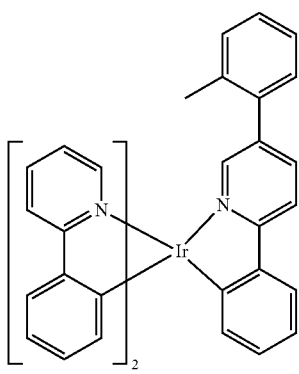
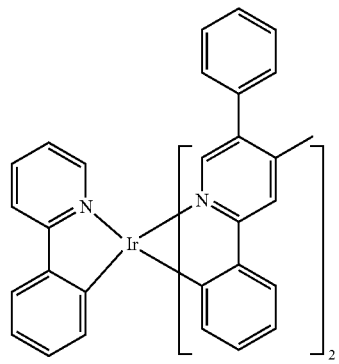
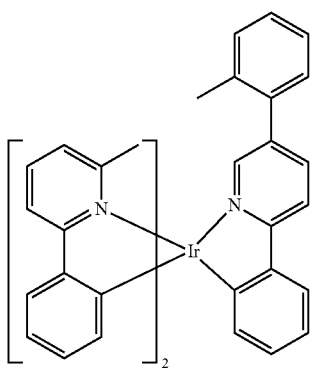
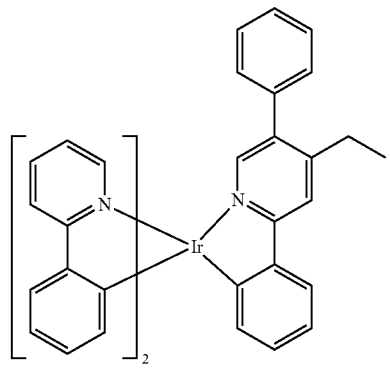

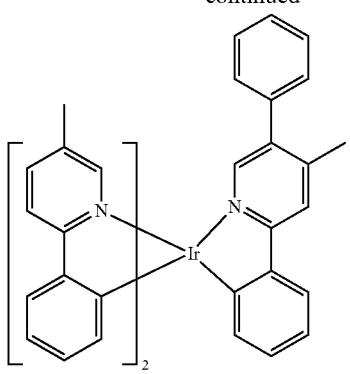

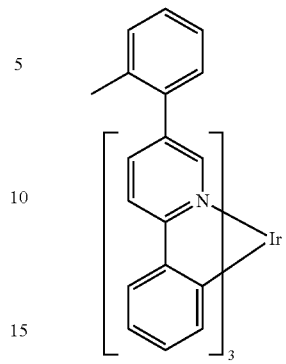

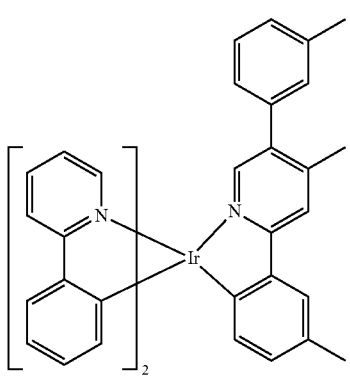

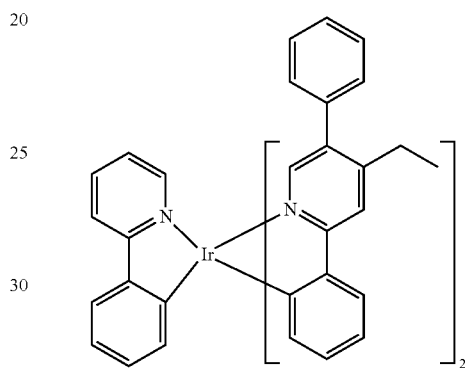

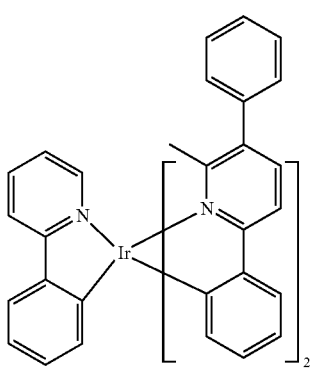

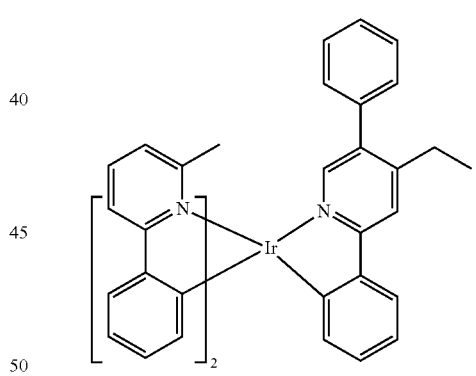

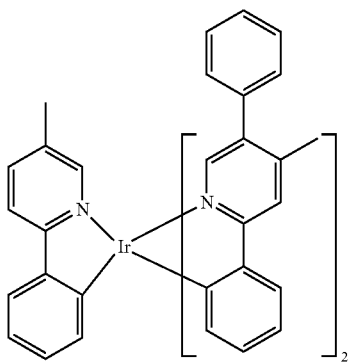

As mentioned above, the biscarbazole derivative compounds for the second host material in the organic EL device of this exemplary embodiment are represented by the formula (1A') or (1B'). The formulas (1A') and (1B') are the formulas (1A) and (1B) in which $X_1$ is a single bond. Thus, the compounds from the list of exemplary compounds for the formulas (1A) and (1B) in which $X_1$ is a single bond are examples of compounds represented by the formula (1A') or (1B').

Examples of compounds for the biscarbazole derivative as the second host material according to this exemplary embodiment represented by the formula (2) are as follows:

[Chemical formula 260]
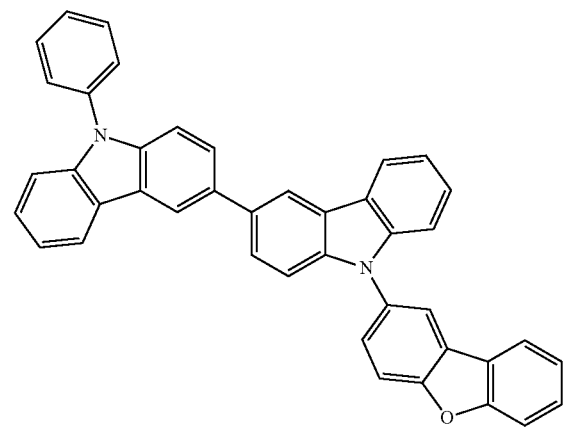
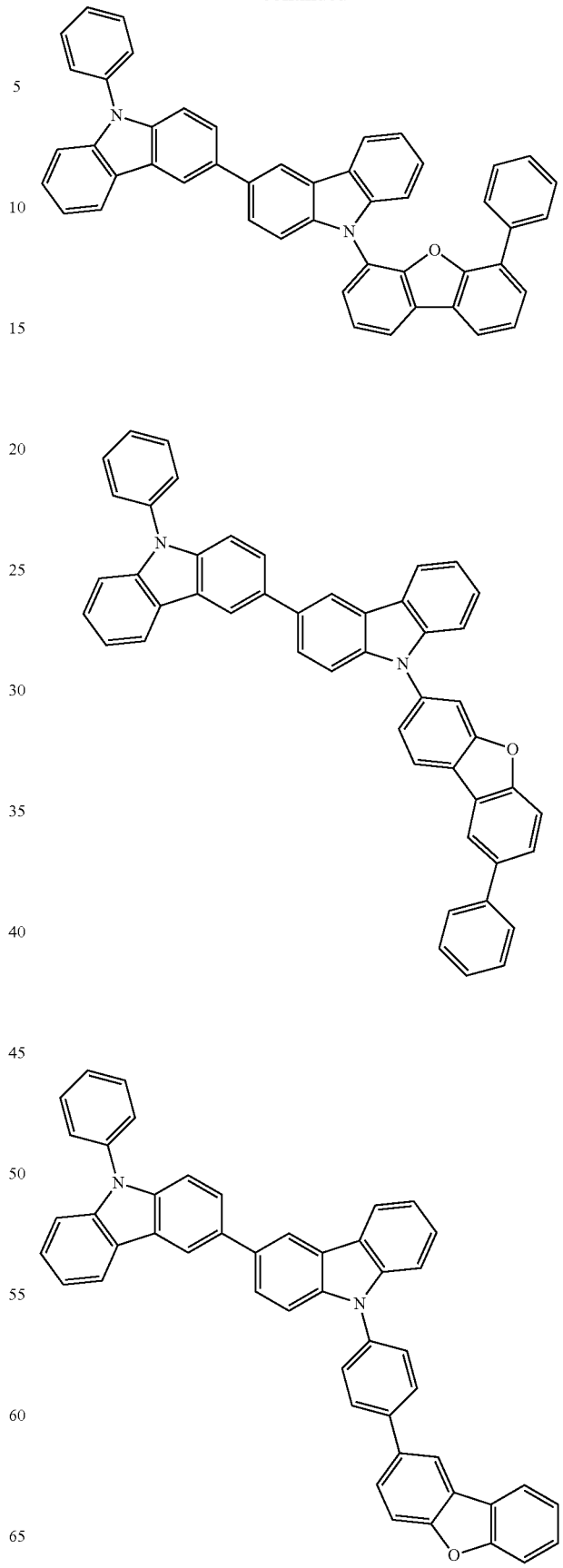

91
-continued
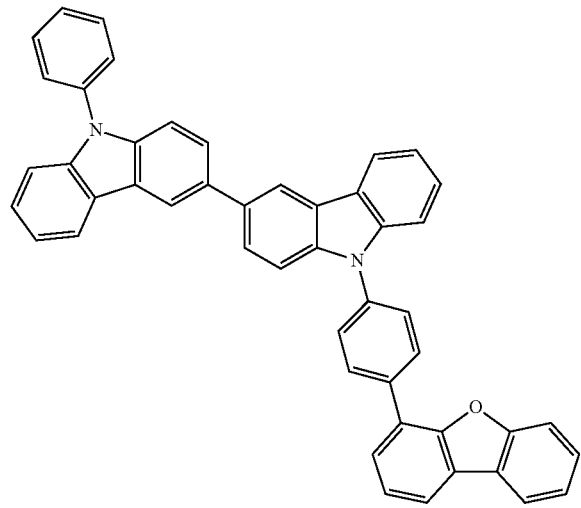
92
-continued
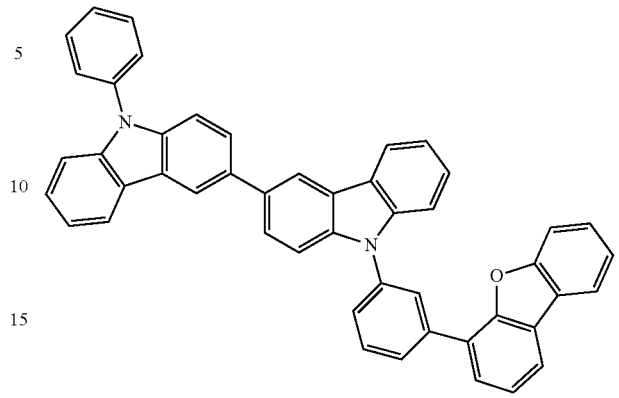
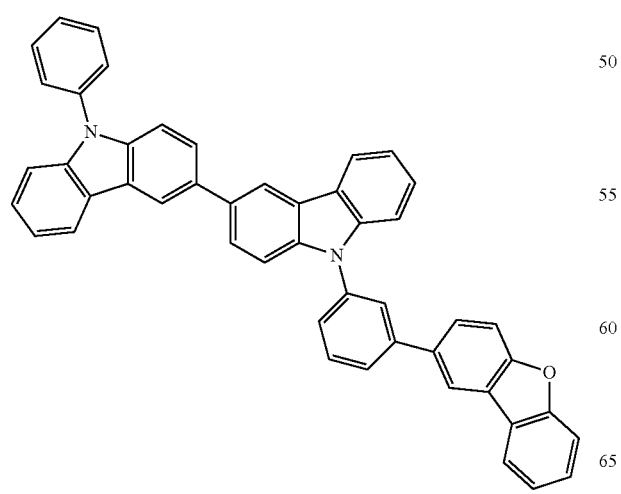
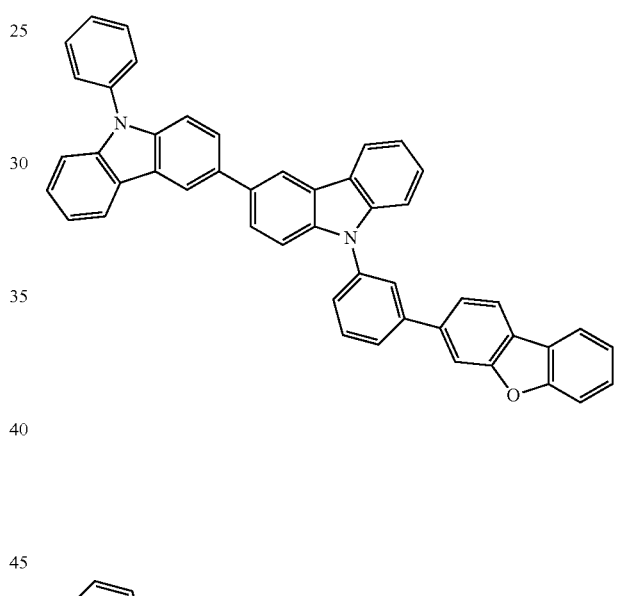

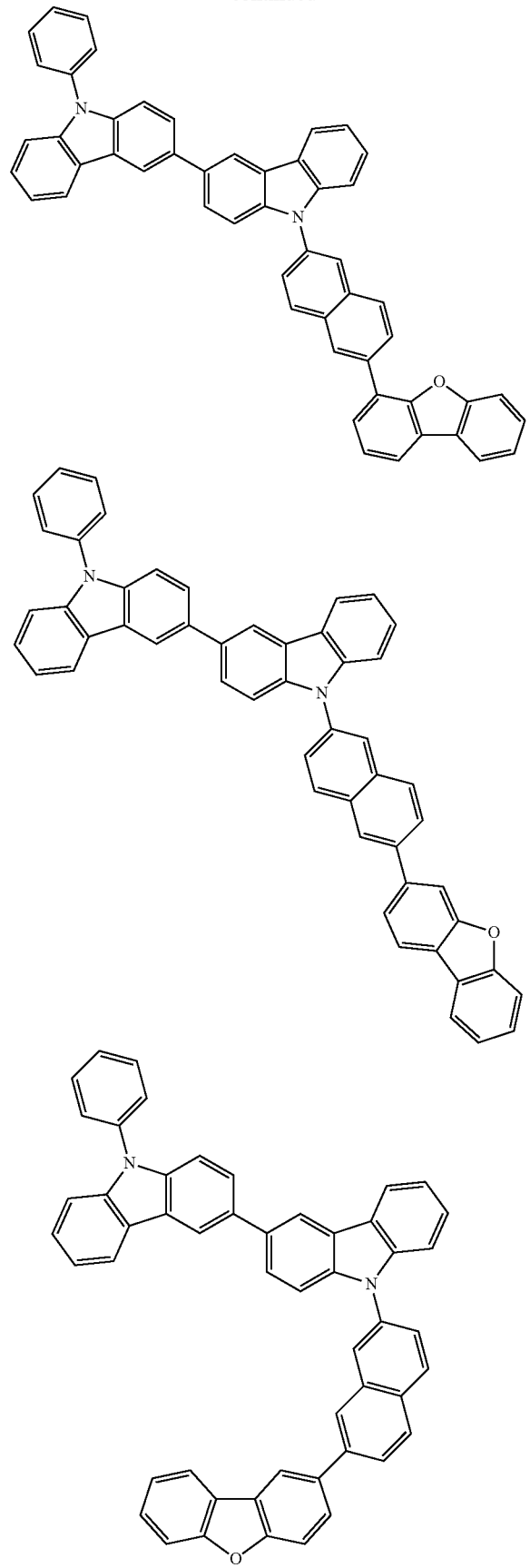
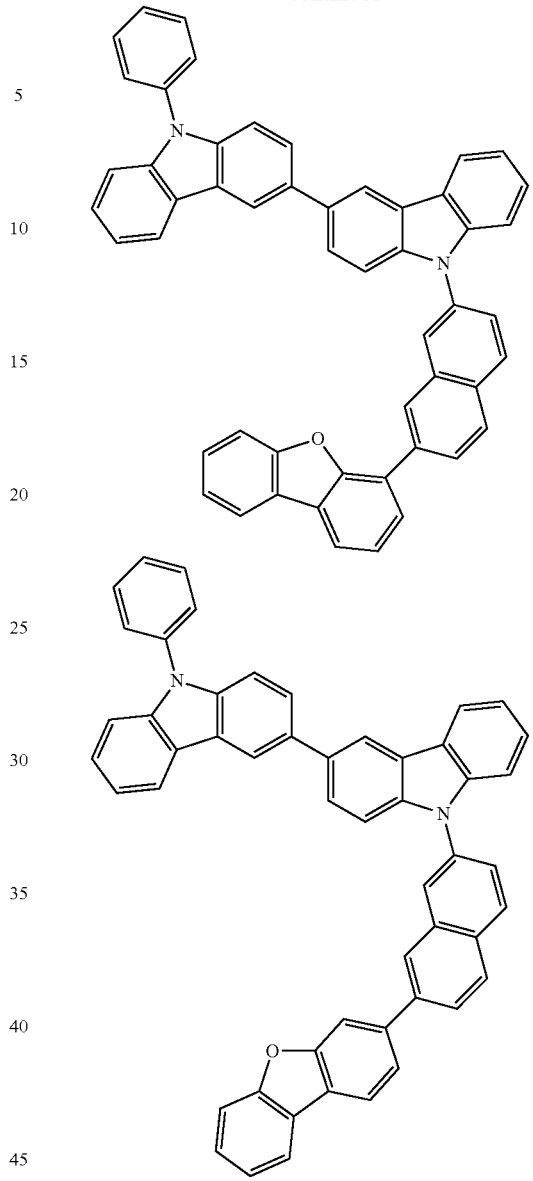

The organic EL device according to this exemplary embodiment may preferably contain the electron injecting/transporting layer that contains the biscarbazole derivative compound.

The organic EL device according to this exemplary embodiment may preferably contain at least one of the electron injecting/transporting layer and the hole blocking layer that contains the biscarbazole derivative compound.

The organic EL device according to this exemplary embodiment may preferably include the hole transporting layer (hole injecting layer) that contains the biscarbazole derivative compound.

The carbazole derivative compounds represented by the formula (1A) or (1B) according to this exemplary embodiment tends to have a smaller ionization potential (IP) than, for instance, a biscarbazole derivative in which carbazole skeletons are bonded to each other at their third positions. When the carbazole derivative according to this exemplary embodiment is used as an organic-EL-device material, the carbazole derivative is expected to have a higher hole injectivity.

Moreover, in the biscarbazole derivative, to change a bonding position between carbazoles means to change a conjugated system. For instance, when a biscarbazole derivative in which carbazole skeletons are bonded to each other at their third positions is changed to the carbazole derivative according to the exemplary embodiment of the invention in which carbazole skeletons are bonded to each other respectively at a second position and a third position, a conjugated system is cut off to increase a singlet energy gap (S1) and lower affinity (Af). Accordingly, it is expected that such a change of the bonding position from the third positions to the second and third positions enables control of electron injectability into the carbazole derivative.

The invention presented in the present disclosure provides a novel combination of one or more emitter host materials and a phosphorescent dopant material. The one or more emitter host material comprises one or more of biscarbazole derivative material having a hole transporting capability and an electron transporting capability and exhibiting an excellent carrier balance. The organic EL device made with the combination of emitter host and phosphorescent dopant materials exhibit low operational voltage and enhanced lifetime. The inventors achieved these enhancements after a dedicated study. The inventors found that a compound including two carbazolyl groups and a nitrogen-containing heterocyclic group effectively works for optimizing a carrier balance in the emitting layer of an organic EL device when used as a host material in the emitter layer of the device.

However, as mentioned previously above, a luminous efficiency and lifetime of multilayered organic EL devices depend on a carrier balance of the entire organic EL device. The main factors for controlling the carrier balance are carrier transporting capability of each of the organic layers and carrier injecting capability in the interfacial region of separate organic layers. In order to balance the carrier injecting capability to neighboring layers in the emitting layer (recombination region), it is preferable to adjust the carrier balance by a plurality of host materials. Specifically, it is preferable that, in addition to the first host material, the second host material is suitably selected as a co-host in the emitting layer. The co-host system of the combinations disclosed herein were found to provide such enhancements.

[Synthesis of Host Material Compound 1H]:

A synthesis scheme of Compound 1H is shown below.

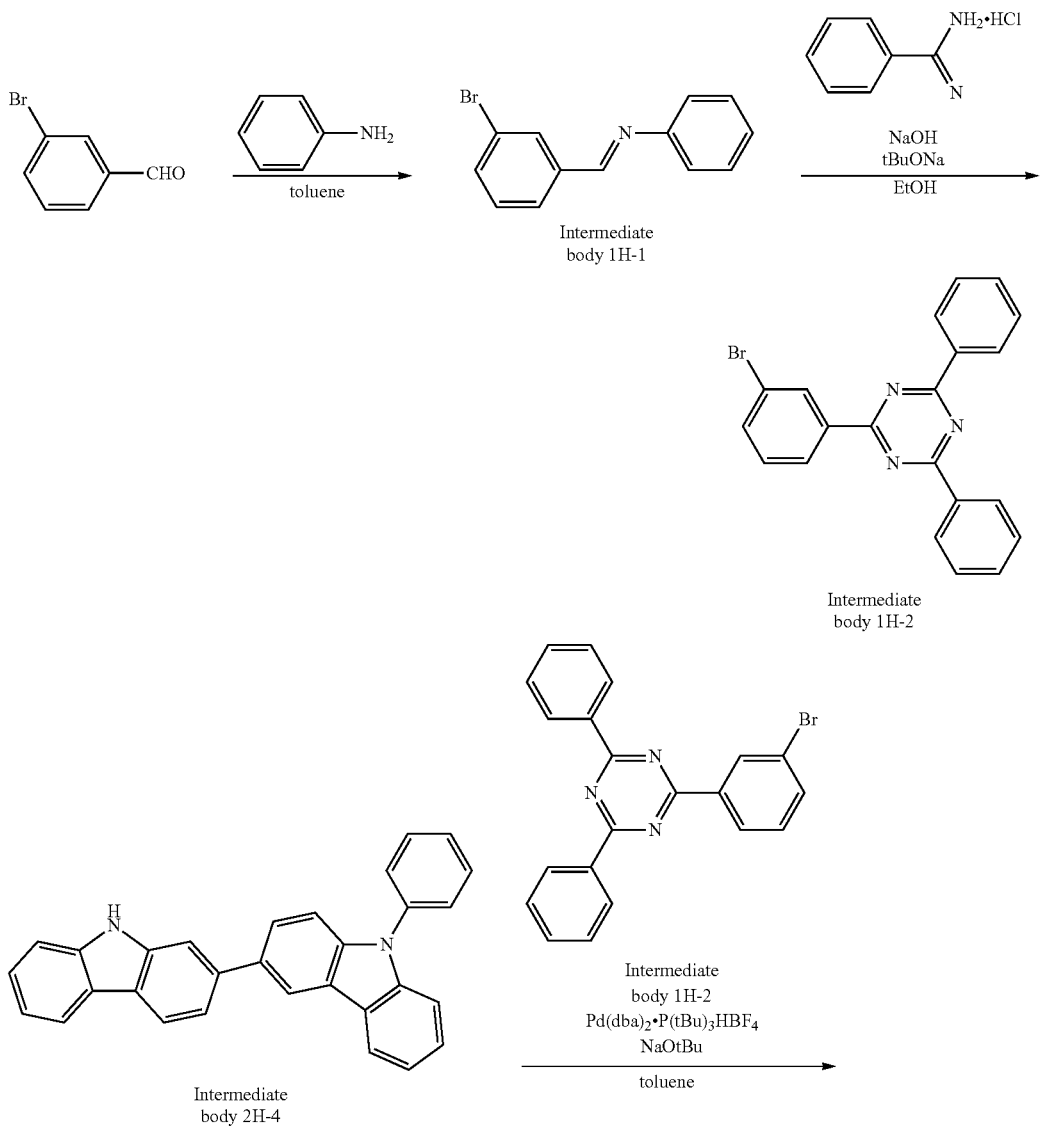

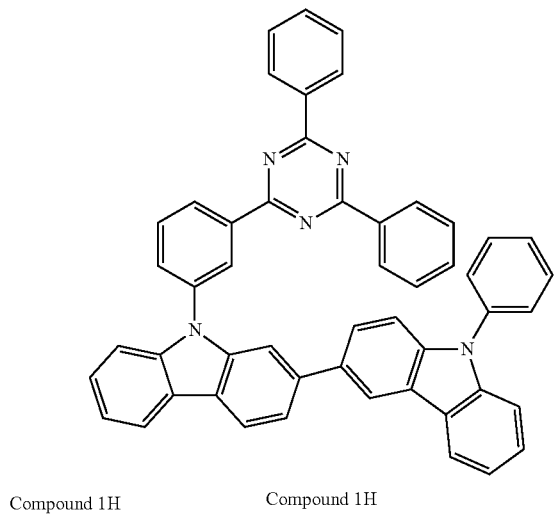

Compound 1H    Compound 1H 3-bromobenzaldehydro (100 g, 54 mmol) and aniline (50 g, 54 mmol) were added to toluene (1 L) and heated to reflux for 8 hours. After the reaction solution was cooled down, a solvent was concentrated under reduced pressure to obtain an intermediate body 1H-1 (130 g, a yield of 93%).

Subsequently, under an argon gas atmosphere, the intermediate body 1C-1 (130 g, 50 mmol), benzamidine hydrochloride (152 g, 100 mmol), anhydrous ethanol (1 L), and sodium hydroxide (42 g) were added together in sequential order, and stirred at 80 degrees C. for 16 hours. Subsequently, sodium-t-butoxide (20 g, 208 mmol) were further added and heated at 80 degrees C. for 16 hours with stirring. After the reaction solution was cooled down, a solid was separated by filtration and washed with methanol to obtain an intermediate body 1H-2 (67 g, a yield of 37%).

Under an argon gas atmosphere, the intermediate body 1-4 (1.6 g, 3.9 mmol), the intermediate body 1H-2 (1.5 g, 3.9 mmol), tris(dibenzylideneacetone)dipalladium (0.071 g, 0.078 mmol), tri-t-butylphosphonium tetrafluoroborate (0.091 g, 0.31 mmol), sodium t-butoxide (0.53 g, 5.5 mmol), and anhydrous toluene (20 mL) were sequentially mixed, and heated to reflux for 8 hours.

After the reaction solution was cooled down to the room temperature, an organic layer was removed and an organic solvent was distilled away under reduced pressure. The obtained residue was refined by silica-gel column chromatography, whereby a compound 1H (2.3 g, a yield of 82%) was obtained.

FD-MS analysis consequently showed that m/e was equal to 715 while a calculated molecular weight was 715.

[Synthesis of Host Material Compound 2H]:

A synthesis scheme of the compound 2H is shown below.

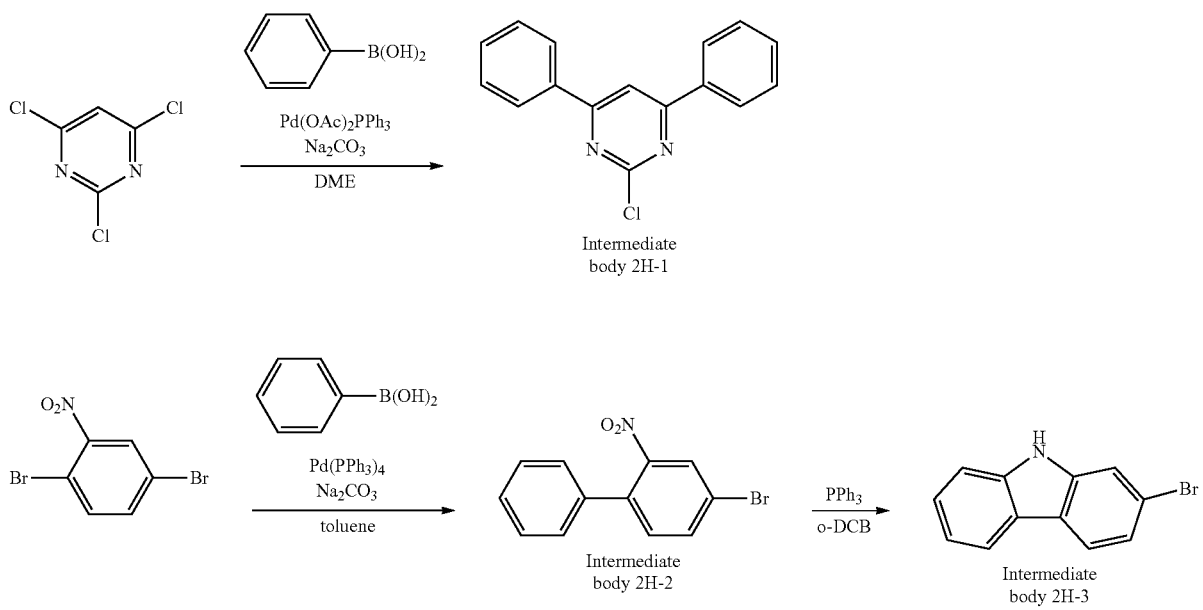

-continued

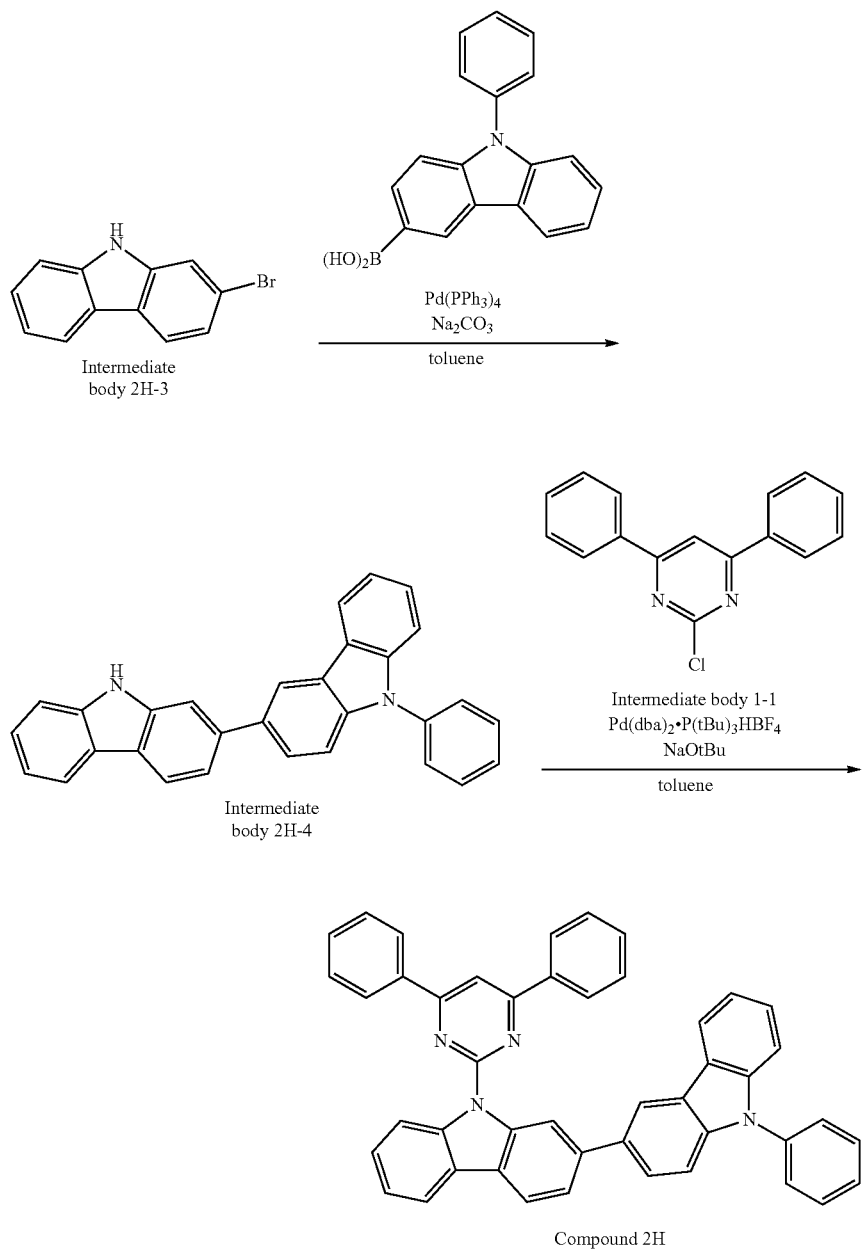

Under a nitrogen atmosphere, trichloropyrimidine (10 g, 54.5 mmol), phenylboronic acid (13.3 g, 109 mmol), palladium acetate (0.3 g, 1.37 mmol), triphenylphosphine (0.72 g, 2.73 mmol), dimethoxyethane (150 mL) and an aqueous solution of 2M sodium carbonate (170 mL) were added together in sequential order, and heated to reflux for 8 hours.

After the reaction solution was cooled down to the room temperature, an organic layer was removed and an organic solvent was distilled away under reduced pressure. The obtained residue was refined by silica-gel column chromatography, whereby an intermediate body 2H-1 (9.2 g, a yield of 63%) was obtained Under a nitrogen atmosphere, 2-nitro-1,4-dibromobenzene (11.2 g, 40 mmol), phenylboronic acid (4.9 g, 40 mmol), tetrakis(triphenylphosphine)palladium (1.39 g, 1.2 mmol), toluene (120 mL) and an aqueous solution of 2M sodium carbonate (60 mL) were added together in sequential order, and heated to reflux for 8 hours.

After the reaction solution was cooled down to the room temperature, an organic layer was removed and an organic solvent was distilled away under reduced pressure. The obtained residue was refined by silica-gel column chromatography, whereby an intermediate body 2H-2 (6.6 g, a yield of 59%) was obtained.

Subsequently, under an argon gas atmosphere, the intermediate body 7-2 (6.6 g, 23.7 mmol), triphenylphosphine (15.6 g, 59.3 mmol), and o-dichlorobenzene (24 mL) were added together in sequential order, and heated to reflux at 180 degrees C. for 8 hours.

After cooled down to the room temperature, the reaction solution was refined by silica-gel column chromatography, whereby an intermediate body 2H-3 (4 g, a yield of 68%) was obtained.

Under a nitrogen atmosphere, the intermediate body 2H-3 (4 g, 16 mmol), N-phenylcarbazolyl-3-boronic acid (5.1 g, 17.8 mmol), tetrakis(triphenylphosphine)palladium (0.56 g, 0.48 mmol), toluene (50 mL) and an aqueous solution of 2M sodium carbonate (24 mL) were added together in sequential order, and heated to reflux for 8 hours.

After the reaction solution was cooled down to the room temperature, an organic layer was removed and an organic solvent was distilled away under reduced pressure. The obtained residue was refined by silica-gel column chromatography, whereby an intermediate body 2H-4 (3.2 g, a yield of 49%) was obtained.

Under an argon gas atmosphere, the intermediate body 2H-4 (1.6 g, 3.9 mmol), the intermediate body 2H-1 (1.0 g, 3.9 mmol), tris(dibenzylideneacetone)dipalladium (0.071 g, 0.078 mmol), tri-t-butylphosphonium tetrafluoroborate (0.091 g, 0.31 mmol), sodium t-butoxide (0.53 g, 5.5 mmol), and anhydrous toluene (20 mL) were sequentially mixed, and heated to reflux for 8 hours.

After the reaction solution was cooled down to the room temperature, an organic layer was removed and an organic solvent was distilled away under reduced pressure. The obtained residue was refined by silica-gel column chromatography, whereby a compound 2H (2.4 g, a yield of 95%) was obtained.

FD-MS analysis consequently showed that m/e was equal to 638 while a calculated molecular weight was 638.

[Synthesis of the Host Material Compound 3H]:

A synthesis scheme of the Compound 3H is shown below.

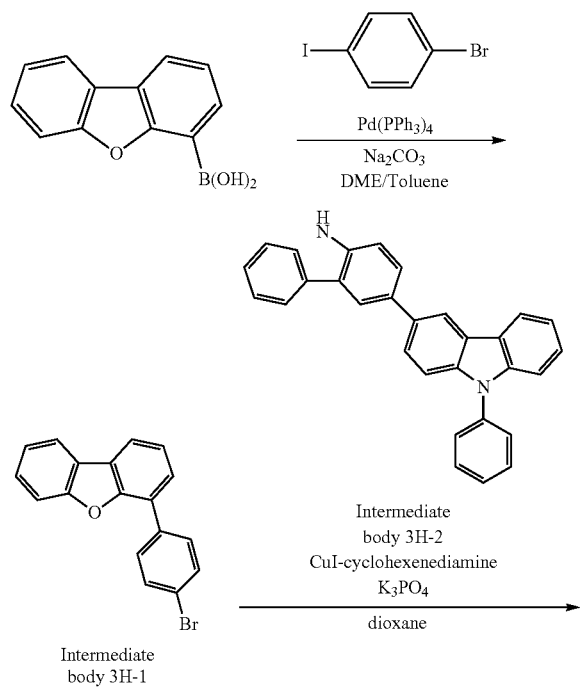

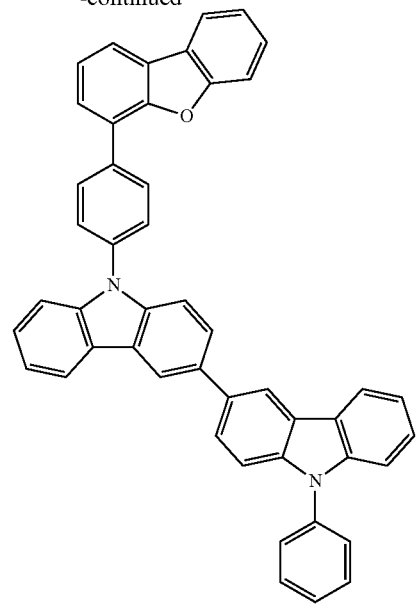

Compound 3H

Under an argon atmosphere, toluene (150 mL), dimethoxyethane (150 mL), and an aqueous solution of sodium carbonate having a concentration of 2 M (150 mL) were added to 4-iodobromobenzene (28.3 g, 100.0 mmol), dibenzofuran-4-boronic acid (22.3 g, 105 mmol), and tetrakis(triphenylphosphine)palladium(0) (2.31 g, 2.00 mmol), and then the mixture was heated for 10 hours while being refluxed.

Immediately after the completion of the reaction, the resultant was filtrated, and then the aqueous layer was removed. The organic layer was dried with sodium sulfate, and was then concentrated. The residue was purified by silica gel column chromatography. Thus, an intermediate body 3H-1 (26.2 g, 81% yield) was obtained. FD-MS (field desorption mass spectrometry) analysis confirmed that the intermediate had a ratio m/e of 322 with respect to its molecular weight, i.e., 322.

Under an argon atmosphere, the intermediate body 3H-1 (2.36 g, 7.3 mmol), an intermediate body 3H-2 (3.0 g, 7.3 mmol), CuI (1.4 g, 7.3 mmol), tripotassium phosphate (2.3 g, 11 mmol), anhydrous dioxane (30 mL), and cyclohexanediamine (0.84 g, 7.3 mmol) were loaded in the stated order into a three-necked flask, and were then stirred at 100° C. for 8 hours.

Water was added to the reaction liquid to precipitate a solid, and then the solid was washed with hexane and then with methanol. Further, the resultant solid was purified by silica gel column chromatography. Thus, a compound 3H (2.9 g, 60% yield) was obtained. The result of FD-MS analysis confirmed that the compound had a ratio m/e of 650 with respect to its molecular weight, i.e., 650.

[Example Synthesis Information for the Phosphorescent Compound 4B]:

The phosphorescent dopant Compound 4B was synthesized as follows:

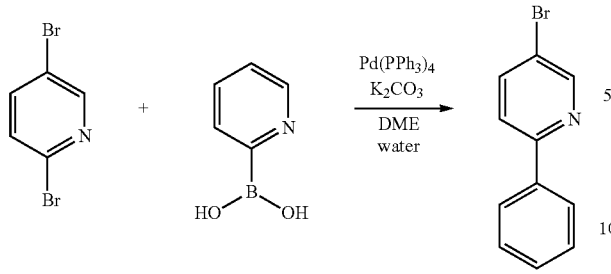

Synthesis of 2-phenyl-5-bromopyridine

A mixture is prepared of 2,5-dibromopyridine (10 g, 42.21 mmol), phenylboronic acid (5.1 g, 42.21 mmol), and potassium carbonate (11.7 g, 84.42 mmol) in 100 mL dimethoxyethane and 40 mL of water. Nitrogen is bubbled directly into the mixture for 30 minutes. Next, tetrakis (triphenylphosphine)palladium(0) was added (244 mg, 2.11 mmol) and the mixture is heated to reflux under nitrogen overnight. The mixture is cooled and diluted with ethyl acetate and water. The layers are separated and the aqueous layer is extracted with ethyl acetate. The organic layers are washed with brine, dried over magnesium sulfate, filtered, and evaporated to a residue. The residue is purified by column chromatography eluting with 0, 2, and 5% ethyl acetate/hexanes.

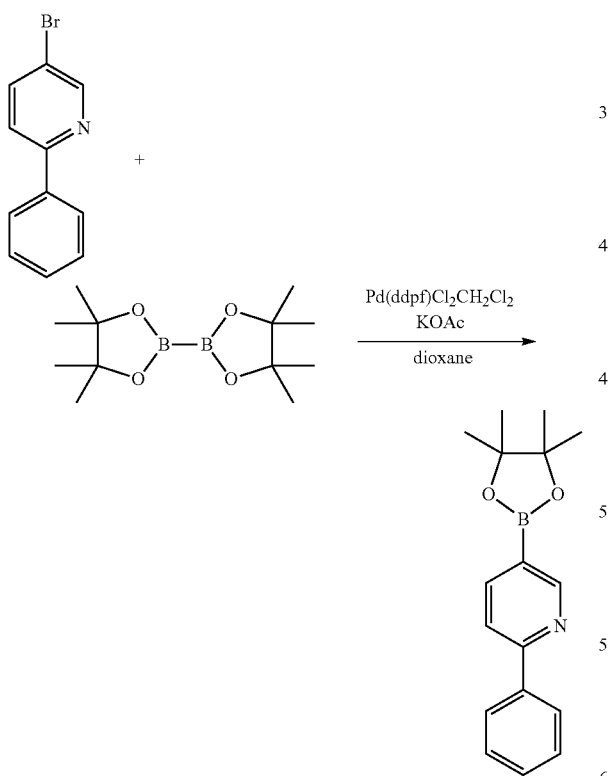

Synthesis of 2-phenyl-5-(4,4,5,5-tetramethyl-1,3,2-dioxaborolan-2-yl)pyridine A mixture is prepared of 2-phenyl-4-bromopyridine (4.28 g, 18.28 mmol), bis(pinacolato)diboron (9.29 g, 36.57 mmol), and potassium acetate (5.38 g, 54.84 mmol) in 100 mL of dioxane. Nitrogen is bubbled directly into the mixture for 30 minutes. Dichloro[1,1'-ferrocenylbis(diphenylphosphine)]palladium(II) dichloromethane (448 mg, 0.55 mmol) is added. The reaction mixture is heated to 90° C. internally for 3 h. The solvent is evaporated to an oil. The oil was purified by Kugelrohr to remove excess bis(pinacolato) diboron. The residue left in the boiling pot is dissolved in ethyl acetate and filtered through magnesium sulfate, rinsed with ethyl acetate, and the filtrate is evaporated. The product can be used without purification in the next step.

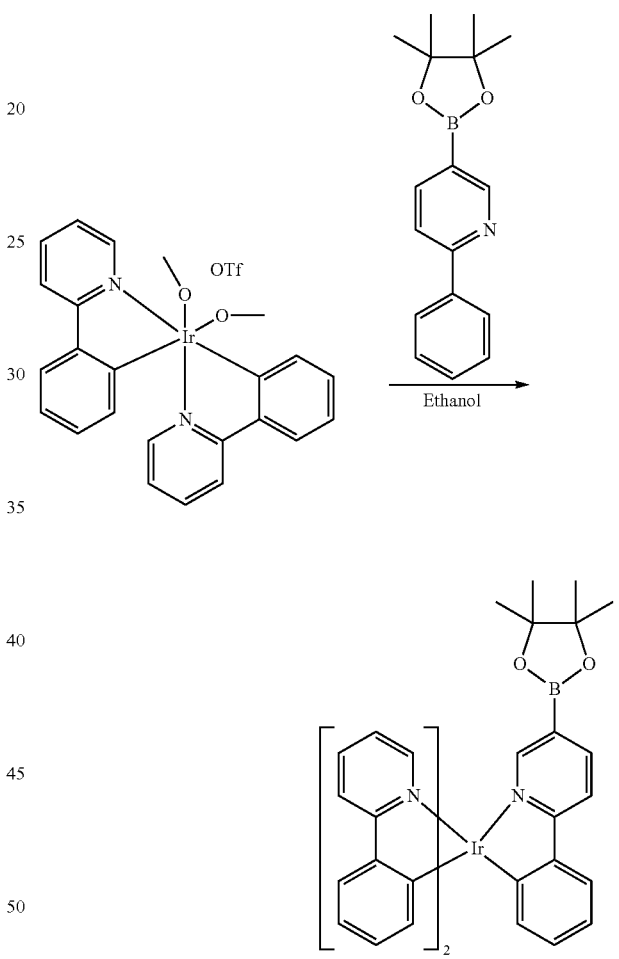

Synthesis of Boronic Ester Precursor

A mixture is prepared of the triflate (4.6 g, 7.11 mmol) and 2-phenyl-5-(4,4,5,5-tetramethyl-1,3,2-dioxaborolan-2yl) pyridine (4 g, 14.23 mmol) in 100 mL of ethanol. The mixture is heated at reflux for 24 h under nitrogen. The solvent is evaporated and hexanes is added. A sold is filtered off which is washed with hexanes. The solid is purified by column chromatography eluting with dichloromethane and later some methanol is added.

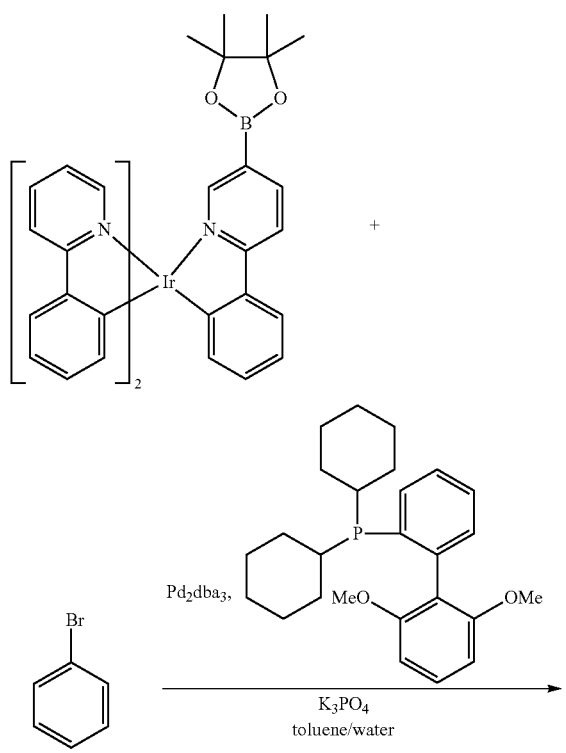

Synthesis of Compound 4B

The boronic ester precursor (0.92 g, 1.18 mmol), bromobenzene (0.6 g, 3.54 mmol), 2-dicyclohexylphosphino-2′,6′-dimethoxybiphenyl (19 mg, 0.047 mmol), and potassium phosphate tribasic (0.82 g, 3.54 mmol) are mixed in 50 mL of tolune and 5 mL of water. Nitrogen is bubbled directly into the mixture for 30 minutes after which tris(dibenzylideneacetone)dipalladium(0) (11 mg, 0.0118 mmol) is added. Nitrogen is bubbled for another 5 minutes then the reaction mixture is heated to reflux for 1 h under nitrogen. The mixture is cooled and an orange solid formed. The solid is filtered off and washed with hexanes followed by methanol. The solid is purified by column chromatography eluting with 50% dichloromethane/hexanes.

The green phosphorescent dopant Compound 4B was synthesized in an alternative method as follows:

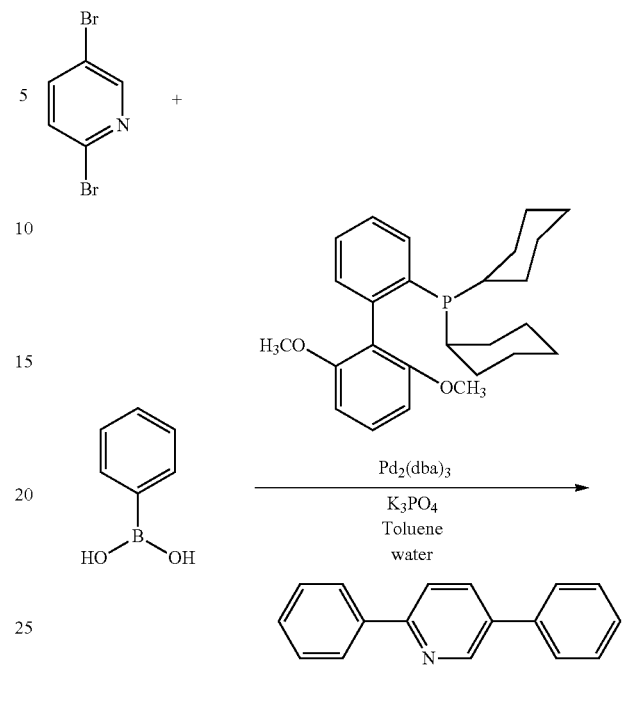

Synthesis of 2, 5-diphenylpyridine 2,5-dibromopyridine (10 g, 42 mmol), phenylboronic acid (13.4 g, 110 mmol), dicyclohexyl(2′,6′-dimethoxybiphenyl-2-yl)phosphine (S-Phos) (0.7 g, 1.6 mmol), and potassium phosphate (22 g, 105 mmol) were mixed in 200 mL of toluene and 20 mL of water. Nitrogen is bubbled directly into the mixture for 30 minutes. Next, Pd$_2$(dba)$_3$ was added (0.38 g, 0.4 mmol) and the mixture was heated to reflux under nitrogen for 2 h. The mixture was cooled and the organic layer was separated. The organic layers are washed with brine, dried over magnesium sulfate, filtered, and evaporated to a residue. The residue was purified by column chromatography eluting with 10% ethyl acetate/hexanes. 7 g of desired product was obtained after purification. (91.8% yield).

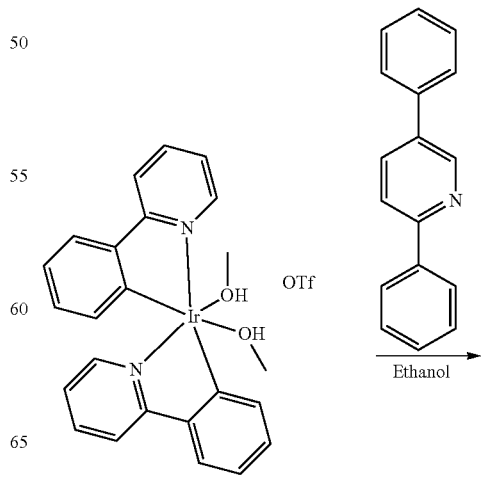

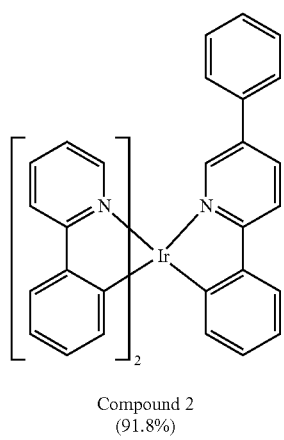

Compound 2
(91.8%)

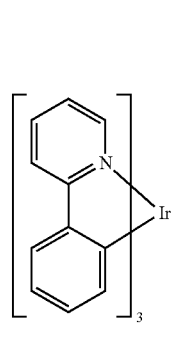

(3.1%)

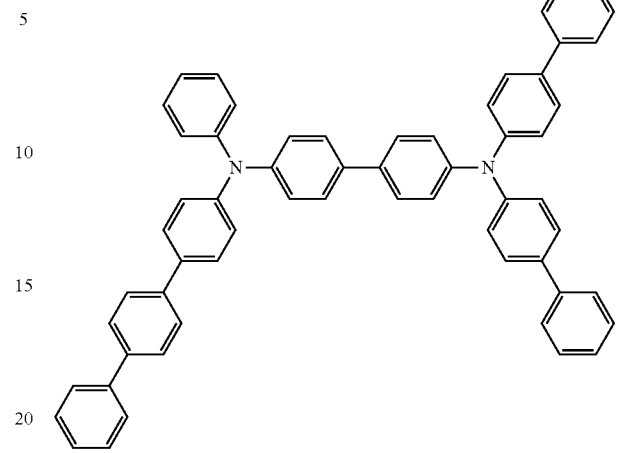

Compound HT-1

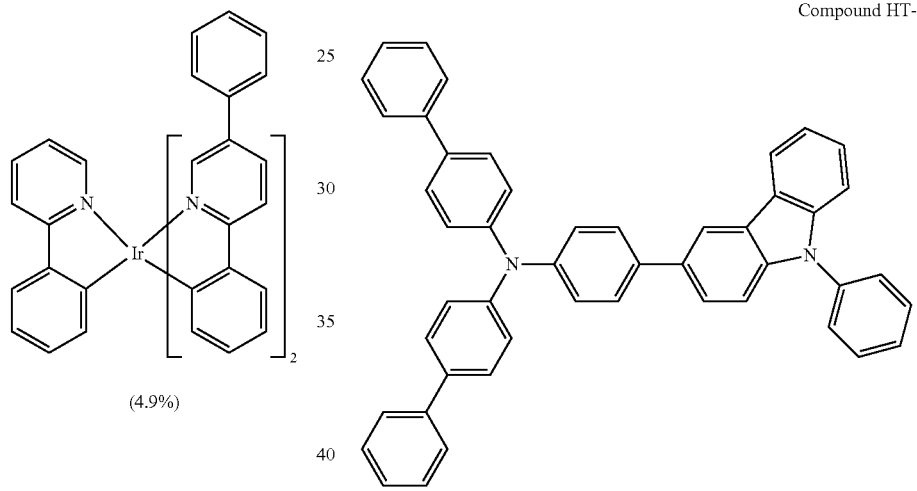

(4.9%)

Compound HT-2

Synthesis of Compound 4B

The iridium triflate precursor (2.5 g, 3.5 mmol) and 2,5-diphenylpyridine (2.4 g, 11 mmol) were mixed in 200 mL of ethanol. The mixture was heated at reflux for 24 h under nitrogen. Precipitate formed during reflux. The reaction mixture was filtered through a celite bed. The product was washed with methanol and hexanes. The solid was dissolved in dichloromethane and purified by column using 1:1 of dichloromethane and hexanes. 1.2 g of pure product was obtained after the column purification. (HPLC purity: 99.8%)

[Device Data]

The invention will be described in further detail with reference to some example devices and reference devices. However, the invention is not limited by the description of the examples.

The compounds including 1H, 2H, 3H and 4B are described above. Other compounds used in the examples are shown as follows.

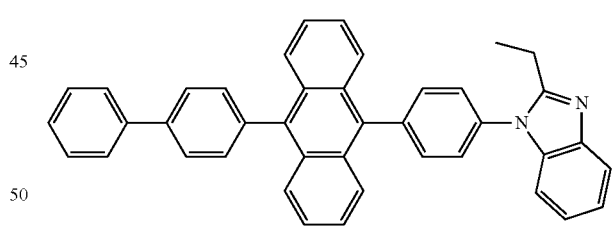

Compound ET-1

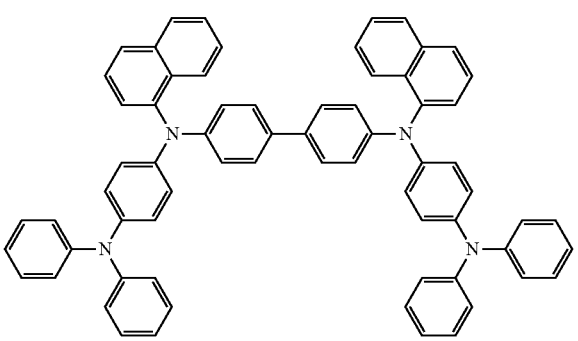

Compound HI-1

[Manufacture of Organic EL Device Having Single Host—Example Device #1]

A glass substrate (size: 25 mm×75 mm×1.1 mm) having an ITO transparent electrode (anode) of 130 nm in thickness (manufactured by Geomatec Co., Ltd.) was ultrasonic-cleaned in isopropyl alcohol for five minutes, and then UV (Ultraviolet)/ozone-cleaned for 30 minutes. After the glass substrate having the transparent electrode was cleaned, the glass substrate was mounted on a substrate holder of a vacuum deposition apparatus.

A hole injection layer was initially formed by vapor-depositing a 20 nm thick Compound HI-1 to cover the surface of the glass substrate where a transparent electrode line was provided so as to cover the transparent electrode. A hole transporting layer was formed by sequentially vapor-depositing a 30 nm thick Compound HT-1 and 20 nm thick Compound HT-2 over the electron blocking layer.

A phosphorescence-emitting layer was obtained by co-depositing the Compound 1H used as a phosphorescent host material and Compound 4B used as a phosphorescent dopant material (green phosphorescent emitter) onto the hole transporting layer (HT-2) in a thickness of 40 nm. The concentration of Compound 4B was 10 mass % and the concentration of the host material was set at 90% mass %.

Subsequently, a 30 nm thick electron transporting layer was formed by vapor-depositing Compound ET-1. A 1 nm thick LiF layer and a 80 nm thick metal Al layer were sequentially formed to obtain a cathode. A LiF layer, which is an electron injectable electrode, was formed at a speed of 1 Å/min.

[Manufacture of Organic EL Device Having Single Host—Example Device #2]

The Example Device #2 was prepared in the same manner as Example Device #1 except that Compound 2H was used as the phosphorescent host material instead of Compound 1H.

[Manufacture of Organic EL Device Having Single Host—Reference Device #1]

The Reference Device #1 was prepared in the same manner as Example Device #1 except that CBP (4,4'-bis(N-carbazolyl)biphenyl) was use as the phosphorescent host material instead of Compound 1H.

[Manufacture of Organic EL Device Having Single Host—Reference Device #2]

The Reference Device #2 was prepared in the same manner as Example Device #1 except that Ir(ppy)$_3$ was use as the phosphorescent dopant material instead of Compound 4B.

[Manufacture of Organic EL Device Having Single Host—Reference Device #3]

The Reference Device #3 was prepared in the same manner as Example Device #2 except that Ir(ppy)$_3$ was use as the phosphorescent dopant material instead of Compound 4B.

[Manufacture of Organic EL Device Having Single Host—Reference Device #4]

The Reference Device #4 was prepared in the same manner as Reference Device #1 except that Ir(ppy)$_3$ was use as the phosphorescent dopant material instead of Compound 4B.

[Manufacture of Organic EL Device Having Co-Host—Example Device #3]

A glass substrate (size: 25 mm×75 mm×1.1 mm) having a 130 nm thick ITO transparent electrode (manufactured by Geomatec Co., Ltd.) was ultrasonic-cleaned in isopropyl alcohol for five minutes, and then UV (Ultraviolet)/ozone-cleaned for 30 minutes. After the glass substrate having the transparent electrode was cleaned, the glass substrate was mounted on a substrate holder of a vacuum deposition apparatus.

A hole injection layer was initially formed by vapor-depositing a 20 nm thick Compound HI-1 to cover the surface of the glass substrate where a transparent electrode line was provided so as to cover the transparent electrode. A hole transporting layer was formed by sequentially vapor-depositing a 30 nm thick Compound HT-1 and 20 nm thick Compound HT-2 over the electron blocking layer.

A phosphorescence-emitting layer was obtained by co-depositing the Compounds 1H and 2H used as phosphorescent co-host materials and Compound 4B used as a phosphorescent dopant material (green emitter) onto the hole transporting layer (HT-2) in a thickness of 40 nm. The concentration of Compound 4B was 10 mass % and the concentration of the co-host compounds 1H and 2H were 45 mass % each.

Subsequently, a 30 nm thick electron transporting layer was formed by vapor-depositing of Compound ET-1. A 1 nm thick LiF layer and a 80 nm thick metal Al layer were sequentially formed to obtain a cathode. A LiF layer, which is an electron injectable electrode, was formed at a speed of 1 Å/min.

[Manufacture of Organic EL Device Having Co-Hosts—Example Device #4]

The Example Device #4 was prepared in the same manner as Example Device #3 except that Compounds 1H and 3H were used as the phosphorescent co-host materials.

[Manufacture of Organic EL Device Having Co-Hosts—Reference Device #5]

The Reference Device #5 was prepared in the same manner as Example Device #3 except that Compounds 1H and CBP were used as the phosphorescent co-host materials.

[Manufacture of Organic EL Device Having Co-Hosts—Reference Device #6]

The Reference Device #6 was prepared in the same manner as Example Device #3 except that Ir(ppy)$_3$ was used as the phosphorescent dopant material instead of Compound 4B.

[Manufacture of Organic EL Device Having Co-Hosts—Reference Device #7]

The Reference Device #7 was prepared in the same manner as Example Device #4 except that Ir(ppy)$_3$ was used as the phosphorescent dopant material instead of Compound 4B.

[Manufacture of Organic EL Device Having Co-Hosts—Reference Device #8]

The Reference Device #8 was prepared in the same manner as Reference Device #5 except that Ir(ppy)$_3$ was used as the phosphorescent dopant material instead of Compound 4B.

[Sample Devices]

Table 1 shows the organic compounds used for the emitter dopant material and the emitter host materials in the manufacture of the Example Devices and Reference Devices evaluated by the inventors.

TABLE 1

| Devices | Emitter Dopant | Emitter Host 1 | Emitter Host 2 |
|---|---|---|---|
| Single Host devices | | | |
| Example Device #1 | Compound 4B | Compound 1H | — |
| Example Device #2 | Compound 4B | Compound 2H | — |
| Reference Device #1 | Compound 4B | CBP | — |
| Reference Device #2 | Ir(ppy)$_3$ | Compound 1H | — |
| Reference Device #3 | Ir(ppy)$_3$ | Compound 2H | — |
| Reference Device #4 | Ir(ppy)$_3$ | CBP | — |
| Co-host devices | | | |
| Example Device #3 | Compound 4B | Compound 1H | Compound 2H |
| Example Device #4 | Compound 4B | Compound 1H | Compound 3H |
| Reference Device #5 | Compound 4B | Compound 1H | CBP |
| Reference Device #6 | Ir(ppy)$_3$ | Compound 1H | Compound 2H |
| Reference Device #7 | Ir(ppy)$_3$ | Compound 1H | Compound 3H |
| Reference Device #8 | Ir(ppy)$_3$ | Compound 1H | CBP |

[Evaluation of Sample Devices]

The example organic EL devices manufactured as Example Devices #1 to #4 and Reference Devices #1 to #8 were driven by direct-current electricity of 1 or 10 mA/cm$^2$ to emit light. The emission chromaticity (CIE), the luminescence (L) and the voltage (V) were measured. Spectral-radiance spectrum was measured using a spectroradiometer (CS-1000 manufactured by Konica Minolta Holdings, Inc.). Using the measured values, the current efficiency (L/J), luminous efficiency η (lm/W) and external quantum efficiency (EQE) where obtained. External quantum efficiency (EQE) was calculated from the obtained spectrum-radiance spectrum, assuming that Lambertian radiation was carried out. The devices were driven at constant current with the initial luminance intensity of 10,000 cd/m$^2$, and time (LT95) elapsed until the luminance intensity was decreased to 95% was obtained. The results are shown in Tables 2 and 3.

Table 2 shows the performance parameters of the single-host devices, Example Devices #1 and #2 in comparison to the Reference Devices #1 to #4. The data compares the performance of the combinations of the phosphorescent Compound 4B with the host Compounds 1H and 2H against the performance of the combination of materials in the Reference Devices.

Comparing the Example Device #1 and the Reference Device #2, the combination of the host material Compound 1H and the green phosphorescent dopant Compound 4B in Example Device #1 resulted in lower voltage, longer lifetime, higher L/J and external quantum efficiency (EQE) than the combination of host material Compound 1H and phosphorescent dopant Ir(ppy)$_3$ of the Reference Device #2 at 1 mA/cm$^2$ and at 10 mA/cm$^2$.

Similarly, the combination of the host material Compound 2H and the phosphorescent dopant Compound 4B in Example Device #2 resulted in lower voltage, longer lifetime, higher L/J and EQE than the combination of the host material Compound 2H and phosphorescent dopant Ir(ppy)$_3$ of the Reference Device #3 at 1 mA/cm$^2$ and at 10 mA/cm$^2$. The data in Table 2 show that the phosphorescent Compound 4B has lower voltage, longer lifetime, higher L/J, and EQE than Ir(ppy)$_3$.

Thus, the phosphorescent Compound 4B as an emitter and Compounds 1H or 2H as a host material in the emitter region produces more efficient luminance and electrochemically longer lasting than conventional materials, such as Ir(ppy)$_3$ and CBP, in PHOLED devices.

Table 3 shows the performance parameters of the co-host devices, Example Devices #3 and #4 and the Reference Devices #5 to #8. The data compares the performance of the phosphorescent Compound 4B in combination with co-host systems, Compound 1H & 2H and Compound 1H & 3H against the performance of the combination of materials in the Reference Devices #5 to #8.

Comparing the Example Device #3 and the Reference Device #6, the combination of the phosphorescent Compound 4B with co-host Compounds 1H & 2H resulted in lower voltage, longer lifetime, higher L/J, and EQE than the combination of the phosphorescent dopant Ir(ppy)$_3$ with the co-host Compounds 1H & 2H at 1 mA/cm$^2$ and at 10 mA/cm$^2$.

Comparing the Example Device #4 and the Reference Device #7, the combination of the phosphorescent Compound 4B with co-host Compounds 1H & 3H resulted in lower voltage, longer lifetime, higher L/J, and EQE than the combination of the phosphorescent Ir(ppy)$_3$ with the co-host Compounds 1H & 3H at at 1 mA/cm$^2$ and at 10 mA/cm$^2$.

TABLE 2

Single host devices

| Sample Device | Current Density (mA/cm$^2$) | Volt. (V) | Luminance (cd/m$^2$) | L/J (cd/A) | η (lm/W) | EQE (%) | CIE x | CIE y | λp (nm) | LT95 @ 10,000 cd/m$^2$ (hrs) |
|---|---|---|---|---|---|---|---|---|---|---|
| Example Device #1 | 1 | 2.94 | 731 | 73.1 | 78.0 | 20.7 | 0.433 | 0.557 | 546 | 260 |
| | 10 | 3.87 | 6657 | 66.6 | 54.1 | 18.8 | 0.432 | 0.558 | 546 | |
| Example Device #2 | 1 | 3.00 | 593 | 59.3 | 62.2 | 16.9 | 0.434 | 0.555 | 546 | 550 |
| | 10 | 4.04 | 5503 | 55.0 | 42.8 | 15.7 | 0.434 | 0.556 | 546 | |
| Reference Device #1 | 1 | 4.37 | 208 | 20.8 | 15.0 | 5.8 | 0.429 | 0.560 | 546 | 30 |
| | 10 | 5.79 | 3874 | 38.7 | 21.0 | 10.9 | 0.430 | 0.559 | 546 | |
| Reference Device #2 | 1 | 3.02 | 522 | 52.2 | 54.3 | 14.8 | 0.352 | 0.602 | 521 | 20 |
| | 10 | 4.03 | 4334 | 43.3 | 33.8 | 12.3 | 0.348 | 0.602 | 520 | |
| Reference Device #3 | 1 | 3.05 | 525 | 52.5 | 54.0 | 14.6 | 0.331 | 0.616 | 519 | 60 |
| | 10 | 4.12 | 4774 | 47.7 | 36.4 | 13.3 | 0.331 | 0.616 | 519 | |
| Reference Device #4 | 1 | 4.55 | 77 | 7.7 | 5.3 | 2.2 | 0.320 | 0.616 | 516 | 30 |
| | 10 | 6.15 | 1336 | 13.4 | 6.8 | 3.8 | 0.24 | 0.614 | 517 | |

TABLE 3

Co-host devices

| Sample Device | Current Density (mA/cm) | Volt. (V) | Luminance (cd/m²) | L/J (cd/A) | η (lm/W) | EQE (%) | CIE x | CIE y | λp (hrs) | LT95 @ 10,000 cd/m² (hrs) |
|---|---|---|---|---|---|---|---|---|---|---|
| Example Device #3 | 1 | 2.91 | 596 | 59.6 | 64.4 | 16.7 | 0.428 | 0.561 | 545 | 770 |
|  | 10 | 3.96 | 5533 | 55.3 | 43.9 | 15.5 | 0.428 | 0.562 | 545 |  |
| Example Device #4 | 1 | 3.02 | 617 | 11.7 | 64.2 | 17.5 | 0.433 | 0.557 | 545 | 550 |
|  | 10 | 4.14 | 5785 | 57.9 | 43.9 | 16.4 | 0.432 | 0.557 | 545 |  |
| Reference Device #5 | 1 | 3.04 | 697 | 69.7 | 72 | 19.7 | 0.432 | 0.558 | 545 | 210 |
|  | 10 | 4.15 | 6299 | 63.0 | 47.7 | 17.8 | 0.431 | 0.559 | 545 |  |
| Reference Device #6 | 1 | 3.00 | 459 | 45.9 | 48.1 | 12.8 | 0.339 | 0.612 | 520 | 50 |
|  | 10 | 4.08 | 4123 | 41.2 | 31.7 | 11.5 | 0.337 | 0.613 | 520 |  |
| Reference Device #7 | 1 | 3.47 | 459 | 45.9 | 41.6 | 13.0 | 0.345 | 0.606 | 519 | 50 |
|  | 10 | 4.70 | 4177 | 41.8 | 27.9 | 11.8 | 0.343 | 0.607 | 519 |  |
| Reference Device #8 | 1 | 3.37 | 539 | 53.9 | 50.3 | 15.2 | 0.342 | 0.608 | 519 | 50 |
|  | 10 | 4.55 | 4666 | 46.7 | 32.2 | 13.2 | 0.340 | 0.607 | 519 |  |

The Tables 3 and 4 also show the LT95 data of the Example Devices #1, #2, #3, and #4 and the Reference Devices #1, #2, #3, #4, #5, #6, #7, and #8. The Example devices exhibit longer lifetime than the Reference devices. And among the Example devices that comprise the host and dopant material combinations according to the present disclosure, the co-host Example Devices #3 and 4 have longer lifetime than the single host Example Devices #1 and #2. For example, the Example Device #3 having a combination of 4B as emitter and 1H & 2H as co-hosts showed significantly longer lifetime than either the Example Device #1 (having combination of 4B and 1H) or the Example Device #2 (having combination of 4B and 1H). The Example Device #4 having a combination of 4B as emitter and 1H & 3H as co-hosts showed significantly longer lifetime than either the Example Device #1 (having combination of 4B and 1H). As discussed above, the inventors believe that this is because the co-host material combinations disclosed herein improves the carrier injecting capability to neighboring layers in the emitting layer (recombination region).

The above device data show that when the biscarbazole derivative compounds of the present disclosure are used, either as a single host or paired as co-hosts, in combination with the phosphorescent material of the family represented by compound formula 4A in a PHOLED, those combinations perform superior to PHOLED devices made from material combinations that contain the biscarbazole derivative compounds with a different phosphorescent dopant (e.g. Ir(ppy)₃) or the phosphorescent dopant compound of formula 4A with different host compounds (e.g. CBP).

The inventors believe that the combinations of the green phosphorescent compound of the formula 4B with the host material compound of the formula 1H, 2H, or 3H enhance device performance by improving charge balance and recombination. The device data discussed above show that the host material compound of the formula 2H with phosphorescent Compound 4B is superior to the Reference Device examples in terms of voltage, luminous efficacy and lifetime.

According to another aspect of the present disclosure, the scope of the invention described herein includes a lighting apparatus and/or display apparatus that incorporates one or more of the various embodiments of the organic electroluminescence devices described herein. Some examples of such display apparatus are television screens, computer display screens, mobile phone display screens, billboard screens, etc.

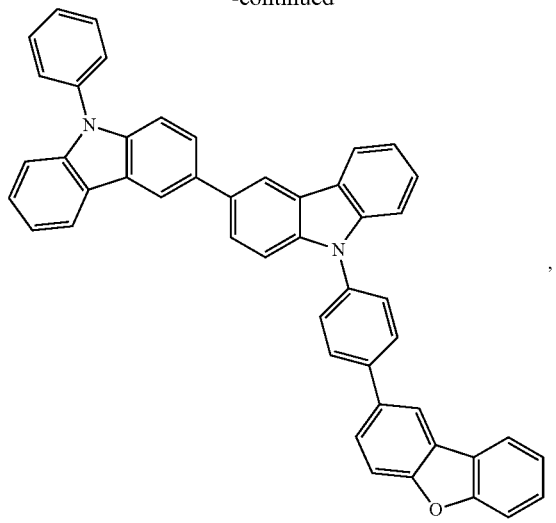
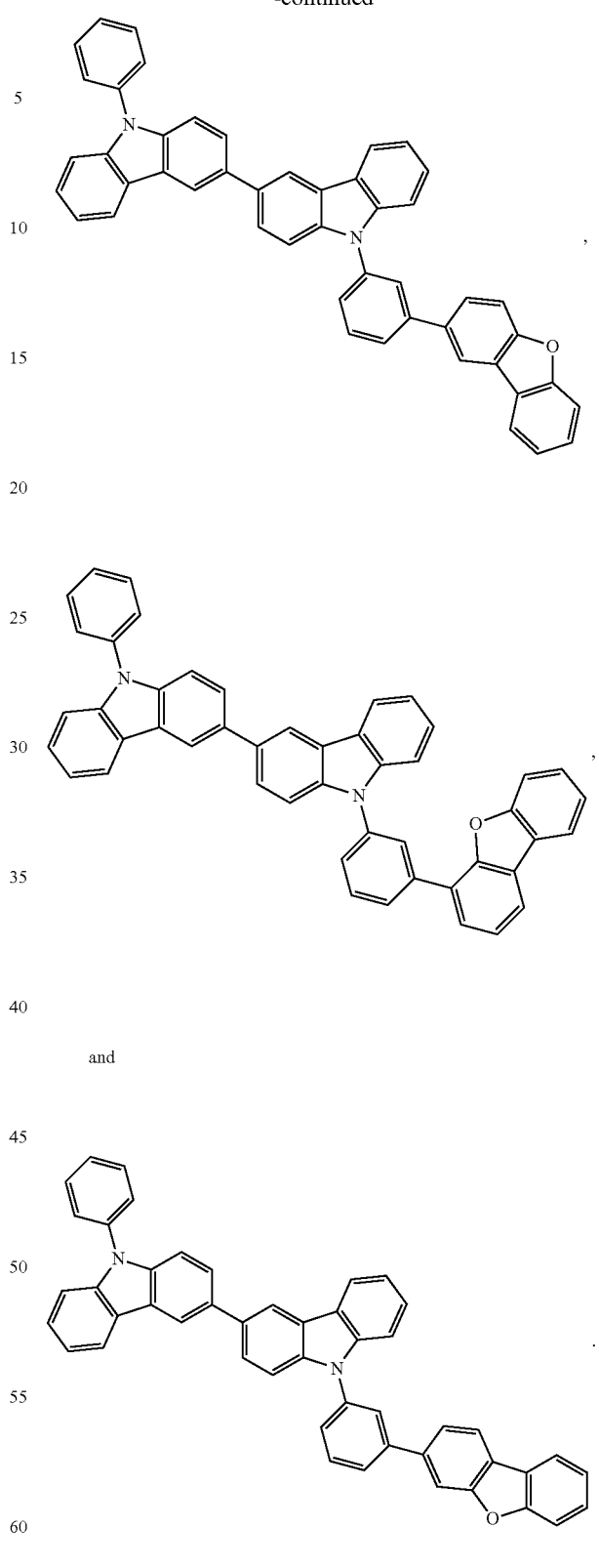

What is claimed is:

1. An organic electroluminescence device comprising:
   a cathode; an anode; and a plurality of organic thin-film layers provided between the cathode and the anode, the plurality of organic thin-film layers comprising an emitting layer,
   wherein at least one of the organic thin-film layers is the emitting layer comprising a green phosphorescent dopant material and a host material that is a biscarbazole derivative compound selected from the group consisting of

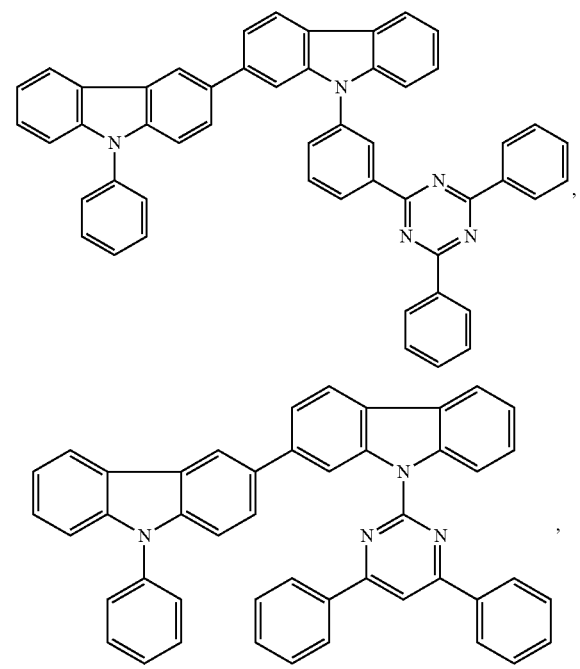

115
-continued
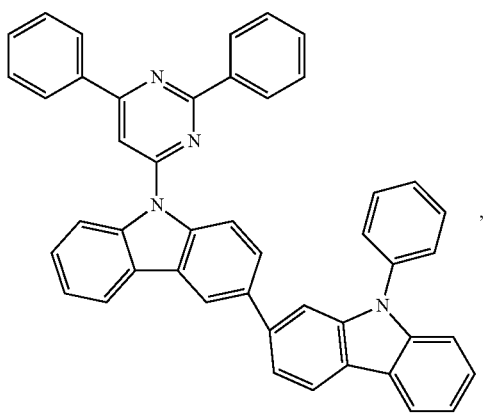
,
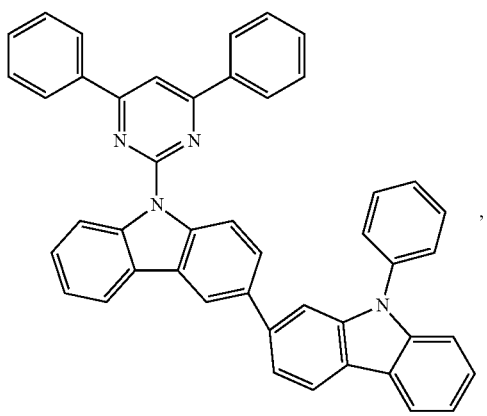
,
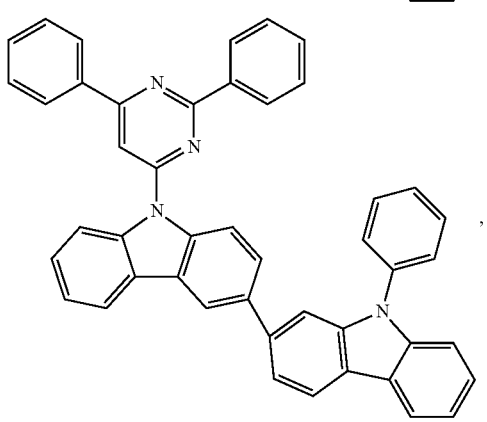
,
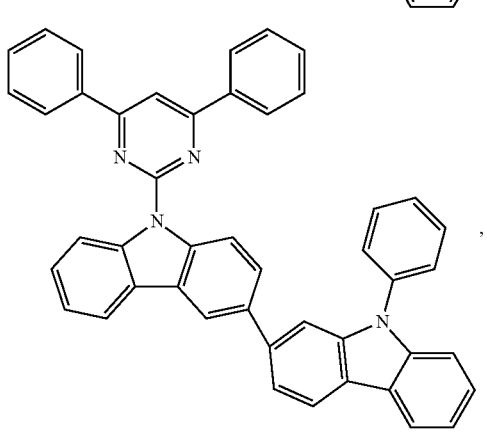
,
116
-continued
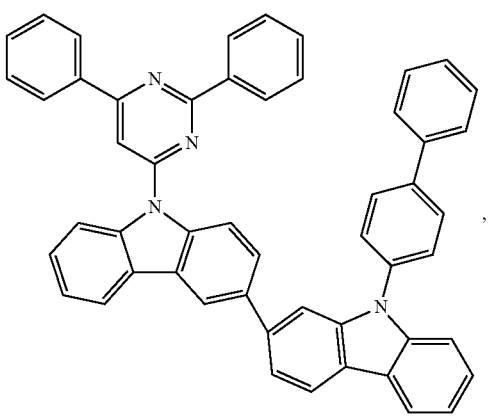
,
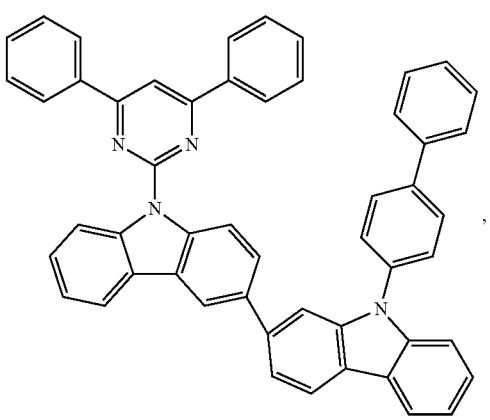
,
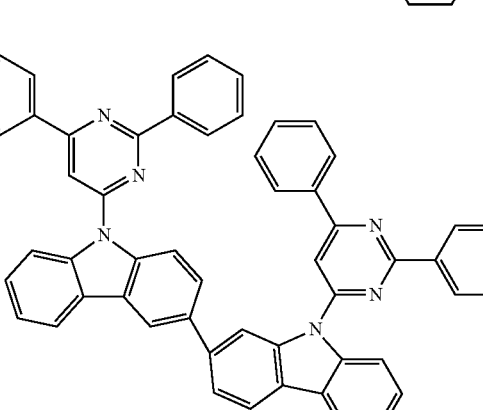
,
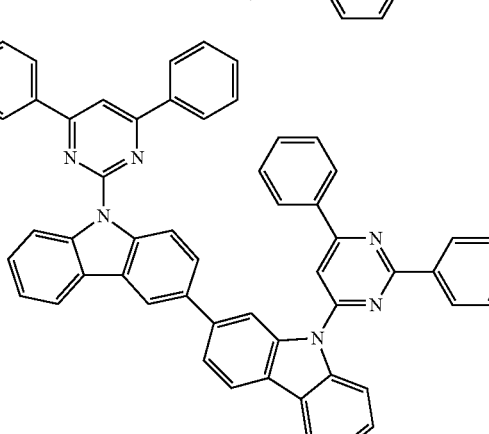
, 117
-continued
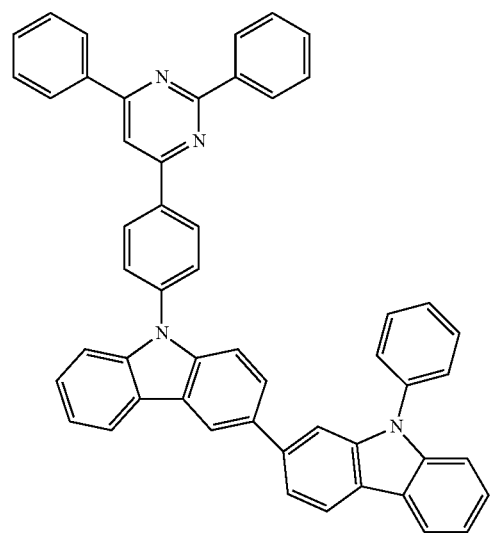
,
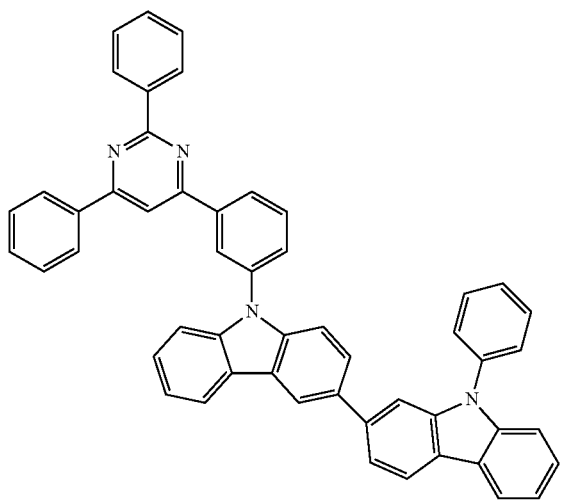
,
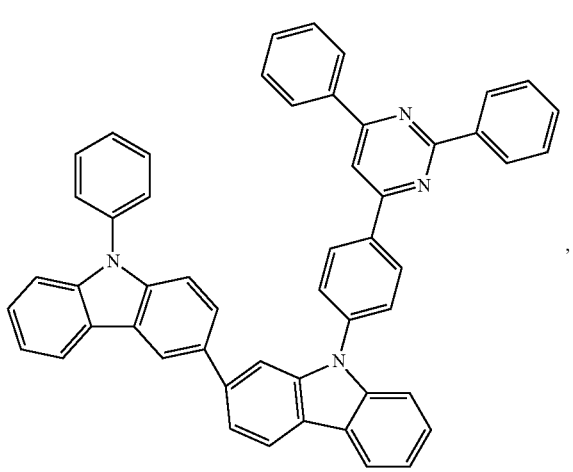
,
118
-continued
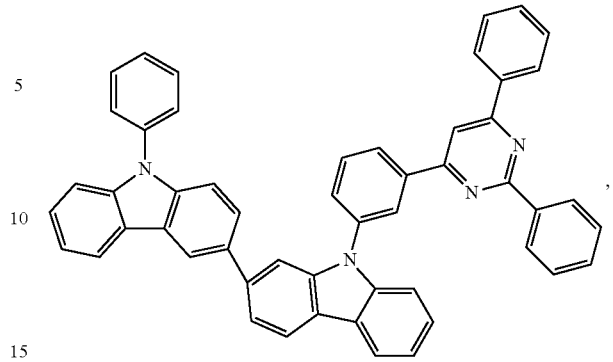
,
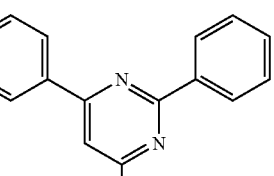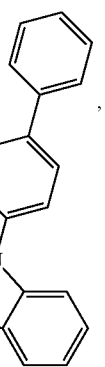
,
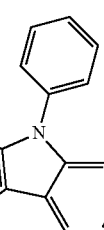
, 119
-continued
120
-continued
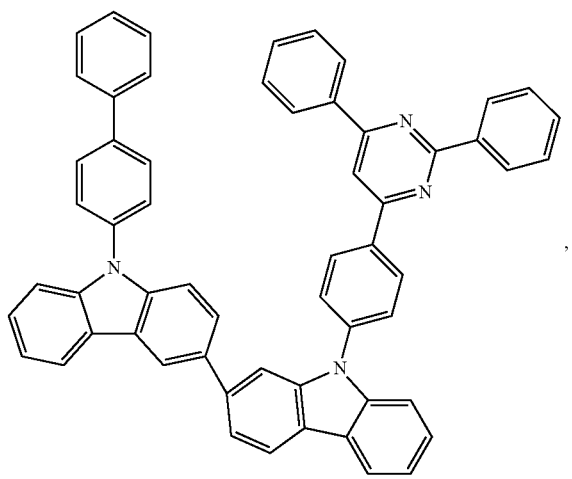
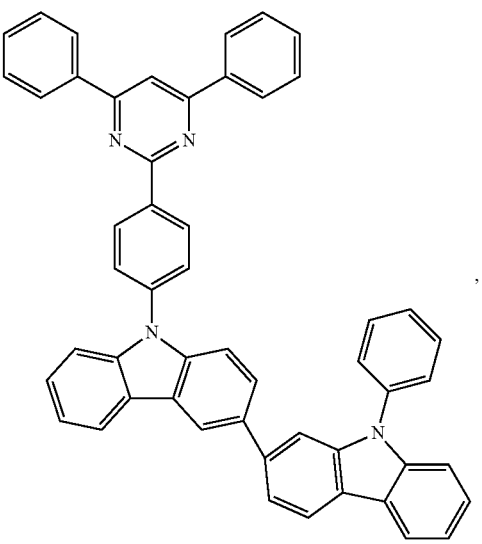
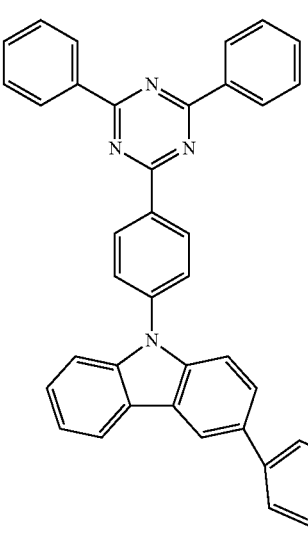
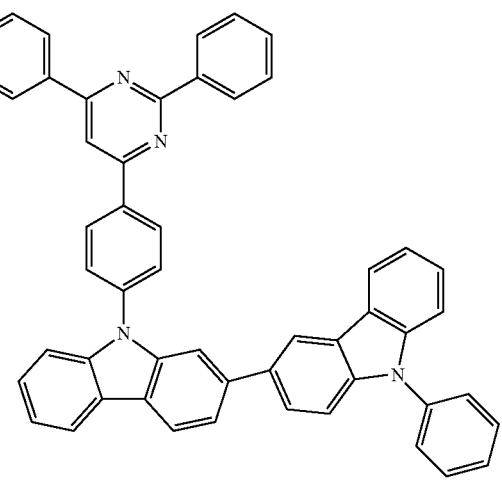

121
-continued
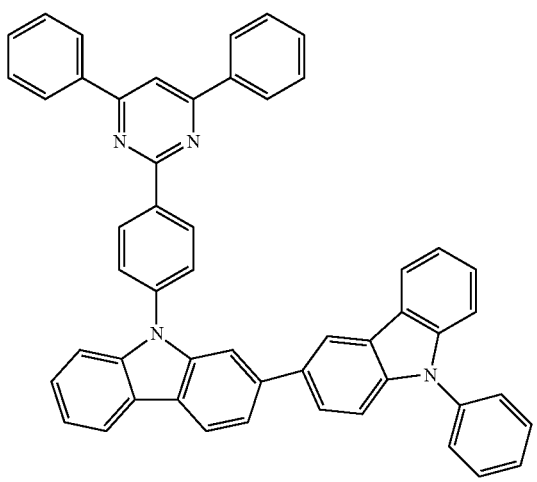
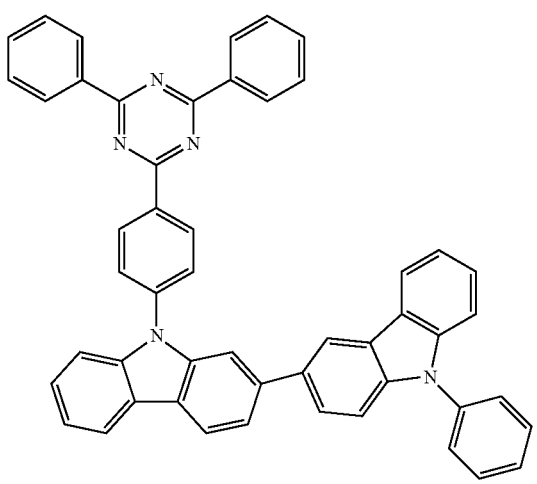
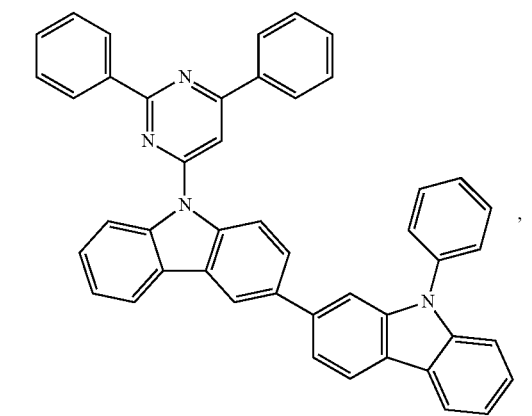
122
-continued
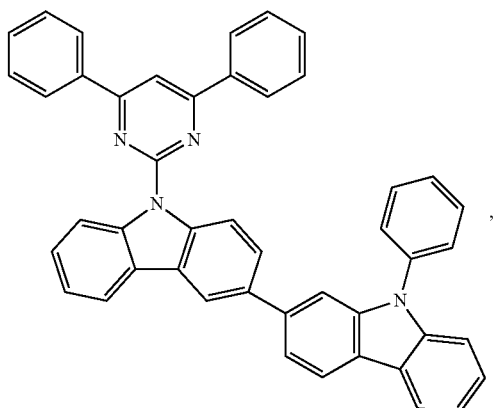
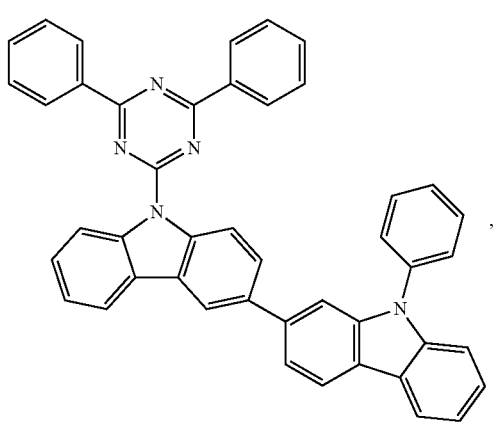
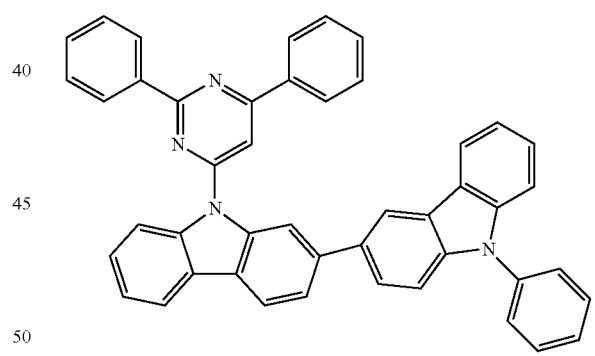
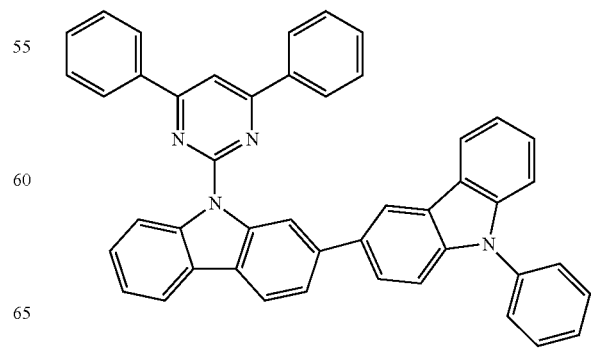

123
-continued
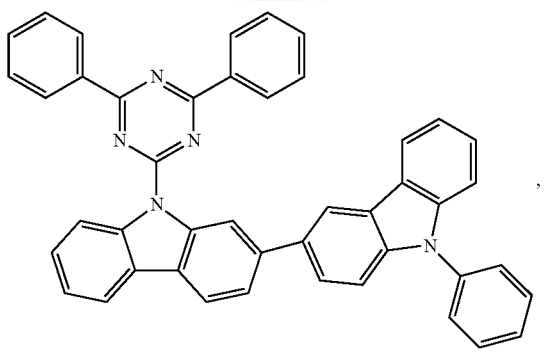
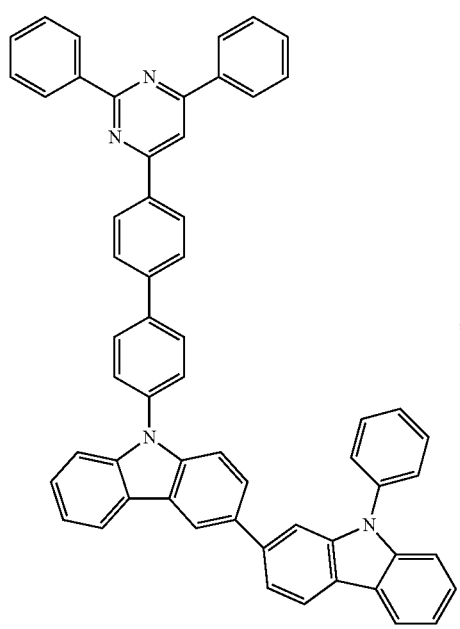
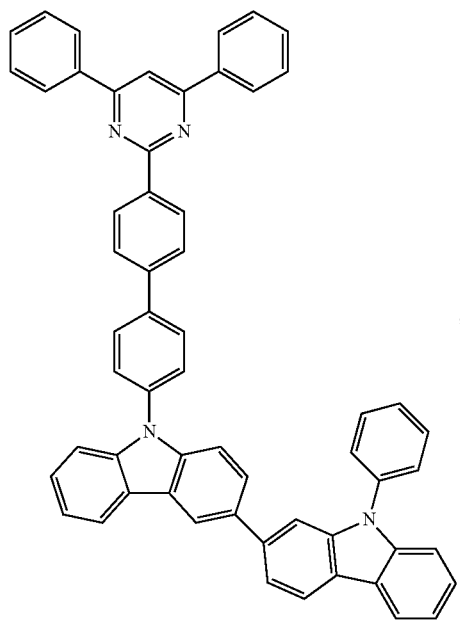
124
-continued
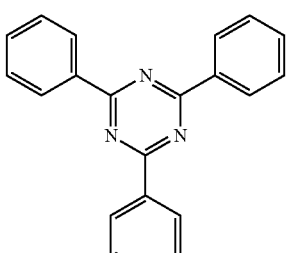
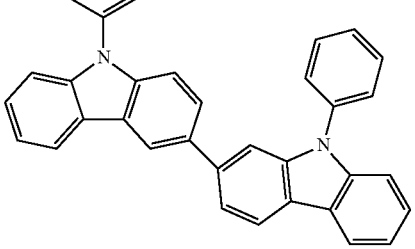
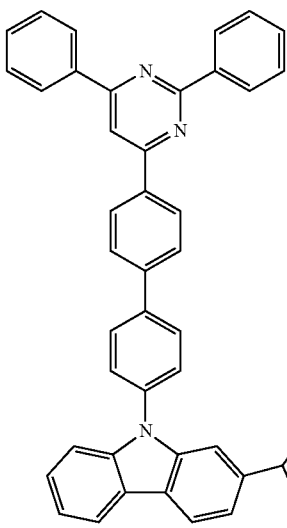

125
-continued
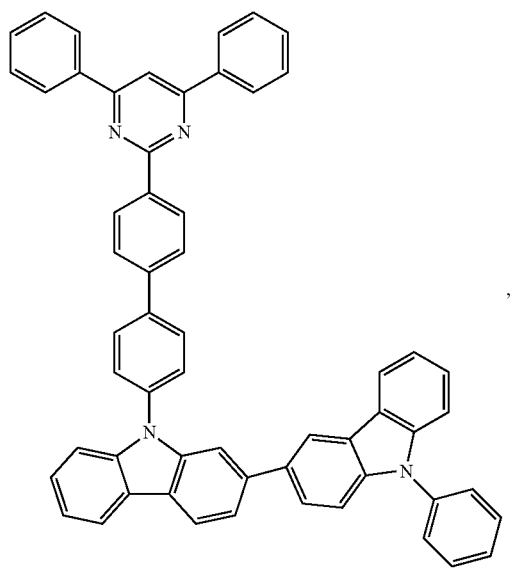
126
-continued
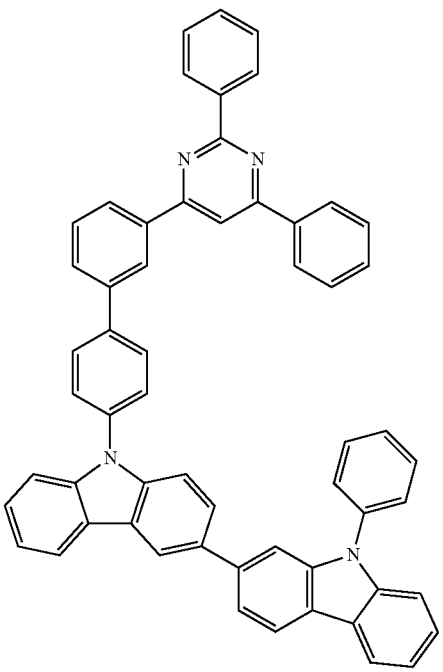
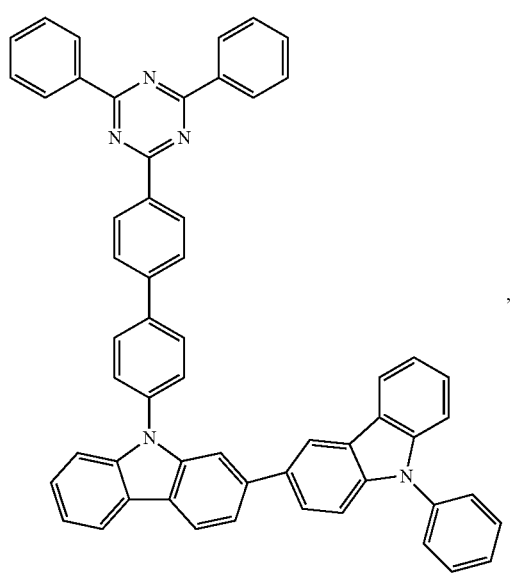

127
-continued
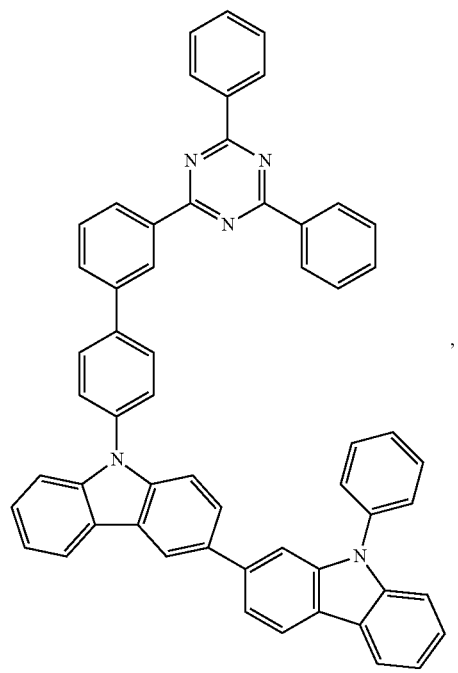
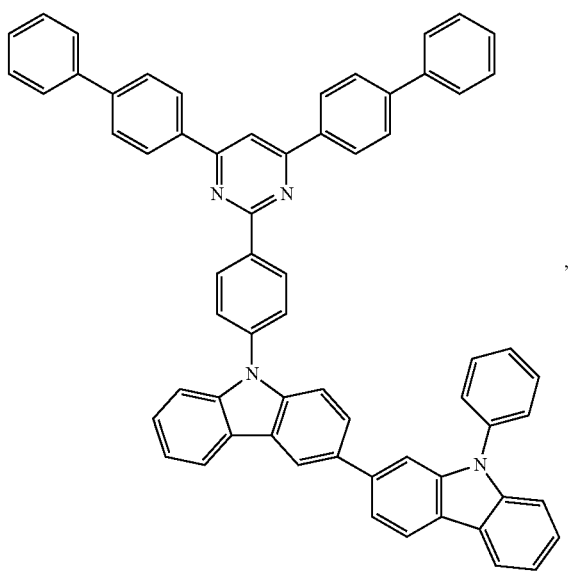
128
-continued
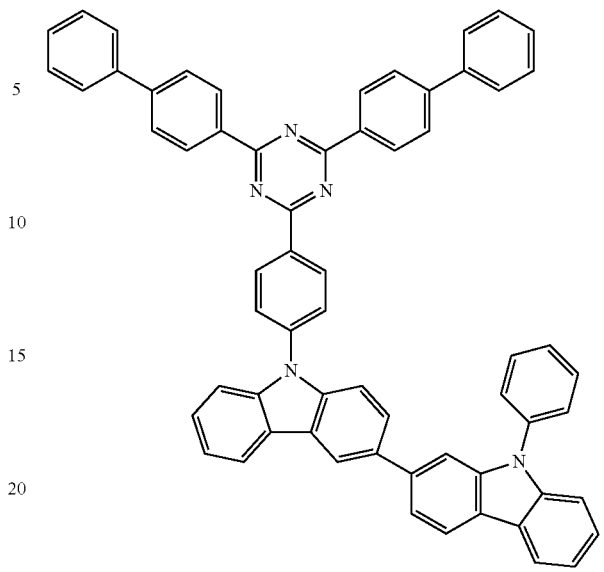
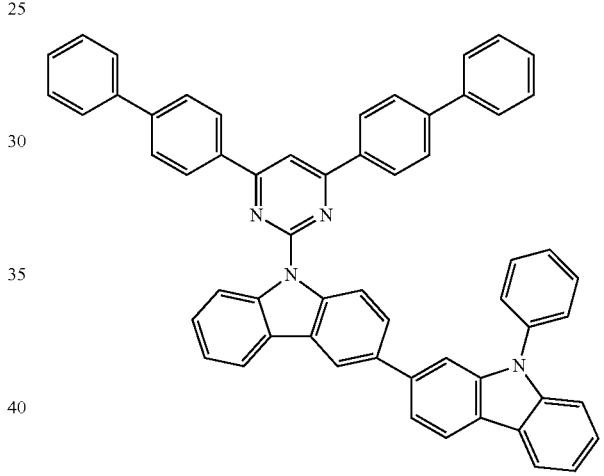
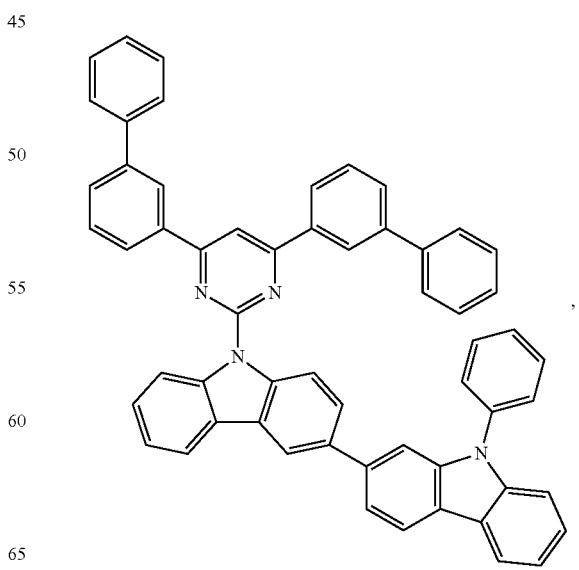

129
-continued
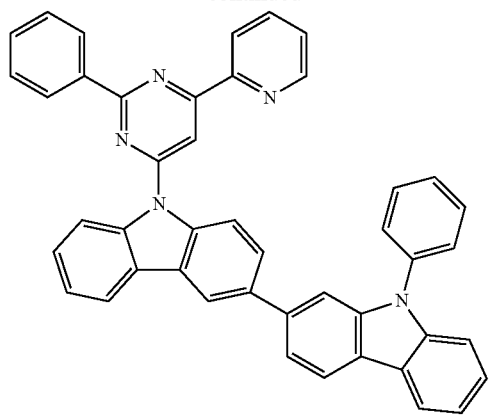
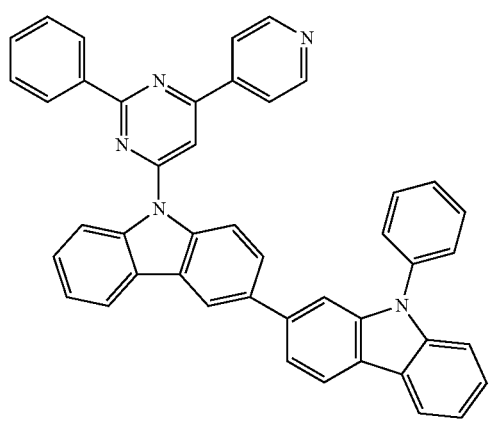
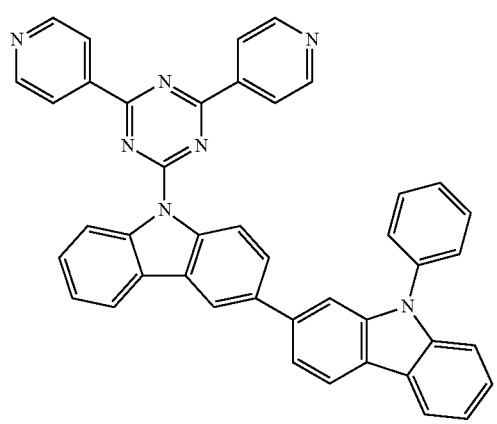
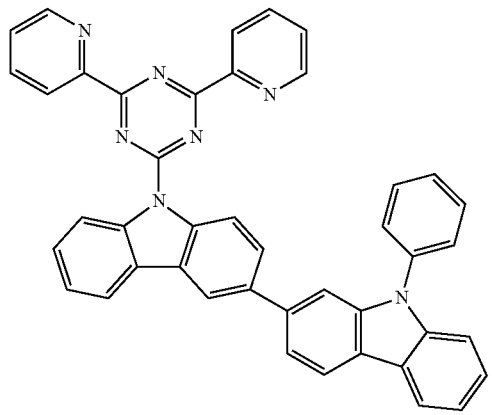
130
-continued
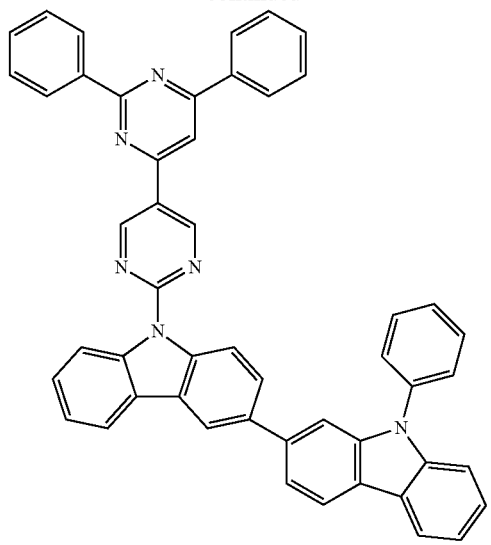
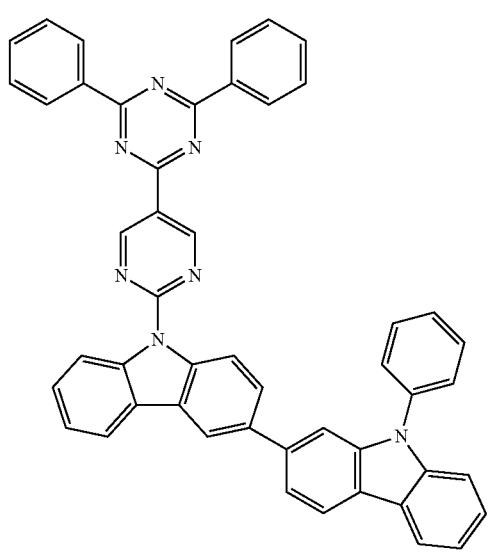
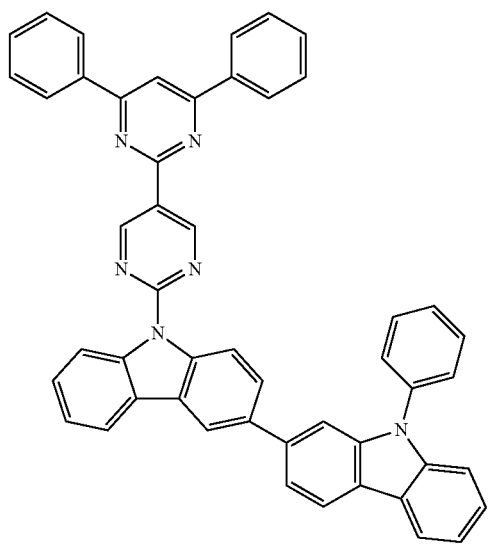

131
-continued
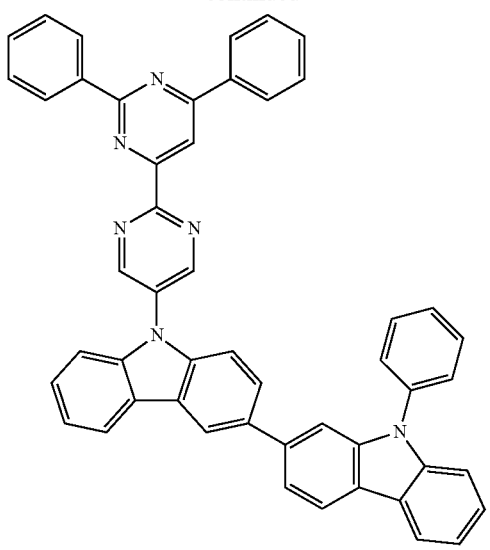
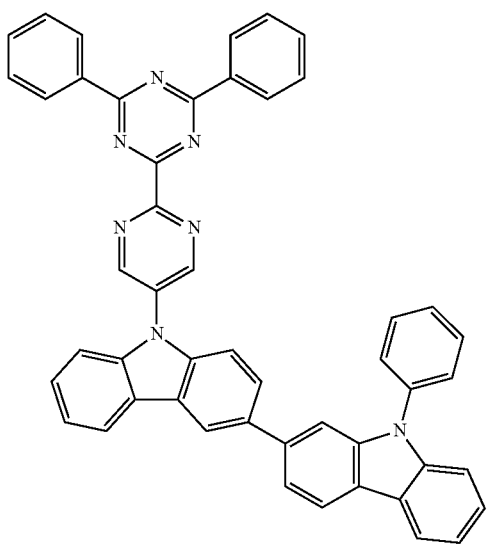
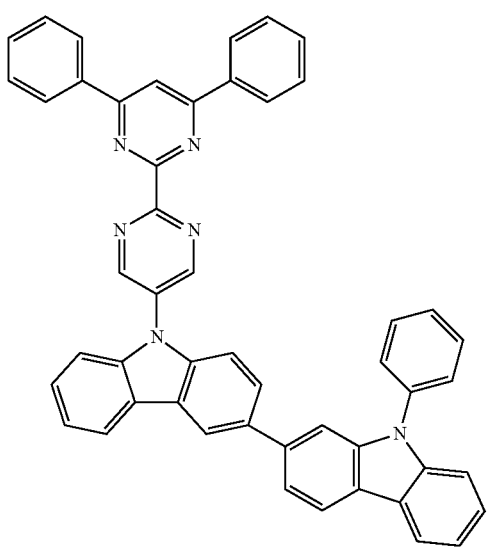
132
-continued
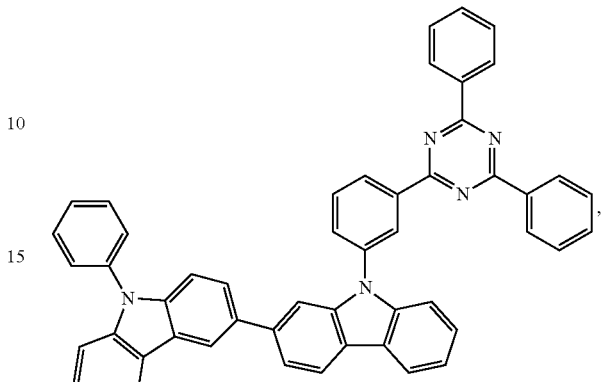
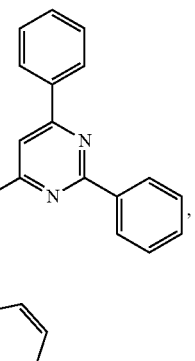
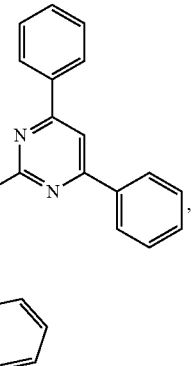

133
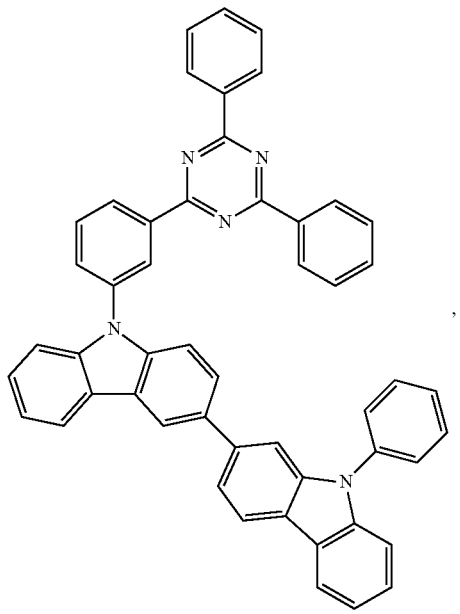
134
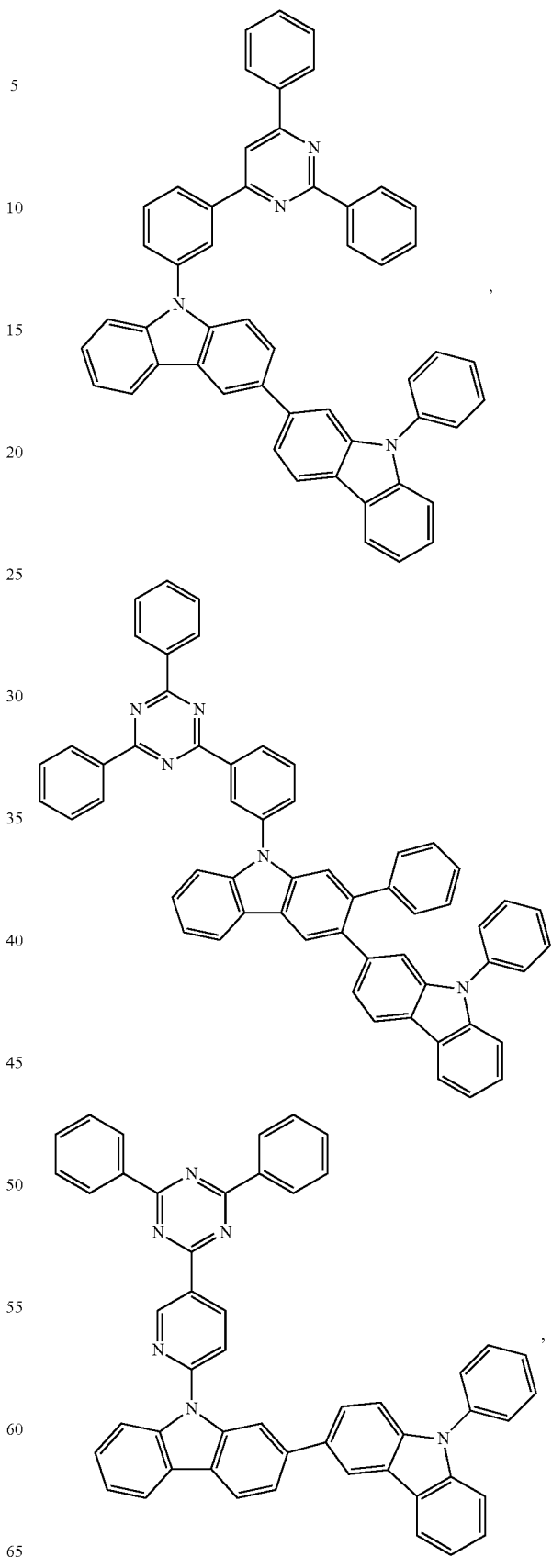

135
-continued
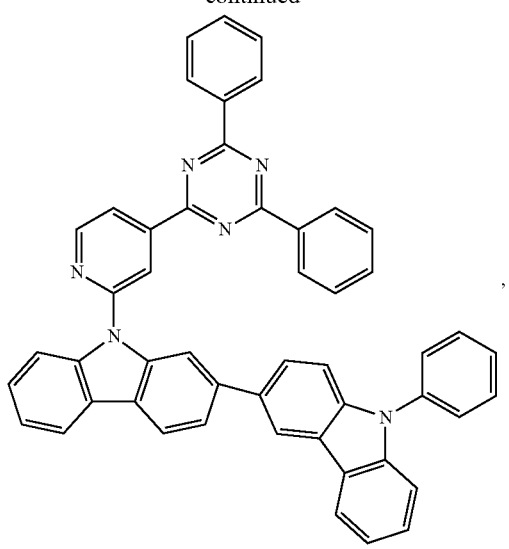
,
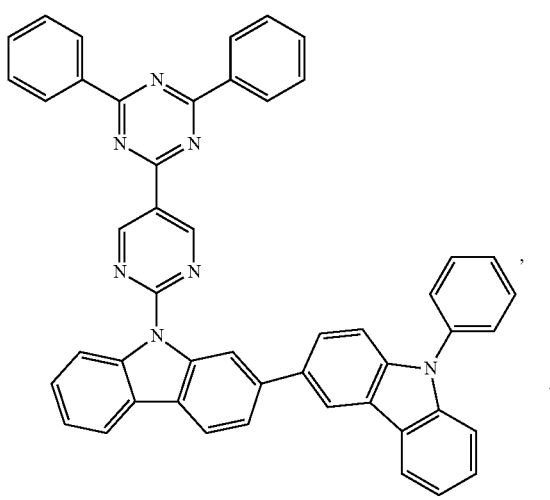
,
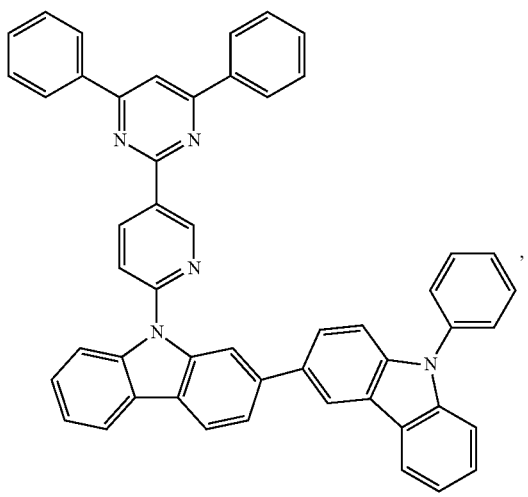
,
136
-continued
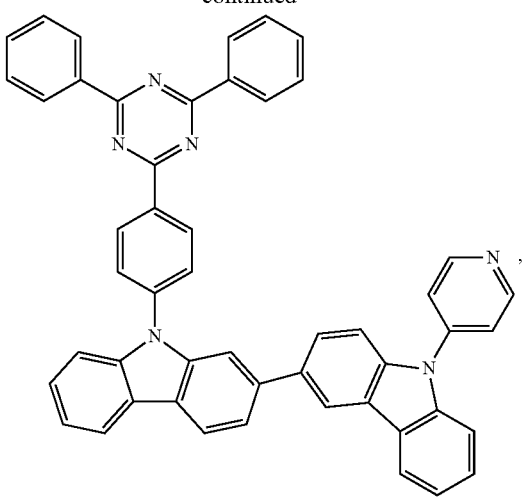
and
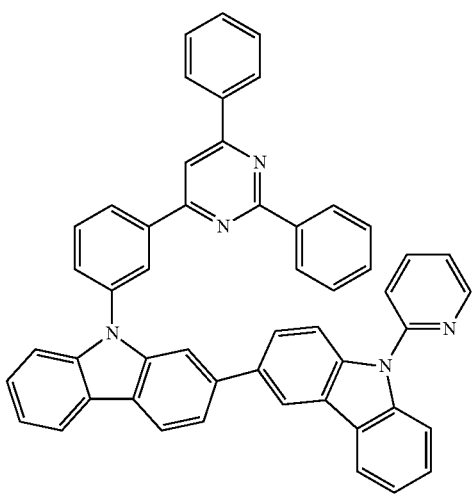
wherein the green phosphorescent dopant material has the formula:
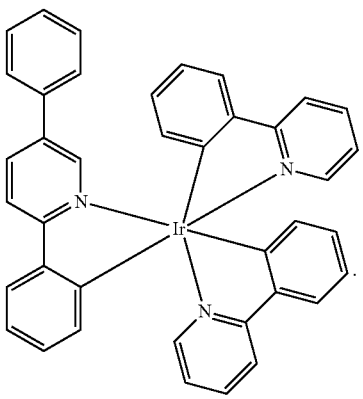
2. The device of claim 1, wherein the host material is a biscarbazole derivative compound represented by a formula 1H or 2H shown below:

(1H)

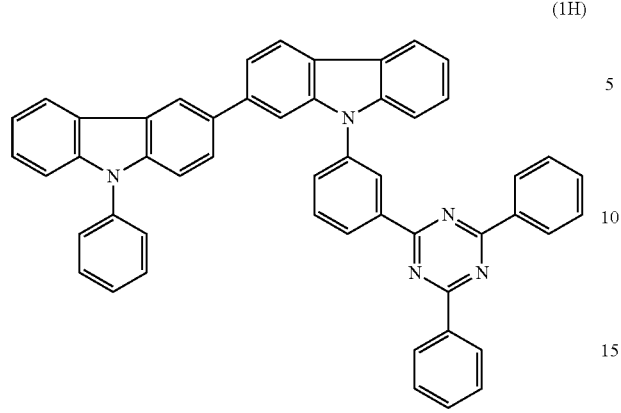

(2H)

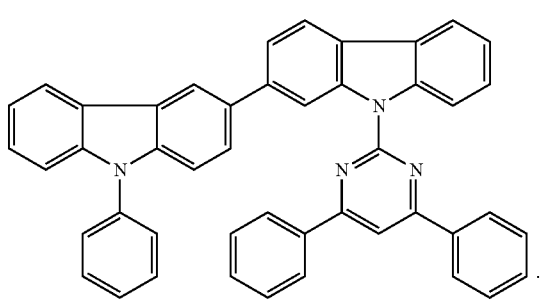

3. An organic electroluminescence device, comprising: a cathode; an anode; and
a plurality of organic thin-film layers provided between the cathode and the anode, the plurality of organic thin-film layers comprising at least an emitting layer comprising:
a first host material;
a second host material; and
a green phosphorescent dopant material,
wherein the first host material is a biscarbazole derivative compound represented by a formula (1A) or (1B) below:

(1A)

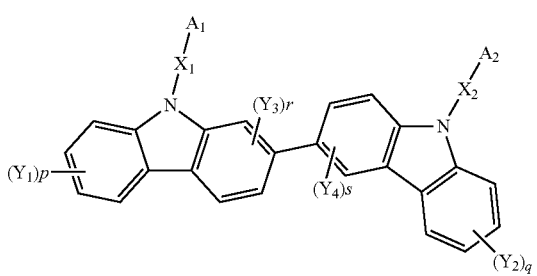

(1B)

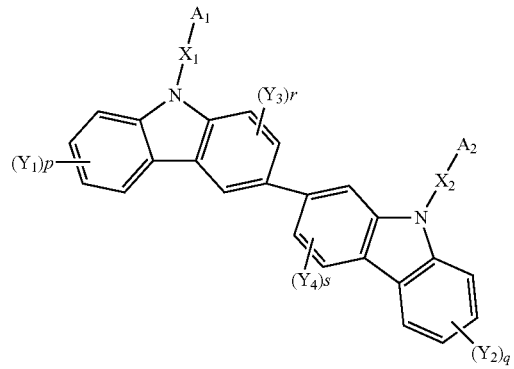

wherein $A_1$ represents a substituted or unsubstituted nitrogen-containing heterocyclic group having 1 to 30 carbon atoms forming a ring;
$A_2$ represents a substituted or unsubstituted aromatic hydrocarbon group having 6 to 30 ring carbon atoms, or substituted or unsubstituted nitrogen-containing heterocyclic group having 1 to 30 ring carbon atoms;
$X_1$ is a linking group and independently represent, a single bond, substituted or unsubstituted aromatic hydrocarbon group having 6 to 30 ring carbon atoms, substituted or unsubstituted fused aromatic hydrocarbon group having 6 to 30 ring carbon atoms, substituted or unsubstituted aromatic heterocyclic group having 2 to 30 ring carbon atoms, or substituted or unsubstituted fused aromatic heterocyclic group having 2 to 30 ring carbon atoms,
$X_2$ is a linking group and independently represent, a single bond substituted or unsubstituted aromatic hydrocarbon group having 6 to 30 ring carbon atoms, substituted or unsubstituted fused aromatic hydrocarbon group having 6 to 30 ring carbon atoms, substituted or unsubstituted aromatic heterocyclic group having 2 to 30 ring carbon atoms, or substituted or unsubstituted fused aromatic heterocyclic group having 2 to 30 ring carbon atoms;
$Y_1$ to $Y_4$ independently represent a hydrogen atom, fluorine atom, cyano group, substituted or unsubstituted alkyl group having 1 to 20 carbon atoms, substituted or unsubstituted alkoxy group having 1 to 20 carbon atoms, substituted or unsubstituted haloalkyl group having 1 to 20 carbon atoms, substituted or unsubstituted haloalkoxy group having 1 to 20 carbon atoms, substituted or unsubstituted alkylsilyl having 1 to 10 carbon atoms, substituted or unsubstituted arylsilyl having 6 to 30 carbon atoms, substituted or unsubstituted aromatic hydrocarbon group having 6 to 30 ring carbon atoms, substituted or unsubstituted fused aromatic hydrocarbon group having 6 to 30 ring carbon atoms, substituted or unsubstituted aromatic heterocyclic group having 2 to 30 ring carbon atoms, or substituted or unsubstituted fused aromatic heterocyclic group having 2 to 30 ring carbon atoms;
adjacent ones of $Y_1$ to $Y_4$ are allowed to be bonded to each other to form a ring structure;
p and q represent an integer of 1 to 4; r and s represent an integer of 1 to 3; and
when p and q are an integer of 2 to 4 and r and s are an integer of 2 to 3, a plurality of $Y_1$ to $Y_4$ are allowed to be the same or different;

wherein the second host material is represented by a formula (1A'), (1B') or (2) below:

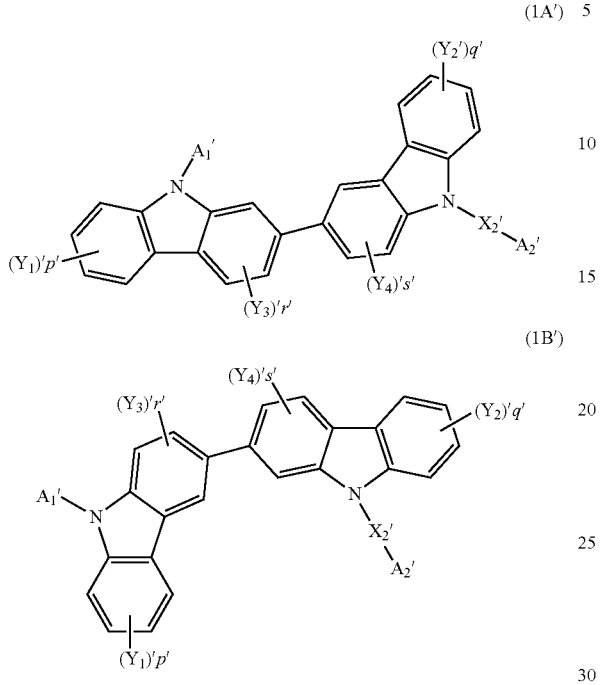

(1A')

(1B')

wherein $A_1'$ represents a substituted or unsubstituted nitrogen-containing heterocyclic group having 1 to 30 carbon atoms forming a ring;
$A_2'$ represents a substituted or unsubstituted aromatic hydrocarbon group having 6 to 30 ring carbon atoms, or substituted or unsubstituted nitrogen-containing heterocyclic group having 1 to 30 ring carbon atoms;
$X_2'$ is a linking group and independently represent, single bond substituted or unsubstituted aromatic hydrocarbon group having 6 to 30 ring carbon atoms, substituted or unsubstituted fused aromatic hydrocarbon group having 6 to 30 ring carbon atoms, substituted or unsubstituted aromatic heterocyclic group having 2 to 30 ring carbon atoms, or substituted or unsubstituted fused aromatic heterocyclic group having 2 to 30 ring carbon atoms;
$Y_1'$ to $Y_4'$ independently represent a hydrogen atom, fluorine atom, cyano group, substituted or unsubstituted alkyl group having 1 to 20 carbon atoms, substituted or unsubstituted alkoxy group having 1 to 20 carbon atoms, substituted or unsubstituted haloalkyl group having 1 to 20 carbon atoms, substituted or unsubstituted haloalkoxy group having 1 to 20 carbon atoms, substituted or unsubstituted alkylsilyl having 1 to 10 carbon atoms, substituted or unsubstituted arylsilyl having 6 to 30 carbon atoms, substituted or unsubstituted aromatic hydrocarbon group having 6 to 30 ring carbon atoms, substituted or unsubstituted fused aromatic hydrocarbon group having 6 to 30 ring carbon atoms, substituted or unsubstituted aromatic heterocyclic group having 2 to 30 ring carbon atoms, or substituted or unsubstituted fused aromatic heterocyclic group having 2 to 30 ring carbon atoms;
adjacent ones of $Y_1'$ to $Y_4'$ are allowed to be bonded to each other to form a ring structure;
p' and q' represent an integer of 1 to 4; r' and s' represent an integer of 1 to 3; and
when p' and q' are an integer of 2 to 4 and r' and s' are an integer of 2 to 3, a plurality of $Y_1'$ to $Y_4'$ are allowed to be the same or different;

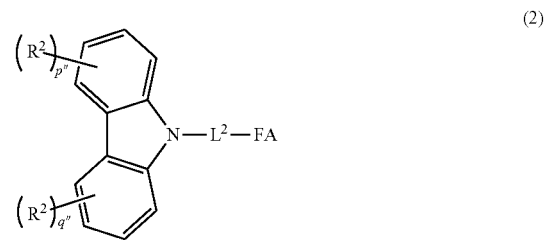

(2)

where $R^2$ independently represents a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 6 to 30 ring carbon atoms, or a substituted or unsubstituted aryloxy group having 6 to 30 ring carbon atoms;
p" and q" are independently an integer of 0 to 4 and p"+q" is at least 1;
a plurality of $R^2$ are mutually the same or different;
adjacent groups of $R^2$ are allowed to bond with each other to form a ring;
at least one $R^2$ is a substituted or unsubstituted carbazolyl group;
$L^2$ represents a single bond or a linking group, the linking group being one or a combination of a substituted or unsubstituted aryl group having 6 to 30 ring carbon atoms, a substituted or unsubstituted heterocyclic group having 5 to 30 ring atoms, and a cycloalkyl group having 5 to 30 ring carbon atoms; and
FA is represented by one of the formulas (2-1) and (2-2)

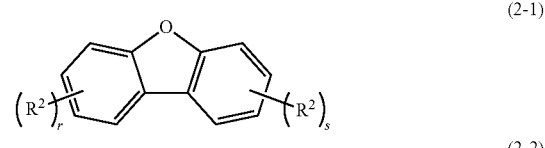

(2-1)

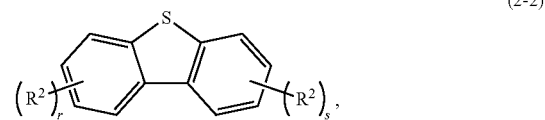

(2-2)

wherein $R^2$ is the same as $R^2$ of the formula (2);
one of $R^2$ is a single bond to bond with $L^2$ in the formula (2); and
r and s are an integer of 0 to 4; and
wherein the green phosphorescent dopant material has the formula:

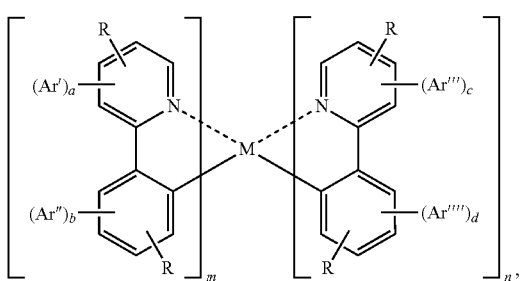

wherein each R is independently selected from the group consisting of H, alkyl, alkenyl, alkynyl, alkylaryl, CN, $CF_3$, $C_nF_{2n+1}$, trifluorovinyl, $CO_2R$, $C(O)R$, $NR_2$, $NO_2$, OR, halo, aryl, heteroaryl, substituted aryl, substituted heteroaryl or a heterocyclic group;

Ar', Ar'', Ar''' and Ar'''' each independently represent a substituted or unsubstituted aryl or heteroaryl unfused substituent on the phenylpyridine ligand;

a is 0 or 1;
b is 0 or 1;
c is 0 or 1;
d is 0 or 1;
m is 1 or 2;
n is 1 or 2;
m+n is the maximum number of ligands that can be coordinated to M, wherein at least one of a, b, c, and d is 1 and when at least one of a and b is 1 and at least one of b and c is 1, at least one of Ar' and Ar'' is different from at least one of Ar''' and Ar''''.

4. The device of claim 3, wherein $A_1$ or $A_1'$ is selected from the group consisting of a substituted or unsubstituted pyridine ring, substituted or unsubstituted pyrimidine ring and substituted or unsubstituted triazine ring.

5. The device of claim 3, wherein $A_1$ or $A_1'$ is selected from a substituted or unsubstituted pyrimidine ring or substituted or unsubstituted triazine ring.

6. The device of claim 3, wherein $A_1$ or $A_1'$ is a substituted or unsubstituted pyrimidine ring.

7. The device of claim 3, wherein $A_1$ or $A_1'$ is a substituted or unsubstituted quinazoline ring.

8. The device of claim 3, wherein $X_1$ or $X_2$ is para phenylene or meta phenylene.

9. The device of claim 3, wherein the green phosphorescent dopant material is a compound represented by a formula 4B below:

(4B)

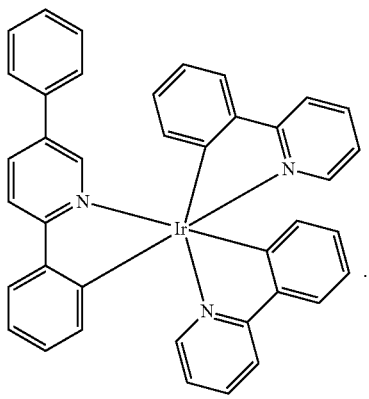

10. The device of claim 9, wherein the first host material is a biscarbazole derivative compound represented by a formula 1H shown below (1H)

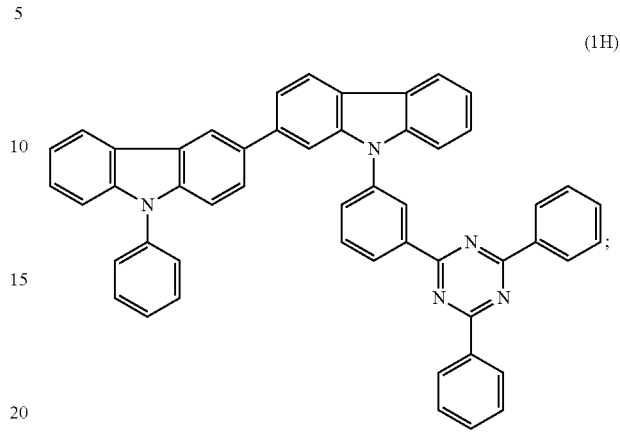

and the second host material is a compound represented by a formula 2H or 3H shown below (2H)

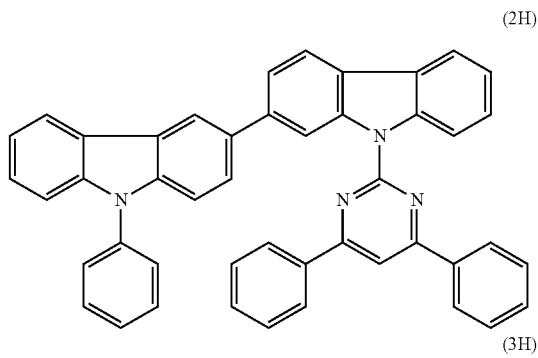

(3H)

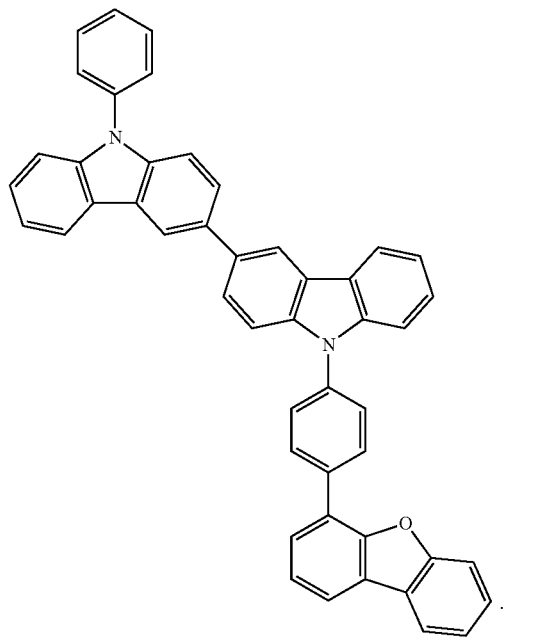

11. The device of claim 3, wherein the second host material is selected from the group consisting of
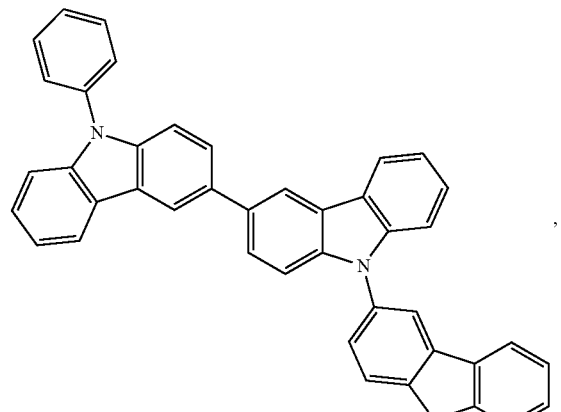
,
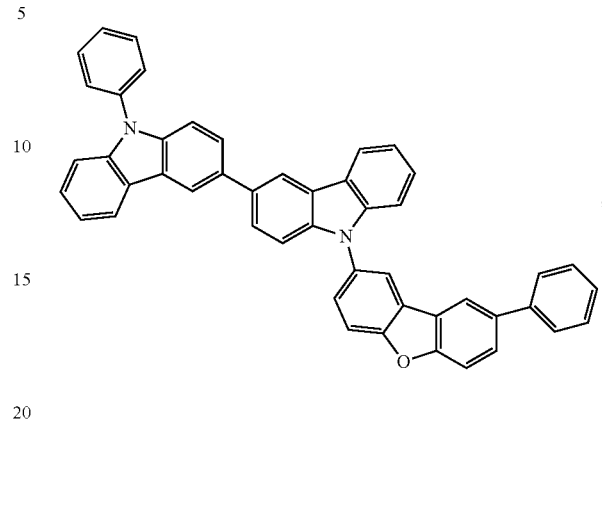
,
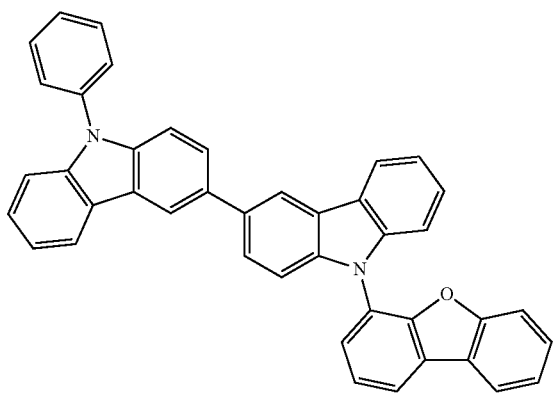
,
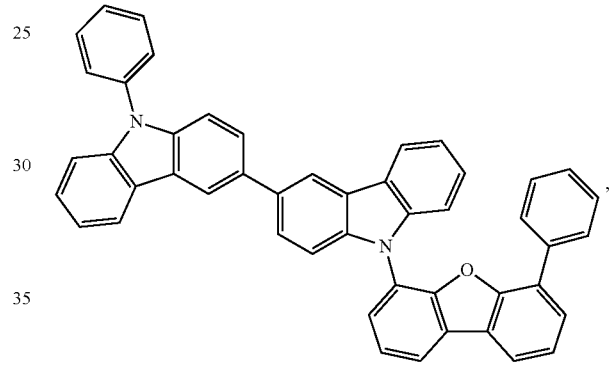
,
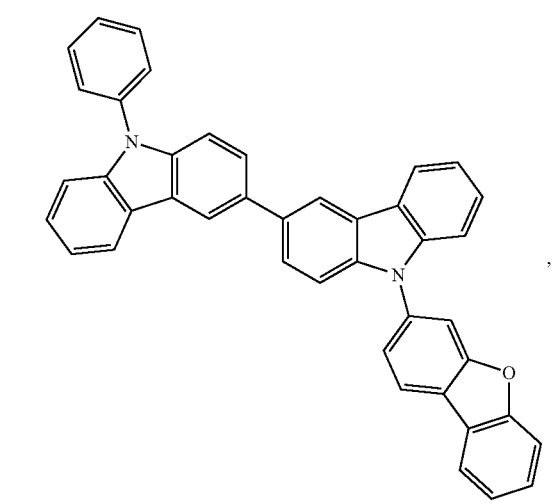
,
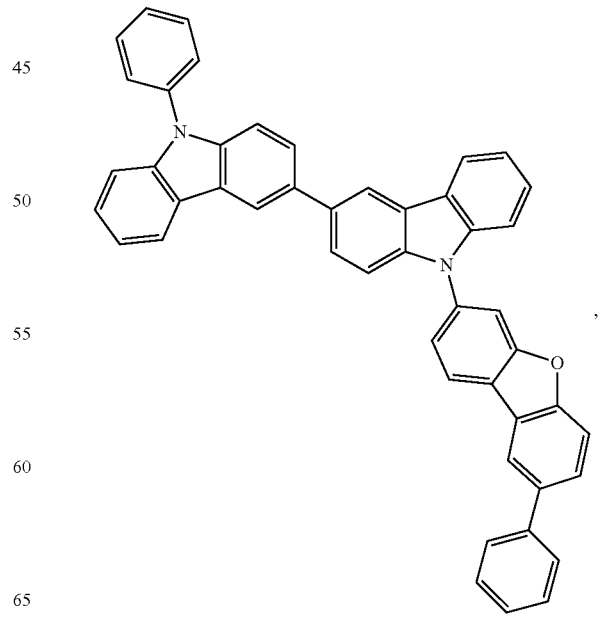
,